US007892798B2

(12) United States Patent
Pompejus et al.

(10) Patent No.: US 7,892,798 B2
(45) Date of Patent: Feb. 22, 2011

(54) **NUCLEIC ACID MOLECULES ENCODING METABOLIC REGULATORY PROTEINS FROM *CORYNEBACTERIUM GLUTAMICUM*, USEFUL FOR INCREASING THE PRODUCTION OF METHIONONE BY A MICROORGANISM**

(75) Inventors: Markus Pompejus, Freinsheim (DE); Burkhard Kröger, Limburgerhof (DE); Hartwig Schröder, Nussloch (DE); Oskar Zelder, Speyer (DE); Gregor Haberhauer, Limburgerhof (DE); Stefan Haefner, Ludwigshafen (DE); Corrinna Klopprogge, Ludwigshafen (DE)

(73) Assignee: Evonik Degussa GmbH, Essen (DE)

( * ) Notice: Subject to any disclaimer, the term of this patent is extended or adjusted under 35 U.S.C. 154(b) by 239 days.

(21) Appl. No.: 10/307,138

(22) Filed: Nov. 29, 2002

(65) Prior Publication Data

US 2003/0162267 A1    Aug. 28, 2003

Related U.S. Application Data

(63) Continuation-in-part of application No. 09/602,874, filed on Jun. 23, 2000, now abandoned.

(60) Provisional application No. 60/141,031, filed on Jun. 25, 1999, provisional application No. 60/142,690, filed on Jul. 1, 1999, provisional application No. 60/151,251, filed on Aug. 27, 1999, provisional application No. 60/422,618, filed on Oct. 30, 2002.

(30) Foreign Application Priority Data

| Jul. 1, 1999 | (DE) | 199 30 476 |
| Jul. 8, 1999 | (DE) | 199 31 419 |
| Jul. 8, 1999 | (DE) | 199 31 420 |
| Jul. 9, 1999 | (DE) | 199 32 122 |
| Jul. 9, 1999 | (DE) | 199 32 128 |
| Jul. 9, 1999 | (DE) | 199 32 134 |
| Jul. 9, 1999 | (DE) | 199 32 206 |
| Jul. 9, 1999 | (DE) | 199 32 207 |
| Jul. 14, 1999 | (DE) | 199 33 003 |
| Aug. 31, 1999 | (DE) | 199 41 390 |
| Sep. 3, 1999 | (DE) | 199 42 088 |
| Sep. 3, 1999 | (DE) | 199 42 124 |

(51) Int. Cl.
*C12P 13/12* (2006.01)
*C12P 21/06* (2006.01)
*C12N 1/20* (2006.01)
*C12N 15/00* (2006.01)
*C07H 21/04* (2006.01)

(52) U.S. Cl. .......... 435/113; 435/69.1; 435/252.3; 435/252.32; 435/320.1; 536/23.1; 536/23.4; 536/23.7

(58) Field of Classification Search .......... None
See application file for complete search history.

(56) References Cited

U.S. PATENT DOCUMENTS 3,729,381 A    4/1973  Nakayama et al.
2005/0153402 A1  7/2005  Pompejus et al.

FOREIGN PATENT DOCUMENTS

| EP | 1108790 A2 | 6/2001 |
| EP | 1108790 A2 * | 6/2001 |
| JP | 50-31092 | 3/1975 |
| WO | WO-02/097096 A2 | 12/2002 |

OTHER PUBLICATIONS

Seffernick et al. J. Bateriol., vol. 183, pp. 2405-2410, 2001.*
Branden et al. "Introduction to Protein Structure", Garland Publishing Inc., New York, 1991, p. 247.*
Witkowski et al., Biochemistry 38:11643-11650, 1999.*
Renna et al., J Bacteriol 175:3863-3875, 1993.*
Dictionary definition of "positively" at Encarta.com, last viewed on Jan. 16, 2008, 2 pages.*
Kolmar et al., EMBO J. 14:3895-3904, 1995.*
Hwang et al., J. Bacteriol. 184:1277-1286, 2002.*
Belfaiza, J. et al.. "Direct Sulfhydrylation for Methionine Biosynthesis in *Leptospira meyeri*," *Journal of Bacteriology*, vol. 180(2):250-255 (1998).
Follettie, M.T. et al., "Organization and regulation of the *Corynebacterium glutamicum* hom-thrB and thrC loci," *Molecular Microbiology*, vol. 2(1):53-62 (1988).
Henikoff, S. et al., "A Large family of bacterial activator proteins," *Proc. Natl. Acad. Sci.*, vol. 85: 6602-6606 (1988).
Hwang, Byung-Joon et al., "*Corynebacterium glutamicum* Utilizes both Transsulfuration and Direct Sulfhydrylation Pathways for Methionine Biosynthesis," *Journal of Bacteriology*, vol. 184(5):1277-1286 (2002).
Muraoka, Shin et al., "Crystal Structure of a Full-length LysR-type Transcriptional Regulator, CnbR: Unusual Combination of Two Subunit Forms and Molecular Bases for Causing and Changing DNA Bend," *J. Mol. Biol.*, vol. 328:555-566 (2003).
Schell, Mark A., "Molecular Biology of the LysR Family of Transcriptional Regulators," *Annu. Rev. Microbiol.*, vol. 47:597-626 (1993).

(Continued)

*Primary Examiner*—David J Steadman
(74) *Attorney, Agent, or Firm*—Nelson Mullins Riley & Scarborough, LLP

(57) ABSTRACT

Isolated nucleic acid molecules, which encode novel metabolic regulatory proteins from *Corynebacterium glutamicum* are described. These nucleic acid molecules are involved in the biosynthesis of a fine chemical, e.g., methionine biosynthesis. The invention also provides antisense nucleic acid molecules, recombinant expression vectors containing metabolic regulatory nucleic acid molecules, and host cells into which the expression vectors have been introduced. The invention still further provides methods of producing methionine from microorganisms, e.g., *C. glutamicum*, which involve culturing recombinant microorganisms which overexpress or underexpress at least one metabolic regulatory molecule of the invention under conditions such that methionine is produced. Also featured are methods of producing a fine chemical, e.g., methionine, which involve culturing recombinant microorganisms having selected metabolic regulatory genes deleted or mutated under conditions such that the fine chemical, e.g., methionine, is produced.

56 Claims, 1 Drawing Sheet

OTHER PUBLICATIONS

Database Accession No. Q9EW12, "Putative tetR-family transcriptional regulator," *Streptomyces coelicolor*, Mar. 1, 2004.

Database Accession No. AP005223, "Comparative complete genome sequence analysis of the amino acid replacements responsible for the thermostability of *Corynebacterium efficiens*," Nishio, Y. et al, Jul. 24, 2003.

Database Accession No. AP005281, "Complete genomic sequence of *Corynebacterium glutamicum* ATCC 13032," Nakagawa, S., Aug. 8, 2002.

Adhya, Sankar, "The *LAC* and *GAL* Operons Today," *Regulation of Gene Expression in Escherichia coli*, Chapman & Hall, New York, pp. 181-200, 1996.

Boos, Winfried et al, "The Maltose System," *Regulation of Gene Expression in Escherichia coli*, Chapman & Hall, New York, pp. 201-229, 1996.

Helmann, John D. et al, "Structure and Function of bacterial Sigma Factors," *Ann. Rev. Biochem.*, vol. 57:839-872 (1988).

Henkin, T.M. et al, "Catabolite repression of α-amylase gene expression in *Bacillus subtilis* involves a *trans*-acting gene product homologous to the *Escherichia coli lacI* and *galR* repressors," *Molecular Microbiology*, vol. 5(3):575-584 (1991).

Lewin, B. et al, "Controlling Prokaryotic Genes by Transcription," Oxford University Press: Oxford, pp. 213-301, 1990.

Kase, Hiroshi et al, "Isolation and Characterization of S-Adenosylmethionine-requiring Mutants and Role of S-Adenosylmethionine in the Regulation of Methionine Biosynthesis in *Corynebacterium glutamicum*," *Agr. Biol. Chem.*, vol. 39(1):161-168 (1975).

U.S. Appl. No. 09/602,874, Markus Pompejus et al.

Kase, Hiroshi et al, "L-Methionine Production by Methionine Analog-resistant Mutants of *Corynebacterium glutamicum*," *Agr. Biol. Chem.*, vol. 39(1):153-160 (1975).

Mondal, S. et al, "Enhancement of methionine production by methionine analogue ethionine resistant mutants of *Brevibacterium heali*," *Acta Biotechnologica*, vol. 14(2):199-204 (1994).

Moran, Charles P., "RNA Polymerase and Transcription Factors," *Bacillus subtilis and other gram-positive bacteria*, Sonenshein, A.L. et al, eds. ASM: Washington, D.C., pp. 653-667, 1993.

Nishio, Yousuke et al, "Comparative Complete Genome Sequence Analysis of the Amino Acid Replacements Responsible for the Thermostability of *Corynebacterium efficiens*," *Genome Research*, vol. 13:1572-1579 (2003).

Old, Iain G. et al, "Regulation of Methionine Biosynthesis in the Enterobacteriaceae," *Prog. Biophys. Molec. Biol.*, vol. 56:145-185 (1991).

Sharma, Sanjay et al, "Effect of Dissolved Oxygen on Continuous Production of Methionine," *Eng. Life Sci. J.*, vol. 2:69-73 (2001).

\* cited by examiner

US 7,892,798 B2

NUCLEIC ACID MOLECULES ENCODING METABOLIC REGULATORY PROTEINS FROM *CORYNEBACTERIUM GLUTAMICUM*, USEFUL FOR INCREASING THE PRODUCTION OF METHIONONE BY A MICROORGANISM

RELATED APPLICATIONS

This application claims priority to U.S. Provisional Application Ser. No. 60/422,618, filed on Oct. 30, 2002. This application also claims priority to U.S. application Ser. No. 09/602,874, filed on Jun. 23, 2000. This application also claims priority to U.S. Provisional Patent Application No. 60/141,031, filed Jun. 25, 1999, U.S. Provisional Patent Application No. 60/142,690, filed Jul. 1, 1999, and also to U.S. Provisional Patent Application No. 60/151,251, filed Aug. 27, 1999. This application also claims priority to German Patent Application No. 19930476.9, filed Jul. 1, 1999, German Patent Application No. 19931419.5, filed Jul. 8, 1999, German Patent Application No. 19931420.9, filed Jul. 8, 1999, German Patent Application No. 19932122.1, filed Jul. 9, 1999, German Patent Application No. 19932128.0, filed Jul. 9, 1999, German Patent Application No. 19932134.5, filed Jul. 9, 1999, German Patent Application No. 19932206.6, filed Jul. 9, 1999, German Patent Application No. 19932207.4, filed Jul. 9, 1999, German Patent Application No. 19933003.4, filed Jul. 14, 1999, German Patent Application No. 19941390.8, filed Aug. 31, 1999, German Patent Application No. 19942088.2, filed Sep. 3, 1999, and German Patent Application No. 19942124.2, filed Sep. 3, 1999. The entire contents of all of the aforementioned applications are hereby expressly incorporated herein by this reference.

BACKGROUND OF THE INVENTION

Methionine is currently produced as a racemic mixture of DL-methionine by a well established chemical process. Most DL-methionine is being produced by variations of the same chemical procedure method involving toxic, dangerous, flammable, unstable, and highly odorous starting materials or intermediates. The starting materials for the chemical synthesis are: acrolein, methylmercaptan and hydrogen cyanide. The chemical synthesis involves the reaction of methylmercaptan and acrolein producing the intermediate 3-methylmercaptopropionaldehyde (MMP). In the further process the MMP reacts with hydrogen cyanide to form the 5-(2-methylthioethyl) hydantoin, which then can be hydrolyzed using 2 equivalents of caustics such as NaOH together with one half equivalent $Na_2CO_3$ to yield sodium-DL-methioninate and one equivalent $Na_2CO_3$ one equivalent $NH_3$ and one half equivalent $CO_2$. In the succeeding step the sodium-DL-methioninate is neutralized with 1.5 equiv. sulfuric acid and 1 equiv.$Na_2CO_3$ to yield DL-methionine $Na_2SO_4$ and $CO_2$. It is obvious that such a chemical process yields a large molar excess of unused salts in comparison to the amount of methionine that is produced. This fact poses an economic and ecologic challenge.

Fermentative processes are usually based on cultivating microorganisms on nutrients including carbohydrate source (e.g., sugars such as glucose fructose or saccharose), nitrogen sources (e.g., ammonia) and sulfur sources (e.g., sulfate or thiosulfate) together with other necessary media components. The process yields only the natural product L-methionine and only biomass as a byproduct. Since no toxic, dangerous, flammable unstable, and highly odorous starting materials are being used and no salt is produced by a fermentative process, there is an advantage of this process over the chemical methionine synthesis. Methionine can be produced in organisms such as *E. coli* or Corynebacter (Kase H., Nakayama K. (1975) *Agric. Biol. Chem.* 39 pp 153-160; Chatterjee et al. (1999) *Acta Biotechnol.* 14, pp199-204; Harma S. Gomes, (2001) *J. Eng. Life Sci.* 1 pp. 69-73, JP 50031092, DE 2105189).

However, in all reported cases the yields for fermentatively produced methionine seem to be too low for an economic production. Therefore, an improved method is needed.

SUMMARY OF THE INVENTION

The invention provides novel bacterial nucleic acid molecules which modulate the biosynthesis of fine chemicals, e.g., methionine. It has been found that the metabolic regulatory ("MR") molecules of the invention are involved in biosynthesis of a fine chemical, e.g., methionine. In particular, it has been found that the MR molecule RXA00655 is a negative regulator, e.g., transcriptional regulator, of methionine biosynthesis, cysteine biosynthesis, and/or the sulfur reduction pathway. It has also been found that the MR molecule RXN02910 is a positive regulator, e.g., transcriptional regulator, of methionine biosynthesis. The nucleotide sequence of RXA00655 is set forth herein as SEQ ID NO:1 and the polypeptide sequence of RXA00655 is set forth herein as SEQ ID NO:2. The nucleotide sequence of RXN02910 is set forth herein as SEQ ID NO:5 and the polypeptide sequence of RXN02910 is set forth herein as SEQ ID NO:6. Homologous proteins of RXA00655 are set forth herein as SEQ ID NOs: 19, 21 and 23. The corresponding nucleotide sequences of these RXA00655 homologous proteins are set forth herein as SEQ ID NOs: 18, 20 and 22.

Modulation of the expression of the MR nucleic acids of the invention, e.g. increasing expression of the RXN02910 nucleic acid molecule or increasing the activity of the RXN02910 protein, suppressing expression of the RXA00655 nucleic acid molecule or suppressing the activity of the RXA00655 protein, or modification of the sequence of the MR nucleic acid molecules of the invention to alter the activity of the MR nucleic acid molecule, can be used to modulate, e.g., increase, the production of a fine chemical, e.g., methionine, cysteine, and/or other compounds of the methionine biosynthetic pathway, the sulfur reduction pathway, and/or the cysteine biosynthetic pathway from a microorganism (e.g., to improve the yield or production of a fine chemical, e.g., methionine or other compounds of the methionine biosynthetic pathway, from a *Corynebacterium* or *Brevibacterium* species). In another embodiment, increasing the expression or activity of the RXN02910 nucleic acid or protein and suppression of the expression or activity of the RXA00655 nucleic acid or protein, in combination, can be used to modulate, e.g., increase, the production of a fine chemical, e.g., methionine, cysteine, and/or other compounds of the methionine biosynthetic pathway, the sulfur reduction pathway, and/or the cysteine biosynthetic pathway from a microorganism (e.g., *Corynebacterium* or *Brevibacterium* species).

Accordingly, the present invention features methods of producing methionine as well as other compounds of the methionine biosynthetic pathway. Such methods include culturing microorganisms overexpressing the RXN02910 gene product under conditions such that methionine, or other compounds of the methionine biosynthetic pathway, are produced. Such methods also include culturing microorganisms with inhibited expression of the RXA00655 gene product such that methionine, or other compounds of the methionine biosynthetic pathway, the sulfur reduction pathway, and/or the cysteine biosynthetic pathway are produced. The present invention also provides methods for producing a fine chemical comprising culturing microorganisms overexpressing the RXN02910 gene product in combination with microorganisms with inhibited expression of the RXA00655 gene product.

The present invention also features methods of increasing production of a sulfur-containing compound by a microorganism comprising culturing a microorganism which overexpresses a positive regulator of methionine biosynthesis, e.g., RXN02910, under conditions such that production of the sulfur-containing compound is increased. Furthermore, the present invention features methods of increasing production of a sulfur-containing compound by a microorganism comprising culturing a microorganism which underexpresses a negative regulator of methionine biosynthesis, e.g., RXA00655, under conditions such that production of the sulfur-containing compound is increased.

The MR proteins encoded by the novel nucleic acid molecules of the invention are capable of, for example, performing a function involved in the transcriptional, translational, or posttranslational regulation of proteins important for the normal metabolic functioning of cells. Given the availability of cloning vectors for use in *Corynebacterium glutamicum*, such as those disclosed in Sinskey et al., U.S. Pat. No. 4,649,119, and techniques for genetic manipulation of *C. glutamicum* and the related *Brevibacterium* species (e.g., *lactofermentum*) (Yoshihama et al, *J. Bacteriol.* 162: 591-597 (1985); Katsumata et al., *J. Bacteriol.* 159: 306-311 (1984); and Santamaria et al., *J. Gen. Microbiol.* 130: 2237-2246 (1984)), the nucleic acid molecules of the invention may be utilized in the genetic engineering of this organism to make it a better or more efficient producer of a fine chemical, e.g., methionine.

This improved yield, production and/or efficiency of production of a fine chemical, e.g., methionine, may be due to a direct effect of manipulation of a gene of the invention, e.g., RXA00655 or RXN02910, or it may be due to an indirect effect of such manipulation. Specifically, alterations in *C. glutamicum* MR proteins which normally regulate the yield, production and/or efficiency of production of the methionine metabolic pathways may have a direct impact on the overall production or rate of production of a fine chemical, e.g., methionine, cysteine, and/or other compounds of the methionine biosynthetic pathway, the sulfur reduction pathway, and/or the cysteine biosynthetic pathway from this organism. Alterations in the proteins involved in the methionine metabolic pathway may also have an indirect impact on the yield, production and/or efficiency of production of a desired fine chemical, e.g., methionine. Regulation of metabolism is necessarily complex, and the regulatory mechanisms governing different pathways may intersect at multiple points such that more than one pathway can be rapidly adjusted in accordance with a particular cellular event. This enables the modification of a regulatory protein for one pathway to have an impact on the regulation of many other pathways as well, some of which may be involved in the biosynthesis or degradation of a desired fine chemical, e.g., methionine. In this indirect fashion, the modulation of action of an MR protein has an impact on the production of a fine chemical produced by a pathway different from one which that MR protein directly regulates.

The nucleic acid and protein molecules of the invention may be utilized to directly improve the yield, production, and/or efficiency of production of methionine from *Corynebacterium glutamicum*. Using recombinant genetic techniques well known in the art, one or more of the regulatory proteins of the invention may be manipulated such that its function or expression is modulated. For example, the mutation of an MR protein, e.g., RXA00655, which is involved in the repression of transcription of a gene, e.g., the metY gene, encoding a polypeptide which is required for the biosynthesis of an amino acid, e.g., methionine, such that it no longer is able to repress transcription may result in an increase in production of that amino acid. Similarly, the alteration of activity of an MR protein resulting in increased translation or activating posttranslational modification of a *C. glutamicum* protein involved in the biosynthesis of a desired fine chemical, e.g., methionine, may in turn increase the production of that chemical. The opposite situation may also be of benefit: by increasing the repression of transcription or translation, or by posttranslational negative modification of a *C. glutamicum* protein involved in the regulation of a degradative pathway for a compound, one may increase the production of this chemical. In each case, the overall yield or rate of production of the desired fine chemical may be increased.

It is also possible that such alterations in the protein and nucleotide molecules of the invention may improve the yield, production, and/or efficiency of production of fine chemicals, e.g., methionine, through indirect mechanisms. The metabolism of any one compound is necessarily intertwined with other biosynthetic and degradative pathways within the cell, and necessary cofactors, intermediates, or substrates in one pathway are likely supplied or limited by another such pathway. Therefore, by modulating the activity of one or more of the regulatory proteins of the invention, the production or efficiency of activity of another fine chemical biosynthetic or degradative pathway may be impacted. Further, the manipulation of one or more regulatory proteins may increase the overall ability of the cell to grow and multiply in culture, particularly in large-scale fermentative culture, where growth conditions may be suboptimal. For example, by mutating an MR protein of the invention which would normally cause a repression in the biosynthesis of nucleotides in response to suboptimal extracellular supplies of nutrients (thereby preventing cell division) such that it is decreased in repressor ability, one may increase the biosynthesis of nucleotides and perhaps increase cell division. Changes in MR proteins which result in increased cell growth and division in culture may result in an increase in yield, production, and/or efficiency of production of one or more desired fine chemicals from the culture, due at least to the increased number of cells producing the chemical in the culture.

The invention provides novel nucleic acid molecules which encode proteins, referred to herein as metabolic pathway proteins (MR), which are capable of, for example, performing an enzymatic step involved in the transcriptional, translational, or posttranslational regulation of metabolic pathways in *C. glutamicum*. Nucleic acid molecules encoding an MR protein are referred to herein as MR nucleic acid molecules. In a preferred embodiment, the MR protein participates in the transcriptional, translational, or posttranslational regulation of one or more metabolic pathways.

Accordingly, one aspect of the invention pertains to isolated nucleic acid molecules (e.g., cDNAs, DNAs, or RNAs) comprising a nucleotide sequence encoding an MR protein or biologically active portions thereof, as well as nucleic acid fragments suitable as primers or hybridization probes for the detection or amplification of MR-encoding nucleic acid (e.g., DNA or mRNA). In particularly preferred embodiments, the isolated nucleic acid molecule comprises one of the nucleotide sequences set forth in SEQ ID NO: 1, SEQ ID NO: 5, SEQ ID NO: 16, SEQ ID NO: 18, SEQ ID NO: 20, or SEQ ID NO: 22 or the coding region or a complement thereof of one of these nucleotide sequences. In other particularly preferred embodiments, the isolated nucleic acid molecule of the invention comprises a nucleotide sequence which hybridizes to or is at least about 50%, preferably at least about 60%, more preferably at least about 70%, 80% or 90%, and even more preferably at least about 90%, 91%, 92%, 93%, 94%, 95%, 96%, 97%, 98%, 99% or more homologous to a nucleotide sequence set forth in SEQ ID NO: 1, SEQ ID NO: 5, SEQ ID NO: 16, SEQ ID NO: 18, SEQ ID NO: 20, or SEQ ID NO: 22, or a portion thereof. In other preferred embodiments, the isolated nucleic acid molecule encodes one of the amino acid sequences set forth in SEQ ID NO: 2, SEQ ID NO: 6, SEQ ID NO: 17, SEQ ID NO: 19, SEQ ID NO: 21, or SEQ ID NO: 23. The preferred MR proteins of the present invention also preferably possess at least one of the MR activities described herein.

In another embodiment, the isolated nucleic acid molecule encodes a protein or portion thereof wherein the protein or portion thereof includes an amino acid sequence which is sufficiently homologous to an amino acid sequence of SEQ ID NO: 2, SEQ ID NO: 6, SEQ ID NO: 17, SEQ ID NO: 19, SEQ ID NO: 21, or SEQ ID NO: 23, e.g., sufficiently homologous to an amino acid sequence of SEQ ID NO: 2, SEQ ID NO: 6, SEQ ID NO: 17, SEQ ID NO: 19, SEQ ID NO: 21, or SEQ ID NO: 23 such that the protein or portion thereof maintains an MR activity, e.g., modulation of biosynthesis of a fine chemical, e.g., methionine. Preferably, the protein or portion thereof encoded by the nucleic acid molecule maintains the ability to transcriptionally, translationally, or post-translationally regulate a metabolic pathway in *C. glutamicum*. In one embodiment, the protein encoded by the nucleic acid molecule is at least about 50%, preferably at least about 60%, and more preferably at least about 70%, 80%, or 90% and most preferably at least about 90%, 91%, 92%, 93%, 94%, 95%, 96%, 97%, 98%, or 99% or more homologous to an amino acid sequence of SEQ ID NO: 2, SEQ ID NO: 6, SEQ ID NO: 17, SEQ ID NO: 19, SEQ ID NO: 21, or SEQ ID NO: 23 (e.g., an entire amino acid sequence selected from those sequences set forth in SEQ ID NO: 2, SEQ ID NO: 6, SEQ ID NO: 17, SEQ ID NO: 19, SEQ ID NO: 21, or SEQ ID NO: 23). In another preferred embodiment, the protein is a full length *C. glutamicum* protein which is substantially homologous to an entire amino acid sequence of SEQ ID NO: 2, SEQ ID NO: 6, SEQ ID NO: 17, SEQ ID NO: 19, SEQ ID NO: 21, or SEQ ID NO: 23 (encoded by an open reading frame shown in SEQ ID NO: 1, SEQ ID NO: 5, SEQ ID NO: 16, SEQ ID NO: 18, SEQ ID NO: 20, or SEQ ID NO: 22).

In another preferred embodiment, the isolated nucleic acid molecule is derived from *C. glutamicum* and encodes a protein (e.g., an MR fusion protein) which includes a biologically active domain which is at least about 50% or more homologous to one of the amino acid sequences of SEQ ID NO: 2, SEQ ID NO: 6, SEQ ID NO: 17, SEQ ID NO: 19, SEQ ID NO: 21, or SEQ ID NO: 23 and is able to transcriptionally, translationally, or posttranslationally regulate a metabolic pathway in *C. glutamicum*, or has one or more of the activities set forth herein, and which also includes heterologous nucleic acid sequences encoding a heterologous polypeptide or regulatory regions.

In another embodiment, the isolated nucleic acid molecule is at least 15, 20, 25, 30, 40, 50, 60, 70, 80, 90, 100, 110, 120, 130, 140, 150, 160, 170, 180, 190, 200, 210, 220, 225 or more nucleotides in length and hybridizes under stringent conditions to a nucleic acid molecule comprising a nucleotide sequence of SEQ ID NO: 1, SEQ ID NO: 5, SEQ ID NO: 16, SEQ ID NO: 18, SEQ ID NO: 20, or SEQ ID NO: 22. Preferably, the isolated nucleic acid molecule corresponds to a naturally-occurring nucleic acid molecule. More preferably, the isolated nucleic acid encodes a naturally-occurring *C. glutamicum* MR protein, or a biologically active portion thereof.

Another aspect of the invention pertains to vectors, e.g., recombinant expression vectors, containing the nucleic acid molecules of the invention, and host cells into which such vectors have been introduced. In one embodiment, such a host cell is used to produce an MR protein by culturing the host cell in a suitable medium. The MR protein can be then isolated from the medium or the host cell.

Yet another aspect of the invention pertains to a genetically altered microorganism in which an MR gene has been introduced or altered. In one embodiment, the genome of the microorganism has been altered by introduction of a nucleic acid molecule of the invention encoding wild-type or mutated MR sequence as a transgene. In another embodiment, an endogenous MR gene within the genome of the microorganism has been altered, e.g., functionally disrupted, by homologous recombination with an altered MR gene. In another embodiment, an endogenous or introduced MR gene in a microorganism has been altered by one or more point mutations, deletions, or inversions, but still encodes a functional MR protein. In still another embodiment, one or more of the regulatory regions (e.g., a promoter, repressor, or inducer) of an MR gene in a microorganism has been altered (e.g., by deletion, truncation, inversion, or point mutation) such that the expression of the MR gene is modulated. In a preferred embodiment, the microorganism belongs to the genus *Corynebacterium* or *Brevibacterium*, with *Corynebacterium glutamicum* being particularly preferred. In a preferred embodiment, the microorganism is also utilized for the production of a desired compound, such as an amino acid, with methionine, being particularly preferred.

The invention also provides an isolated preparation of an MR protein. In preferred embodiments, the MR protein comprises an amino acid sequence of SEQ ID NO: 2, SEQ ID NO: 6, SEQ ID NO: 17, SEQ ID NO: 19, SEQ ID NO: 21, or SEQ ID NO: 23. In another preferred embodiment, the invention pertains to an isolated full length protein which is substantially homologous to an entire amino acid sequence of SEQ ID NO: 2, SEQ ID NO: 6, SEQ ID NO: 17, SEQ ID NO: 19, SEQ ID NO: 21, or SEQ ID NO: 23 (encoded by an open reading frame set forth in SEQ ID NO: 1, SEQ ID NO: 5, SEQ ID NO: 16, SEQ ID NO: 18, SEQ ID NO: 20, or SEQ ID NO: 22). In yet another embodiment, the protein is at least about 50%, preferably at least about 60%, and more preferably at least about 70%, 80%, or 90%, and most preferably at least about 90%, 91%, 92%, 93%, 94%, 95%, 96%, 97%, 98%, or 99% or more homologous to an entire amino acid sequence of SEQ ID NO: 2, SEQ ID NO: 6, SEQ ID NO: 17, SEQ ID NO: 19, SEQ ID NO: 21, or SEQ ID NO: 23. In other embodiments, the isolated MR protein comprises an amino acid sequence which is at least about 50% or more homologous to one of the amino acid sequences of SEQ ID NO: 2, SEQ ID NO: 6, SEQ ID NO: 17, SEQ ID NO: 19, SEQ ID NO: 21, or SEQ ID NO: 23 and is able to transcriptionally, translationally, or posttranslationally regulate one or more metabolic pathways in *C. glutamicum*, or has one or more of the activities set forth herein.

Alternatively, the isolated MR protein can comprise an amino acid sequence which is encoded by a nucleotide sequence which hybridizes, e.g., hybridizes under stringent conditions, or is at least about 50%, preferably at least about 60%, more preferably at least about 70%, 80%, or 90%, and even more preferably at least about 90%, 91%, 92%, 93%, 94%, 95%, 96%, 97%, 98,%, or 99% or more homologous, to a nucleotide sequence of SEQ ID NO: 2, SEQ ID NO: 6, SEQ ID NO: 17, SEQ ID NO: 19, SEQ ID NO: 21, or SEQ ID NO: 23. It is also preferred that the preferred forms of MR proteins also have one or more of the MR activities described herein.

The MR polypeptide, or a biologically active portion thereof, can be operatively linked to a non-MR polypeptide to form a fusion protein. In preferred embodiments, this fusion protein has an activity which differs from that of the MR protein alone. In other preferred embodiments, this fusion protein transcriptionally, translationally, or posttranslationally regulates one or more metabolic pathways in *C. glutamicum*. In particularly preferred embodiments, integration of this fusion protein into a host cell modulates production of methionine from a cell.

In another aspect, the invention provides methods for screening molecules which modulate the activity of an MR protein, either by interacting with the protein itself or a substrate or binding partner of the MR protein, or by modulating the transcription or translation of an MR nucleic acid molecule of the invention. Another aspect of the invention pertains to a method for producing a fine chemical. This method involves the culturing of a cell containing a vector directing the expression of an MR nucleic acid molecule of the invention, such that a fine chemical is produced. In a preferred embodiment, this method further includes the step of obtaining a cell containing such a vector, in which a cell is transfected with a vector directing the expression of an MR nucleic acid. In another preferred embodiment, this method further includes the step of recovering the fine chemical, e.g., methionine, from the culture. In a particularly preferred embodiment, the cell is from the genus *Corynebacterium* or *Brevibacterium*, or is selected from those strains set forth in Table 1, below.

Another aspect of the invention pertains to methods for modulating production of a molecule from a microorganism. Such methods include contacting the cell with an agent which modulates MR protein activity or MR nucleic acid expression such that a cell associated activity is altered relative to this same activity in the absence of the agent. In a preferred embodiment, the cell is modulated for one or more *C. glutamicum* metabolic pathway regulatory systems, such that the yields or rate of production of a desired fine chemical, e.g., methionine, by this microorganism is improved. The agent which modulates MR protein activity can be an agent which stimulates MR protein activity or MR nucleic acid expression. Examples of agents which stimulate MR protein activity or MR nucleic acid expression include small molecules, active MR proteins, and nucleic acids encoding MR proteins that have been introduced into the cell. Examples of agents which inhibit MR activity or expression include small molecules and antisense MR nucleic acid molecules.

Another aspect of the invention pertains to methods for modulating yields of a desired compound from a cell, involving the introduction of a wild-type or mutant MR gene into a cell, either maintained on a separate plasmid or integrated into the genome of the host cell. If integrated into the genome, such integration can be random, or it can take place by homologous recombination such that the native gene is replaced by the introduced copy, causing the production of the desired compound from the cell to be modulated. In a preferred embodiment, said yields are increased. In another preferred embodiment, said chemical is a fine chemical. In a particularly preferred embodiment, said fine chemical is an amino acid. In especially preferred embodiments, said amino acid is methionine.

DETAILED DESCRIPTION OF THE INVENTION

Figure 1:
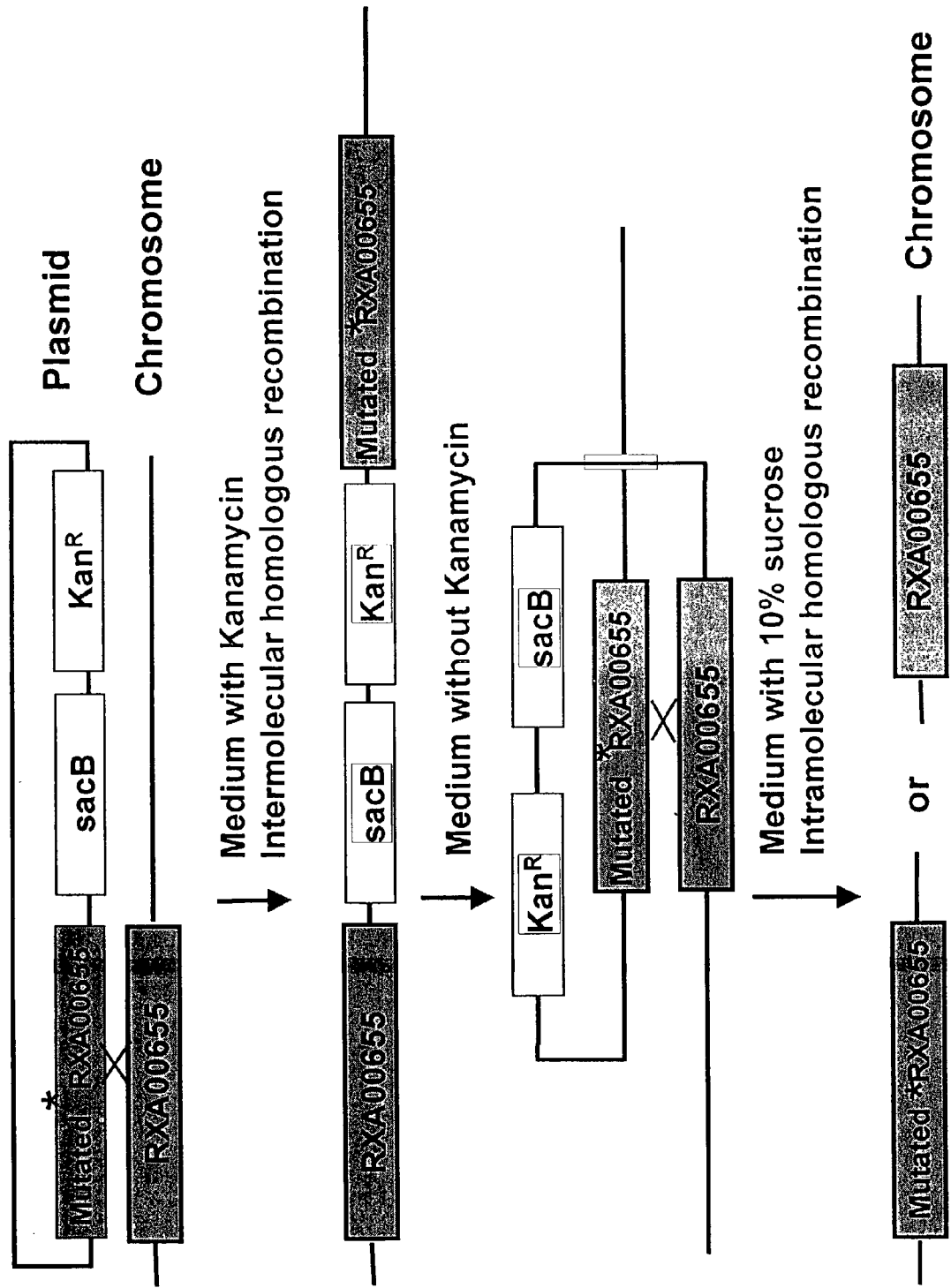
FIG. 1 depicts the principal of a self-cloning technique based on homologous recombination which is used for preparation of a *Corynebacterium glutamicum* strain deficient in the negative regulator of methionine biosynthesis (RXA00655, set forth as SEQ ID NO: 1).

The present invention provides metabolic regulatory (MR) nucleic acid and protein molecules, e.g., RXA00655 and RXN02910 nucleic acid and protein molecules, which are involved in the regulation of metabolism in microorganisms, e.g., *Corynebacterium glutamicum*, including regulation of fine chemical metabolism, e.g., methionine biosynthesis by, e.g., transcriptional regulation of genes, e.g., the metY gene, involved in the methionine biosynthetic pathway, the sulfur reduction pathway, and/or the cysteine biosynthetic pathway.

Accordingly, the present invention features methods based on manipulation of the methionine biosynthetic pathway, the sulfur reduction pathway, and/or the cysteine biosynthetic pathway in a microorganism such that a fine chemical, e.g., a sulfur-containing compound, e.g., methionine, cysteine, and/or other compounds of the methionine biosynthetic pathway, the sulfur reduction pathway, and/or the cysteine biosynthetic pathway are produced.

The term "methionine biosynthetic pathway" includes a pathway involving methionine biosynthetic enzymes (e.g., polypeptides encoded by biosynthetic enzyme-encoding genes), compounds (e.g., precursors, substrates, intermediates or products), cofactors and the like, utilized in the formation or synthesis of methionine. Methionine is an amino acid nutritionally required by mammals. Bacteria synthesize their own methionine from amino acids and biosynthetic intermediates thereof (*Escherichia Coli and Salmonella: Cellular and Molecular Biology*, Neidhardt, Frederick C. Curtiss, Roy III Ingraham, John L. Eds, 2nd ed. 1996, ASM Press and Hwang B J. Yeom H J. Kim Y. Lee H S. (2002) *Journal of Bacteriology* 184(5):1277-86. The term "cysteine biosynthetic pathway" includes a pathway involving cysteine biosynthetic enzymes (e.g., polypeptides encoded by biosynthetic enzyme-encoding genes), compounds (e.g., precursors, substrates, intermediates or products), cofactors and the like, utilized in the formation or synthesis of cysteine. The term "sulfur reduction pathway" includes a pathway involving enzymes which function to metabolize inorganic compounds such as sulfur and derivatives thereof. It has been found that RXA00655 is a negative regulator, e.g., a transcriptional regulator, of fine chemical biosynthesis, e.g., methionine biosynthesis. Accordingly, suppression or inhibition of the expression of the RXA00655 gene or knock-out of the RXA00655 gene leads to increased production of a fine chemical, e.g., methionine, cysteine, and/or other compounds of the methionine biosynthetic pathway, the sulfur reduction pathway, and/or the cysteine biosynthetic pathway, in microorganisms, e.g., *Corynebacterium glutamicum*. Introduction of a mutation which reduces or inhibits expression of the RXA00655 gene or activity of the RXA00655 polypeptide also leads to increased production of a fine chemical, e.g., methionine, cysteine, and/or other compounds of the methionine biosynthetic pathway, the sulfur reduction pathway, and/or the cysteine biosynthetic pathway, in microorganisms, e.g., *Corynebacterium glutamicum.*

It has also been found that RXN02910 is a positive regulator, e.g., a transcriptional regulator, of fine chemical biosynthesis, e.g., methionine biosynthesis. Accordingly, overexpression of the RXN02910 gene leads to increased production of methionine and other compounds of the methionine biosynthetic pathway in microorganisms, e.g., *Corynebacterium glutamicum.* Introduction of a mutation which increases expression of the RXN02910 gene or activity of the RXN02910 polypeptide also leads to increased production of methionine and other compounds of the methionine biosynthetic pathway in microorganisms, e.g., *Corynebacterium glutamicum.*

Furthermore, suppression or inhibition of the expression of RXA00655 or knock-out of the RXA00655 gene in combination with overexpression of the RXN02910 gene in a microorganism also leads to increased production of a fine chemical, e.g., methionine, cysteine, and/or other compounds of the methionine biosynthetic pathway, the sulfur reduction pathway, and/or the cysteine biosynthetic pathway, by the microorganism. Furthermore, culture of microorganisms with suppressed or inhibited expression of RXA00655 or microorganisms with a knock-out of the RXA00655 gene, together with microorganisms which overexpress RXN02910 gene also leads to increased production of a fine chemical, e.g., methionine, cysteine, and/or other compounds of the methionine biosynthetic pathway, the sulfur reduction pathway, and/or the cysteine biosynthetic pathway, by the microorganism.

Accordingly, one aspect the present invention features methods of producing fine chemicals, e.g., methionine or other compounds of the methionine biosynthetic pathway, which include culturing a microorganism which overexpresses a positive regulator of fine chemical biosynthesis, e.g., RXN02910, under conditions such that a fine chemical, e.g., methionine or other compounds of the methionine biosynthetic pathway are produced. A microorganism which overexpresses RXN02910 includes a microorganism which has been manipulated such that RXN02910 is overexpressed.

The term "overexpressed" or "overexpression" includes expression of a gene product (e.g., the RXN02910 gene product) at a level greater than that expressed prior to manipulation of the microorganism or in a comparable microorganism which has not been manipulated. For example, overexpression of a particular gene, e.g., RXN02910, includes expression which is 10%, 20%, 30%, 40%, 50%, 60%, 70%, 80%, 90%, 100%, or greater than expression of the gene by an organism which has not been manipulated to overexpress the particular gene. Ranges and identity values intermediate to the above percentages are encompassed by the present invention. In one embodiment, the microorganism can be genetically manipulated (e.g., genetically engineered) to overexpress a level of gene product greater than that expressed prior to manipulation of the microorganism or in a comparable microorganism which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins).

In another aspect, the present invention features a method of producing a line chemical, e.g., methionine, cysteine, and/or other compounds of the methionine biosynthetic pathway, the sulfur reduction pathway, and/or the cysteine biosynthetic pathway, which includes culturing a microorganism which has suppressed or inhibited expression of a negative regulator of fine chemical biosynthesis, e.g., RXA00655, under conditions such that a fine chemical, e.g., methionine, cysteine, and/or other compounds of the methionine biosynthetic pathway, the sulfur reduction pathway, and/or the cysteine biosynthetic pathway, are produced. A microorganism which has suppressed RXA00655 expression includes a microorganism which has been manipulated such that RXA00655 expression is suppressed or inhibited.

The term "suppression of expression," "inhibition of expression," or "underexpression" includes expression of a gene product (e.g., the RXA00655 gene product or the RXN02910 gene product) at a level lower than that expressed prior to manipulation of the microorganism or in a comparable microorganism which has not been manipulated. In one embodiment, suppression or inhibition of gene expression includes manipulation of a microorganism such that the gene is no longer expressed or is knocked-out. For example, underexpression of a particular gene, e.g., RXA00655, includes expression which is 10%, 20%, 30%, 40%, 50%, 60%, 70%, 80%, 90%, 100%, less than expression of the gene by an organism which has not been manipulated to underexpress the particular gene. Ranges and identity values intermediate to the above percentages are encompassed by the present invention. In one embodiment, the microorganism can be genetically manipulated (e.g., genetically engineered) to express a level of gene product lesser than that expressed prior to manipulation of the microorganism or in a comparable microorganism which has not been manipulated. Genetic manipulation can include, but is not limited to, altering or modifying regulatory sequences or sites associated with expression of a particular gene, modifying the chromosomal location of a particular gene, altering nucleic acid sequences adjacent to a particular gene such as a ribosome binding site, decreasing the copy number of a particular gene, modifying proteins (e.g., regulatory proteins, suppressors, enhancers, transcriptional activators and the like) involved in transcription of a particular gene and/or translation of a particular gene product, use of antisense nucleic acid molecules, knock-out of the target gene, or any other conventional means of deregulating expression of a particular gene routine in the art. A microorganism which is deficient in RXA00655 gene expression or RXN02910 gene expression includes a microorganism which has suppressed or inhibited RXA00655 or RXN02910 expression.

In another aspect, the present invention features a method of producing a fine chemical, e.g., methionine, which includes culturing a microorganism which has increased RXN02910 activity under conditions such that a fine chemical, e.g., methionine, is produced. A "microorganism which has increased RXN02910 activity" includes a microorganism which has been manipulated such that RXN02910 activity is increased.

In yet another aspect, the present invention features a method of producing a fine chemical, e.g., methionine, cysteine, and/or other compounds of the methionine biosynthetic pathway, the sulfur reduction pathway, and/or the cysteine biosynthetic pathway, which includes culturing a microorganism which has decreased RXA00655 activity under conditions such that a fine chemical, e.g., methionine, cysteine, and/or other compounds of the methionine biosynthetic pathway, the sulfur reduction pathway, and/or the cysteine biosynthetic pathway, is produced. A "microorganism which has decreased RXA00655 activity" includes a microorganism which has been manipulated such that RXA00655 activity is inhibited or suppressed.

The term "RXN02910 activity" includes any activity which results in fine chemical biosynthesis, e.g., methionine biosynthesis. RXN02910 activity includes, but is not limited to, positive regulation of the methionine biosynthetic pathway resulting in methionine biosynthesis or biosynthesis of other compounds of the methionine biosynthetic pathway. Positive regulation of the methionine biosynthetic pathway may be by any means, including, but not limited to, transcriptional and translational regulation as well as protein regulation, via, e.g., protein binding. Increased activity includes activity at a level higher than that demonstrated prior to manipulation of the microorganism or in a comparable microorganism which has not been manipulated.

The term "RXA00655 activity" includes any activity which results in fine chemical biosynthesis, e.g., methionine biosynthesis. An example of RXA00655 activity includes, but is not limited to, negative regulation of the methionine biosynthetic pathway, the sulfur reduction pathway, and/or the cysteine biosynthetic pathway as described in *Escherichia Coli and Salmonella: Cellular and Molecular Biology*, Neidhardt, Frederick C. Curtiss, Roy III Ingraham, John L. Eds, 2nd ed. 1996, ASM Press., resulting in decreased methionine biosynthesis, decreased biosynthesis of other compounds of the methionine biosynthetic pathway, the sulfur reduction pathway, or the cysteine biosynthetic pathway. Negative regulation of the methionine biosynthetic pathway, the sulfur reduction pathway, and/or the cysteine biosynthetic pathway may be by any means, including, but not limited to transcriptional and translational regulation as well as protein regulation, via, e.g., protein binding. Decreased or suppressed activity includes activity at a lower higher than that demonstrated prior to manipulation of the microorganism or in a comparable microorganism which has not been manipulated.

The present invention features methods of increasing production of a sulfur-containing compound by a microorganism comprising culturing a microorganism which overexpresses a positive regulator of methionine biosynthesis, e.g., RXN02910, under conditions such that production of the sulfur-containing compound is increased. The present invention also features methods of increasing production of a sulfur-containing compound by a microorganism comprising culturing a microorganism which underexpresses a negative regulator of methionine biosynthesis, e.g., RXA00655, under conditions such that production of the sulfur-containing compound is increased.

The term "sulfur-containing compound" includes any compound which contains sulfur or a derivative thereof. Sulfur-containing compounds include amino acids, including, but not limited to, methionine, cysteine, S-adenosylmethionine, and homocycsteine.

The nucleotide sequence of RXA00655 is set forth herein as SEQ ID NO:1 and the polypeptide sequence of RXA00655 is set forth herein as SEQ ID NO:2. The nucleotide sequence of RXN02910 is set forth herein as SEQ ID NO:5 and the polypeptide sequence of RXN02910 is set forth herein as SEQ ID NO:6. Proteins which are homologous to RXA00655 are set forth herein as SEQ ID NOs:19, 21 and 23. The nucleotide sequences of these RXA00655 homologous proteins are set forth herein as SEQ ID NOs:18, 20 and 22.

SEQ ID NOs: 16 and 17 represent mutated RXN02910 nucleic acid and amino acid sequences, respectively. The RXN02910 molecule depicted in SEQ ID NO: 16 contains a single nucleotide change from a guanine (G) to an adenine (A) at nucleotide residue 556 in the coding region, which results in a change from an aspartic acid (D) to an asparagine (N) at amino acid residue 186 of the encoded protein, set forth as SEQ ID NO: 17. This polymorphism may cause modulation of regulation of fine chemical biosynthesis, e.g., methionine biosynthesis by RXN02910, e.g., decreased methionine biosynthesis.

The molecules of the invention may be utilized in the modulation of production of fine chemicals, e.g., methionine, from microorganisms, such as *C. glutamicum*, either directly (e.g., where modulation of the activity of a methionine biosynthesis regulatory protein has a direct impact on the yield, production, and/or efficiency of production of methionine from that organism), or may have an indirect impact which nonetheless results in an increase in yield, production, and/or efficiency of production of the desired compound (e.g., where modulation of the regulation of a nucleotide biosynthesis protein has an impact on the production of an organic acid or a fatty acid from the bacterium, perhaps due to concomitant regulatory alterations in the biosynthetic or degradation pathways for these chemicals in response to the altered regulation of nucleotide biosynthesis). Aspects of the invention are further explicated below.

I. Fine Chemicals

The term 'fine chemical' is art-recognized and includes molecules produced by an organism which have applications in various industries, such as, but not limited to, the pharmaceutical, agriculture, and cosmetics industries. Such compounds include organic acids, such as tartaric acid, itaconic acid, and diaminopimelic acid, sulfur-containing compounds, both proteinogenic and non-proteinogenic amino acids, purine and pyrimidine bases, nucleosides, and nucleotides (as described e.g. in Kuninaka, A. (1996) Nucleotides and related compounds, p. 561-612, in Biotechnology vol. 6, Rehm et al., eds. VCH: Weinheim, and references contained therein), lipids, both saturated and unsaturated fatty acids (e.g., arachidonic acid), diols (e.g., propane diol, and butane diol), carbohydrates (e.g., hyaluronic acid and trehalose), aromatic compounds (e.g., aromatic amines, vanillin, and indigo), vitamins and cofactors (as described in Ullmann's Encyclopedia of Industrial Chemistry, vol. A27, "Vitamins", p. 443-613 (1996) VCH: Weinheim and references therein; and Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press, (1995)), enzymes, polyketides (Cane et al. (1998) *Science* 282: 63-68), and all other chemicals described in Gutcho (1983) Chemicals by Fermentation, Noyes Data Corporation, ISBN: 0818805086 and references therein. The metabolism and uses of certain of these fine chemicals are further explicated below.

A. Amino Acid Metabolism and Uses

Amino acids comprise the basic structural units of all proteins, and as such are essential for normal cellular functioning in all organisms. The term "amino acid" is art-recognized. The proteinogenic amino acids, of which there are 20 species, serve as structural units for proteins, in which they are linked by peptide bonds, while the nonproteinogenic amino acids (hundreds of which are known) are not normally found in proteins (see Ulmann's Encyclopedia of Industrial Chemistry, vol. A2, p. 57-97 VCH: Weinheim (1985)). Amino acids may be in the D- or L-optical configuration, though L-amino acids are generally the only type found in naturally-occurring proteins. Biosynthetic and degradative pathways of each of the 20 proteinogenic amino acids have been well characterized in both prokaryotic and eukaryotic cells (see, for example, Stryer, L. Biochemistry, $3^{rd}$ edition, pages 578-590 (1988)). The essential amino acids (methionine, histidine, isoleucine, leucine, lysine, phenylalanine, threonine, tryptophan, and valine), so named because they are generally a nutritional requirement due to the complexity of their biosyntheses, are readily converted by simple biosynthetic pathways to the remaining 11 'nonessential' amino acids (alanine, arginine, asparagine, aspartate, cysteine, glutamate, glutamine, glycine, proline, serine, and tyrosine). Higher animals do retain the ability to synthesize some of these amino acids, but the essential amino acids must be supplied from the diet in order for normal protein synthesis to occur.

Aside from their function in protein biosynthesis, many amino acids have been found to have various applications in the food, feed, chemical, cosmetics, agriculture, and pharmaceutical industries. Methionine is an important amino acid in the nutrition not only of humans, but also of other animals.

The biosynthesis of these natural amino acids in organisms capable of producing them, such as bacteria, has been well characterized (for review of bacterial amino acid biosynthesis and regulation thereof, see Umbarger, H. E. (1978) *Ann. Rev. Biochem.* 47: 533-606). Methionine is produced by the conversion of aspartate, which is also the common precursor of lysine, threonine, and isoleucine. Cysteine is produced from serine. Amino acids in excess of the protein synthesis needs of the cell cannot be stored, and are instead degraded to provide intermediates for the major metabolic pathways of the cell (for review see Stryer, L. Biochemistry $3^{rd}$ ed. Ch. 21 "Amino Acid Degradation and the Urea Cycle" p. 495-516 (1988)). Although the cell is able to convert unwanted amino acids into useful metabolic intermediates, amino acid production is costly in terms of energy, precursor molecules, and the enzymes necessary to synthesize them. Thus it is not surprising that amino acid biosynthesis is regulated by feedback inhibition, in which the presence of a particular amino acid serves to slow or entirely stop its own production (for overview of feedback mechanisms in amino acid biosynthetic pathways, see Stryer, L. Biochemistry, $3^{rd}$ ed. Ch. 24: "Biosynthesis of Amino Acids and Heme" p. 575-600 (1988)). Thus, the output of any particular amino acid is limited by the amount of that amino acid present in the cell.

II. Mechanisms of Metabolic Regulation

All living cells have complex catabolic and anabolic metabolic capabilities with many interconnected pathways. In order to maintain a balance between the various parts of this extremely complex metabolic network, the cell employs a finely-tuned regulatory network. By regulating enzyme synthesis and enzyme activity, either independently or simultaneously, the cell is able to control the activity of disparate metabolic pathways to reflect the changing needs of the cell.

The induction or repression of enzyme synthesis may occur at either the level of transcription or translation, or both. Gene expression in prokaryotes is regulated by several mechanisms at the level of transcription (for review see e.g., Lewin, B (1990) Genes IV, Part 3: "Controlling prokaryotic genes by transcription", Oxford University Press: Oxford, p. 213-301, and references therein, and Michal, G. (1999) Biochemical Pathways: An Atlas of Biochemistry and Molecular Biology, John Wiley & Sons). All such known regulatory processes are mediated by additional genes, which themselves respond to external influences of various kinds (e.g., temperature, nutrient availability, or light). Exemplary protein factors which have been implicated in this type of regulation include the transcription factors. These are proteins which bind to DNA, thereby either increasing the expression of a gene (positive regulation, as in the case of e.g. the ara operon from *E. coli*) or decreasing gene expression (negative regulation, as in the case of the lac operon from *E. coli*). These expression-modulating transcription factors can themselves be the subject of regulation. Their activity can, for example, be regulated by the binding of low molecular weight compounds to the DNA-binding protein, thereby stimulating (as in the case of arabinose for the ara operon) or inhibiting (as in the case of the lactose for the lac operon) the binding of these proteins to the appropriate binding site on the DNA (see, for example, Helmann, J. D. and Chamberlin, M. J. (1988) "Structure and function of bacterial sigma factors." *Ann. Rev. Biochem.* 57: 839-872; Adhya, S. (1995) "The lac and gal operons today" and Boos, W. et al., "The maltose system.", both in: Regulation of Gene Expression in *Escherichia coli* (Lin, E. C. C. and Lynch, A. S., eds.) Chapman & Hall: New York, p. 181-200 and 201-229; and Moran, C. P. (1993) "RNA polymerase and transcription factors." in: *Bacillus subtilis* and other gram-positive bacteria, Sonenshein, A. L. et al., eds. ASM: Washington, D.C., p. 653-667.)

Aside from the transcriptional level, protein synthesis is also often regulated at the level of translation. There are multiple mechanisms by which such regulation may occur, including alteration of the ability of the ribosome to bind to one or more mRNAs, binding of the ribosome to the mRNA, the maintenance or removal of mRNA secondary structure, the utilization of common or less common codons for a particular gene, the degree of abundance of one or more tRNAs, and special regulation mechanisms, such as attenuation (see Vellanoweth, R. I. (1993) Translation and its regulation in *Bacillus subtilis* and other gram-positive bacteria, Sonenshein, A. L. et al., eds. ASM: Washington, D.C., p. 699-711 and references cited therein).

Transcriptional and translational regulation may be targeted to a single protein (sequential regulation) or simultaneously to several proteins in different metabolic pathways (coordinate regulation). Often, genes whose expression is coordinately regulated are physically located near one another in the genome, in an operon or regulon. Such up- or down-regulation of gene transcription and translation is governed by the cellular and extracellular levels of various factors, such as substrates (precursor and intermediate molecules used in one or more metabolic pathways), catabolites (molecules produced by biochemical pathways concerned with the production of energy from the breakdown of complex organic molecules such as sugars), and end products (the molecules resulting at the end of a metabolic pathway). Typically, the expression of genes encoding enzymes necessary for the activity of a particular pathway is induced by high levels of substrate molecules for that pathway. Similarly, such gene expression tends to be repressed when there exist high intracellular levels of the end product of the pathway (Snyder, L. and Champness, W. (1997) The Molecular Biology of Bacteria ASM: Washington). Gene expression may also be regulated by other external and internal factors, such as environmental conditions (e.g., heat, oxidative stress, or starvation). These global environmental changes cause alterations in the expression of specialized modulating genes, which directly or indirectly (via additional genes or proteins) trigger the expression of genes by means of binding to DNA and thereby inducing or repressing transcription (see, for example, Lin, E. C. C. and Lynch, A. S., eds. (1995) Regulation of Gene Expression in *Escherichia coli*. Chapman & Hall: New York).

Yet another mechanism by which cellular metabolism may be regulated is at the level of the protein. Such regulation is accomplished either by the activities of other proteins, or by binding of low-molecular-weight components which either impede or enable the normal functioning of the protein. Examples of protein regulation by the binding of low-molecular-weight compounds include the binding of GTP or NAD. The binding of a low-molecular-weight chemical is typically reversible, as is the case with the GTP-binding proteins. These proteins exist in two stages (with bound GTP or GDP), one stage being the activated form of the protein, and one stage being inactive.

Regulation of protein activity by the action of other enzymes typically takes the form of covalent modification of the protein (i.e., phosphorylation of amino acid residues such as histidine or aspartate, or methylation). Such covalent modification is typically reversible, as mediated by an enzyme of the opposite activity. An example of this is the opposite activities of kinases and phosphorylases in protein phosphorylation; protein kinases phosphorylate specific residues on a target protein (e.g., serine or threonine), while protein phosphorylases remove phosphate groups from such proteins. Typically, enzymes which modulate the activity of other proteins are themselves modulated by external stimuli. These stimuli are mediated through proteins which function as sensors. A well known mechanism by which such sensor proteins may mediate these external signals is by dimerization, but others are also known (see, for example, Msadek, T. et al. (1993) "Two-Component Regulatory Systems", in: *Bacillus subtilis* and Other Gram-Positive Bacteria, Sonenshein, A. L. et al., eds., ASM: Washington p. 729-745 and references cited therein).

A thorough understanding of the regulatory networks governing cellular metabolism in microorganisms is critical for the high-yield production of chemicals by fermentation. Control systems for the down-regulation of metabolic pathways could be removed or lessened to improve the synthesis of desired chemicals, and similarly, those for the up-regulation of metabolic pathways for a desired product could be constitutively activated or optimized in activity (As shown in Hirose, Y. and Okada, H. (1979) "Microbial Production of Amino Acids", in: Peppler, H. J. and Perlman, D. (eds.) Microbial Technology $2^{nd}$ ed. Vol. 1, ch. 7 Academic Press: New York.)

III. Elements and Methods of the Invention

The present invention is based, at least in part, on the discovery of novel molecules, referred to herein as MR nucleic acid and protein molecules, e.g., RXA00655 nucleic and protein molecules and RXN02910 nucleic acid and protein molecules, which regulate or modulate one or more metabolic pathways in *C. glutamicum*, e.g., the methionine biosynthesis pathway. RXA00655 is a negative regulator of the methionine biosynthetic pathway, the sulfur reduction pathway, and the cysteine biosynthetic pathway, while RXN02910 is a positive regulator of methionine biosynthesis. Accordingly, the present invention features methods of producing a fine chemical, e.g., methionine, cysteine, and/or other compounds of the methionine biosynthetic pathway, the sulfur reduction pathway, and/or the cysteine biosynthetic pathway and modulating production of a fine chemical, e.g., methionine, cysteine, and/or other compounds of the methionine biosynthetic pathway, the sulfur reduction pathway, and/or the cysteine biosynthetic pathway. Such methods include culturing microorganisms overexpressing the RXN02910 gene product or with increased RXN02910 activity under conditions such a fine chemical, e g., methionine, cysteine, and/or other compounds of the methionine biosynthetic pathway, the sulfur reduction pathway, and/or the cysteine biosynthetic pathway is produced. Such methods also include culturing microorganisms with inhibited expression of the RXA00655 gene product or inhibited RXA00655 activity such that a fine chemical, e.g., methionine, cysteine, and/or other compounds of the methionine biosynthetic pathway, the sulfur reduction pathway, and/or the cysteine biosynthetic pathway, is produced. The present invention also provides methods for producing a fine chemical, e.g. methionine, comprising culturing microorganisms overexpressing the RXN02910 gene product and simultaneously exhibiting an inhibited expression of the RXA00655 gene product or inhibited RXA00655 activity. Furthermore, the present invention also provides methods for producing a fine chemical, e.g., methionine, comprising culturing microorganisms overexpressing the RXN02910 gene product in combination with microorganisms with inhibited expression of the RXA00655 gene product or inhibited RXA00655 activity.

In one embodiment, the MR molecules of the invention transcriptionally, translationally, or posttranslationally regulate a metabolic pathway in *C. glutamicum*. In a preferred embodiment, the activity of the MR molecules of the present invention to regulate one or more *C. glutamicum* metabolic pathways has an impact on the production of a desired fine chemical, e.g., methionine, by this organism. In a particularly preferred embodiment, the MR molecules of the invention are modulated in activity, such that the *C. glutamicum* metabolic pathways which the MR proteins of the invention regulate are modulated in efficiency or output, which either directly or indirectly modulates the yield, production, and/or efficiency of production of a desired fine chemical, e.g., methionine, by *C. glutamicum*.

The language, "MR protein" or "MR polypeptide" includes proteins which transcriptionally, translationally, or posttranslationally regulate a metabolic pathway in *C. glutamicum*. The terms "MR gene" or "MR nucleic acid sequence" include nucleic acid sequences encoding an MR protein, which consist of a coding region and also corresponding untranslated 5' and 3' sequence regions. The terms "production" or "productivity" are art-recognized and include the concentration of the fermentation product (for example, the desired fine chemical) formed within a given time and a given fermentation volume (e.g., kg product per hour per liter). The term "efficiency of production" includes the time required for a particular level of production to be achieved (for example, how long it takes for the cell to attain a particular rate of output of a fine chemical). The term "yield", "product/carbon yield", or "production" is art-recognized and includes the efficiency of the conversion of the carbon source into the product (i.e., methionine). This is generally written as, for example, kg product per kg carbon source. By increasing the yield or production of the compound, the quantity of recovered molecules, or of useful recovered molecules of that compound in a given amount of culture over a given amount of time is increased.

The terms "degradation" or a "degradation pathway" are art-recognized and include the breakdown of a compound, preferably an organic compound, by a cell to degradation products (generally speaking, smaller or less complex molecules) in what may be a multistep and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound. The term, "regulation" is art-recognized and includes the activity of a protein to govern or modulate the activity of another protein. The term, "transcriptional regulation" is art-recognized and includes the activity of a protein to impede or activate the conversion of a DNA encoding a target protein to mRNA. The term, "translational regulation" is art-recognized and includes the activity of a protein to impede or activate the conversion of an mRNA encoding a target protein to a protein molecule. The term, "posttranslational regulation" is art-recognized and includes the activity of a protein to impede or improve the activity of a target protein by covalently modifying the target protein (e.g., by methylation, glucosylation, or phosphorylation, or by binding the target protein).

In another embodiment, the MR molecules of the invention are capable of modulating the production of a desired molecule, such as a fine chemical, e.g., methionine, in a microorganism such as C. glutamicum. Using recombinant genetic techniques, one or more of the regulatory proteins of the invention may be manipulated such that its function is modulated. For example, a biosynthetic enzyme may be improved in efficiency, or its allosteric control region destroyed such that feedback inhibition of production of the compound is prevented. Similarly, a degradative enzyme may be deleted or modified by substitution, deletion, or addition such that its degradative activity is lessened for the desired compound without impairing the viability of the cell. In each case, the overall yield or rate of production of one of these desired fine chemicals may be increased.

It is also possible that such alterations in the protein and nucleotide molecules of the invention may improve the production of fine chemicals, e.g. methionine, in an indirect fashion. The regulatory mechanisms of metabolic pathways in the cell are necessarily intertwined, and the activation of one pathway may lead to the repression or activation of another in a concomitant fashion. Therefore, by modulating the activity of one or more of the proteins of the invention, the production or efficiency of activity of another fine chemical biosynthetic or degradative pathway may be impacted. For example, by decreasing the ability of an MR protein to repress the transcription of a gene encoding a particular amino acid biosynthetic protein, one may concomitantly derepress other amino acid biosynthetic pathways, since these pathways are interrelated. Further, by modifying the MR proteins of the invention, one may uncouple the growth and division of cells from their extracellular surroundings to a certain degree; by impairing an MR protein which normally represses biosynthesis of a nucleotide when the extracellular conditions are suboptimal for growth and cell division such that it now lacks this function, one may permit growth to occur even when the extracellular conditions are poor. This is of particular relevance in large-scale fermentative growth, where conditions within the culture are often suboptimal in terms of temperature, nutrient supply or aeration, but would still support growth and cell division if the cellular regulatory systems for these factors were eliminated.

In one embodiment, the isolated nucleic acid sequences of the invention are contained within the genome of a Corynebacterium glutamicum strain available through the American Type Culture Collection, given designation ATCC 13032. The nucleotide and amino acid sequences of RXA00655 are depicted in SEQ ID NOs: 1, 18, 20, 22 and 2, 19, 21, 23, respectively, and the nucleotide and amino acid sequences of RXN02910 are depicted in SEQ ID NOs: 5 and 6, respectively. SEQ ID NOs: 16 and 17 represent mutated RXN02910 nucleic acid and amino acid sequences, respectively. The RXN02910 molecule depicted in SEQ ID NO: 16 contains a single nucleotide change from a guanine (G) to an adenine (A) at nucleotide residue 556 in the coding region, which results in a change from an aspartic acid (D) to an asparagine (N) at amino acid residue 186 of the encoded protein, set forth as SEQ ID NO: 17. This polymorphism may cause modulation of regulation of methionine biosynthesis or other fine chemicals by RXN02910, e.g., decreased methionine biosynthesis.

The present invention also pertains to proteins which have an amino acid sequence which is substantially homologous to an amino acid sequence of SEQ ID NO: 2, SEQ ID NO: 6, SEQ ID NO: 17, SEQ ID NO: 19, SEQ ID NO: 21, or SEQ ID NO: 23. As used herein, a protein which has an amino acid sequence which is substantially homologous to a selected amino acid sequence is least about 50% homologous to the selected amino acid sequence, e.g., the entire selected amino acid sequence. A protein which has an amino acid sequence which is substantially homologous to a selected amino acid sequence can also be least about 50-60%, preferably at least about 60-70%, and more preferably at least about 70-80%, 80-90%, or 90-95%, and most preferably at least about 90%, 91%, 92%, 93%, 94%, 95%, 96%, 97%, 98%, 99% or more homologous to the selected amino acid sequence.

The MR protein or a biologically active portion or fragment thereof of the invention can transcriptionally, translationally, or posttranslationally regulate a metabolic pathway in C. glutamicum, e.g., the methionine metabolic pathway, or have one or more of the activities set forth herein.

Various aspects of the invention are described in further detail in the following subsections:

A. Isolated Nucleic Acid Molecules

One aspect of the invention pertains to isolated nucleic acid molecules that encode MR polypeptides or biologically active portions thereof, as well as nucleic acid fragments sufficient for use as hybridization probes or primers for the identification or amplification of MR-encoding nucleic acid (e.g., MR DNA). As used herein, the term "nucleic acid molecule" is intended to include DNA molecules (e.g. cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 100 nucleotides of sequence upstream from the 5' end of the coding region and at least about 20 nucleotides of sequence downstream from the 3' end of the coding region of the gene. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MR nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a C. glutamicum cell). Moreover, an "isolated" nucleic acid molecule, such as a DNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO: 1, SEQ ID NO: 5, SEQ ID NO: 16, SEQ ID NO: 18, SEQ ID NO: 20, or SEQ ID NO: 22, or a portion thereof, can be isolated using standard molecular biology techniques and the sequence information provided herein. For example, a MR DNA can be isolated from a C. glutamicum library using all or portion of one of the sequences of SEQ ID NO: 1, SEQ ID NO: 5, SEQ ID NO: 16, SEQ ID NO: 18, SEQ ID NO: 20, or SEQ ID NO: 22 as a hybridization probe and standard hybridization techniques (e.g., as described in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989). Moreover, a nucleic acid molecule encompassing all or a portion of one of the sequences of SEQ ID NO: 1, SEQ ID NO: 5, SEQ ID NO: 16, SEQ ID NO: 18, SEQ ID NO: 20, or SEQ ID NO: 22 can be isolated by the polymerase chain reaction using oligonucleotide primers designed based upon this sequence (e.g., a nucleic acid molecule encompassing all or a portion of one of the sequences of SEQ ID NO: 1, SEQ ID NO: 5, SEQ ID NO: 16, SEQ ID NO: 18, SEQ ID NO: 20, or SEQ ID NO: 22 can be isolated by the polymerase chain reaction using oligonucleotide primers designed based upon this same sequence of SEQ ID NO: 1, SEQ ID NO: 5, SEQ ID NO: 16, SEQ ID NO: 18, SEQ ID NO: 20, or SEQ ID NO: 22). For example, mRNA can be isolated from normal bacterial cells (e.g., by the guanidinium-thiocyanate extraction procedure of Chirgwin et al. (1979) *Biochemistry* 18: 5294-5299) and DNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO: 1, SEQ ID NO: 5, SEQ ID NO: 16, SEQ ID NO: 18, SEQ ID NO: 20, or SEQ ID NO: 22. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an MR nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO: 1, SEQ ID NO: 5, SEQ ID NO: 16, SEQ ID NO: 18, SEQ ID NO: 20, or SEQ ID NO: 22. The sequences of SEQ ID NO: 1, SEQ ID NO: 5, SEQ ID NO: 16, SEQ ID NO: 18, SEQ ID NO: 20, or SEQ ID NO: 22 correspond to the MR DNAs of the invention. This DNA comprises sequences encoding MR proteins (i.e., the "coding region", indicated in each sequence in SEQ ID NO: 1, SEQ ID NO: 5, SEQ ID NO: 16, SEQ ID NO: 18, SEQ ID NO: 20, or SEQ ID NO: 22), as well as 5' untranslated sequences and 3' untranslated sequences, also indicated in SEQ ID NO: 1, SEQ ID NO: 5, SEQ ID NO: 16, SEQ ID NO: 18, SEQ ID NO: 20, or SEQ ID NO: 22. Alternatively, the nucleic acid molecule can comprise only the coding region of any of the sequences in SEQ ID NO: 1, SEQ ID NO: 5, SEQ ID NO: 16, SEQ ID NO: 18, SEQ ID NO: 20, or SEQ ID NO: 22.

In another preferred embodiment, an isolated nucleic acid molecule of the invention comprises a nucleic-acid molecule which is a complement of one of the nucleotide sequences shown in SEQ ID NO: 1, SEQ ID NO: 5, SEQ ID NO: 16, SEQ ID NO: 18, SEQ ID NO: 20, or SEQ ID NO: 22, or a portion thereof. A nucleic acid molecule which is complementary to one of the nucleotide sequences shown in SEQ ID NO: 1, SEQ ID NO: 5, SEQ ID NO: 16, SEQ ID NO: 18, SEQ ID NO: 20, or SEQ ID NO: 22 is one which is sufficiently complementary to one of the nucleotide sequences shown in SEQ ID NO: 1, SEQ ID NO: 5, SEQ ID NO: 16, SEQ ID NO: 18, SEQ ID NO: 20, or SEQ ID NO: 22 such that it can hybridize to one of the nucleotide sequences shown in SEQ ID NO: 1, SEQ ID NO: 5, SEQ ID NO: 16, SEQ ID NO: 18, SEQ ID NO: 20, or SEQ ID NO: 22, thereby forming a stable duplex.

In still another preferred embodiment, an isolated nucleic acid molecule of the invention comprises a nucleotide sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to a nucleotide sequence shown in SEQ ID NO: 1, SEQ ID NO: 5, SEQ ID NO: 16, SEQ ID NO: 18, SEQ ID NO: 20, or SEQ ID NO: 22, or a portion thereof. Ranges and identity values intermediate to the above-recited ranges, (e.g., 70-90% identical or 80-95% identical) are also intended to be encompassed by the present invention. For example, ranges of identity values using a combination of any of the above values recited as upper and/or lower limits are intended to be included. In an additional preferred embodiment, an isolated nucleic acid molecule of the invention comprises a nucleotide sequence which hybridizes, e.g., hybridizes under stringent conditions, to one of the nucleotide sequences shown in SEQ ID NO: 1, SEQ ID NO: 5, SEQ ID NO: 16, SEQ ID NO: 18, SEQ ID NO: 20, or SEQ ID NO: 22, or a portion thereof.

Moreover, the nucleic acid molecule of the invention can comprise only a portion of the coding region of one of the sequences in SEQ ID NO: 1, SEQ ID NO: 5, SEQ ID NO: 16, SEQ ID NO: 18, SEQ ID NO: 20, or SEQ ID NO: 22, for example a fragment which can be used as a probe or primer or a fragment encoding a biologically active portion of an MR protein. The nucleotide sequences determined from the cloning of the MR genes from C. glutamicum allows for the generation of probes and primers designed for use in identifying and/or cloning MR homologues in other cell types and organisms, as well as MR homologues from other Corynebacteria or related species. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO: 1, SEQ ID NO: 5, SEQ ID NO: 16, SEQ ID NO: 18, SEQ ID NO: 20, or SEQ ID NO: 22, an anti-sense sequence of one of the sequences set forth in SEQ ID NO: 1, SEQ ID NO: 5, SEQ ID NO: 16, SEQ ID NO: 18, SEQ ID NO: 20, or SEQ ID NO: 22, or naturally occurring mutants thereof. Primers based on a nucleotide sequence of SEQ ID NO: 1, SEQ ID NO: 5, SEQ ID NO: 16, SEQ ID NO: 18, SEQ ID NO: 20, or SEQ ID NO: 22 can be used in PCR reactions to clone MR homologues. Probes based on the MR nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells which misexpress an MR protein, such as by measuring a level of an MR-encoding nucleic acid in a sample of cells, e.g., detecting MR mRNA levels or determining whether a genomic MR gene has been mutated or deleted.

In one embodiment, the nucleic acid molecule of the invention encodes a protein or portion thereof which includes an amino acid sequence which is sufficiently homologous to an amino acid sequence of SEQ ID NO: 2, SEQ ID NO: 6, SEQ ID NO: 17, SEQ ID NO: 19, SEQ ID NO: 21, or SEQ ID NO: 23 such that the protein or portion thereof maintains the ability to transcriptionally, translationally, or posttranslationally regulate a metabolic pathway, e.g., methionine biosynthetic pathway, the cysteine biosynthetic pathway, or the sulfur reduction pathway, in a microorganism, e.g., C. glutamicum. As used herein, the language "sufficiently homologous" refers to proteins or portions thereof which have amino acid sequences which include a minimum number of identical or equivalent (e.g., an amino acid residue which has a similar side chain as an amino acid residue in one of the sequences of SEQ ID NO: 2, SEQ ID NO: 6, SEQ ID NO: 17, SEQ ID NO: 19, SEQ ID NO: 21, or SEQ ID NO: 23) amino acid residues to an amino acid sequence of SEQ ID NO: 2, SEQ ID NO: 6, SEQ ID NO: 17, SEQ ID NO: 19, SEQ ID NO: 21, or SEQ ID NO: 23 such that the protein or portion thereof is able to transcriptionally, translationally, or posttranslationally regulate a metabolic pathway, e.g., methionine biosynthesis, in C. glutamicum. Protein members of such metabolic pathways, as described herein, may function to regulate the biosynthesis or degradation of one or more fine chemicals. Examples of such activities are also described herein. Thus, "the function of an MR protein" contributes to the overall regulation of one or more fine chemical metabolic pathway, or contributes, either directly or indirectly, to the yield, production, and/or efficiency of production of one or more fine chemicals e.g., methionine.

In another embodiment, the protein is at least about 50-60%, preferably at least about 60-70%, and more preferably at least about 70-80%, 80-90%, 90-95%, and most preferably at least about 96%, 97%, 98%, 99% or more homologous to an entire amino acid sequence of SEQ ID NO: 2, SEQ ID NO: 6, SEQ ID NO: 17, SEQ ID NO: 19, SEQ ID NO: 21, or SEQ ID NO: 23.

As described above, homologous MR proteins, preferably homologous RXA00655 or RXN02910 proteins may be derived from other microorganisms, preferably from prokaryotic microorganisms.

The term "prokaryotic microorganism" is intended to include gram-positive and gram-negative bacteria. Preferably, the term includes all genera and species of the Enterobacteriaceae or Nocardiaceae family, e.g., the Enterobacteriaceae species *Escherichia, Serratia, Proteus, Enterobacter, Klebsiella, Salmonella, Shigella, Edwardsielle, Citrobacter, Morganella, Providencia* and *Yersinia*. Furthermore preferred are all *Pseudomonas, Burkholderia, Nocardia, Acetobacter, Streptomyces, Gluconobacter, Corynebacterium, Brevibacterium, Bacillus, Clostridium, Cyanobacter, Staphylococcus, Aerobacter, Alcaligenes, Rhodococcus* and *Penicillium* species. Most preferred are *Corynebacterium* and *Streptomyces* species such as, e.g., the *Corynebacterium* species exemplified in Table 1, *Corynebacterium diphtheriae, Corynebacterium efficiens* and *Streptomyces coelicolor.*

Examples of homologous MR proteins include the RXA00655 protein from *Corynebacterium diphtheriae*, preferably described by the amino acid sequence comprising the sequence of SEQ ID NO: 19; the RXA00655 protein from *Corynebacterium efficiens* (YS-314 Genbank Accession No. AP005223), preferably described by the amino acid sequence comprising the sequence of SEQ ID NO: 21; and the RXA00655 protein from *Streptomyces coelicolor* (Genbank accession No. NC_003888), preferably described by the amino acid sequence comprising the sequence of SEQ ID NO: 23.

RXN02910 is intended to describe polypeptides encoded by a nucleic acid molecule comprising a nucleic acid molecule selected from the group consisting of: a nucleic acid molecule comprising a nucleotide sequence which is at least 60% identical to the nucleotide sequence of SEQ ID NO: 5 or 16; a nucleic acid molecule comprising a fragment of at least 30 nucleotides of a nucleic acid comprising the nucleotide sequence of SEQ ID NO: 5 or 16; a nucleic acid molecule which encodes a polypeptide comprising an amino acid sequence at least about 60% identical to the amino acid sequence of SEQ ID NO: 6 or 17; and a nucleic acid molecule which encodes a fragment of a polypeptide comprising the amino acid sequence of SEQ ID NO: 6 wherein the fragment comprises at least 10 contiguous amino acid residues of the amino acid sequence of SEQ ID NO: 6 or 17.

RXA00655 is intended to describe polypeptides encoded by a nucleic acid molecule comprising a nucleic acid molecule selected from the group consisting of: a nucleic acid molecule comprising a nucleotide sequence which is at least 60% identical to the nucleotide sequence of SEQ ID NO: 1, 18, 20 or 22; a nucleic acid molecule comprising a fragment of at least 30 nucleotides of a nucleic acid comprising the nucleotide sequence of SEQ ID NO: 1, 18, 20 or 22; a nucleic acid molecule which encodes a polypeptide comprising an amino acid sequence at least about 60% identical to the amino acid sequence of SEQ ID NO: 2, 19, 21 or 23; and a nucleic acid molecule which encodes a fragment of a polypeptide comprising the amino acid sequence of SEQ ID NO: 2, 19, 21 or 23 wherein the fragment comprises at least 10 contiguous amino acid residues of the amino acid sequence of SEQ ID NO: 2, 19, 21 or 23.

Portions of proteins encoded by the MR nucleic acid molecules of the invention are preferably biologically active portions of one of the MR proteins. As used herein, the term "biologically active portion of an MR protein" is intended to include a portion, e.g., a domain/motif, of an MR protein that transcriptionally, translationally, or posttranslationally regulates a metabolic pathway, e.g., methionine biosynthetic pathway, the cysteine biosynthetic pathway, or the sulfur reduction pathway, in a microorganism, e.g., C. glutamicum, or has an activity as set forth herein. To determine whether an MR protein or a biologically active portion thereof can transcriptionally, translationally, or posttranslationally regulate a metabolic pathway, e.g., methionine biosynthetic pathway, the cysteine biosynthetic pathway, or the sulfur reduction pathway, in a microorganism, e.g., C. glutamicum, an assay of enzymatic activity may be performed. Such assay methods are well known to those of ordinary skill in the art, as detailed in Example 8 of the Exemplification.

Additional nucleic acid fragments encoding biologically active portions of an MR protein can be prepared by isolating a portion of one of the sequences in SEQ ID NO: 2, SEQ ID NO: 6, SEQ ID NO: 17, SEQ ID NO: 19, SEQ ID NO: 21, or SEQ ID NO: 23, expressing the encoded portion of the MR protein or peptide (e.g., by recombinant expression in vitro) and assessing the activity of the encoded portion of the MR protein or peptide.

The invention further encompasses nucleic acid molecules that differ from one of the nucleotide sequences shown in SEQ ID NO: 1, SEQ ID NO: 5, SEQ ID NO: 16, SEQ ID NO: 18, SEQ ID NO: 20, or SEQ ID NO: 22 (and portions thereof) due to degeneracy of the genetic code and thus encode the same MR protein as that encoded by the nucleotide sequences shown in SEQ ID NO: 1, SEQ ID NO: 5, SEQ ID NO: 16, SEQ ID NO: 18, SEQ ID NO: 20, or SEQ ID NO: 22. In another embodiment, an isolated nucleic acid molecule of the invention has a nucleotide sequence encoding a protein having an amino acid sequence shown in SEQ ID NO: 2, SEQ ID NO: 6, SEQ ID NO: 17, SEQ ID NO: 19, SEQ ID NO: 21, or SEQ ID NO: 23. In a still further embodiment, the nucleic acid molecule of the invention encodes a full length *C. glutamicum* protein which is substantially homologous to an amino acid sequence of SEQ ID NO: 2, SEQ ID NO: 6, SEQ ID NO: 17, SEQ ID NO: 19, SEQ ID NO: 21, or SEQ ID NO: 23 (encoded by an open reading frame shown in SEQ ID NO: 1, SEQ ID NO: 5, SEQ ID NO: 16, SEQ ID NO: 18, SEQ ID NO: 20, or SEQ ID NO: 22).

In one embodiment, the invention includes nucleotide and amino acid sequences having a percent identity to a nucleotide or amino acid sequence of the invention which is greater than that of a sequence of the prior art (e.g., a Genbank sequence (or the protein encoded by such a sequence). One of ordinary skill in the art would be able to calculate the lower threshold of percent identity for any given sequence of the invention by examining the GAP-calculated percent identity scores for each of the three top hits for a given sequence, and by subtracting the highest GAP-calculated percent identity from 100 percent. One of ordinary skill in the art will also appreciate that nucleic acid and amino acid sequences having percent identities greater than the lower threshold so calculated (e.g., at least 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical) are also encompassed by the invention.

In addition to the *C. glutamicum* MR nucleotide sequences shown in SEQ ID NO: 1, SEQ ID NO: 5, SEQ ID NO: 16, SEQ ID NO: 18, SEQ ID NO: 20, or SEQ ID NO: 22, it will be appreciated by those of ordinary skill in the art that DNA sequence polymorphisms that lead to changes in the amino acid sequences of MR proteins may exist within a population (e.g., the *C. glutamicum* population). Such genetic polymorphism in the MR gene may exist among individuals within a population due to natural variation. As used herein, the terms "gene" and "recombinant gene" refer to nucleic acid molecules comprising an open reading frame encoding an MR protein, preferably a *C. glutamicum* MR protein. Such natural variations can typically result in 1-5% variance in the nucleotide sequence of the MR gene. Any and all such nucleotide variations and resulting amino acid polymorphisms in MR that are the result of natural variation and that do not alter the functional activity of MR proteins are intended to be within the scope of the invention.

Nucleic acid molecules corresponding to natural variants and non-*C. glutamicum* homologues of the *C. glutamicum* MR DNA of the invention can be isolated based on their homology to the *C. glutamicum* MR nucleic acid disclosed herein using the *C. glutamicum* DNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of SEQ ID NO: 1, SEQ ID NO: 5, SEQ ID NO: 16, SEQ ID NO: 18, SEQ ID NO: 20, or SEQ ID NO: 22. In other embodiments, the nucleic acid is at least 15, 20, 25, 30, 40, 50, 60, 70, 80, 90, 100, 110, 120, 130, 140, 150, 160, 170, 180, 190, 200, 210, 220, 225 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those of ordinary skill in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of SEQ ID NO: 1, SEQ ID NO: 5, SEQ ID NO: 16, SEQ ID NO: 18, SEQ ID NO: 20, or SEQ ID NO: 22 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *C. glutamicum* MR protein.

In addition to naturally-occurring variants of the MR sequence that may exist in the population, one of ordinary skill in the art will further appreciate that changes can be introduced by mutation into a nucleotide sequence of SEQ ID NO: 1, SEQ ID NO: 5, SEQ ID NO: 16, SEQ ID NO: 18, SEQ ID NO: 20, or SEQ ID NO: 22, thereby leading to changes in the amino acid sequence of the encoded MR protein, without altering the functional ability of the MR protein. For example, nucleotide substitutions leading to amino acid substitutions at "non-essential" amino acid residues can be made in a sequence of SEQ ID NO: 1, SEQ ID NO: 5, SEQ ID NO: 16, SEQ ID NO: 18, SEQ ID NO: 20, or SEQ ID NO: 22. A "non-essential" amino acid residue is a residue that can be altered from the wild-type sequence of one of the MR proteins (SEQ ID NO: 2, SEQ ID NO: 6, SEQ ID NO: 17, SEQ ID NO: 19, SEQ ID NO: 21, or SEQ ID NO: 23) without altering the activity of said MR protein, whereas an "essential" amino acid residue is required for MR protein activity. Other amino acid residues, however, (e.g., those that are not conserved or only semi-conserved in the domain having MR activity) may not be essential for activity and thus are likely to be amenable to alteration without altering MR activity.

Accordingly, another aspect of the invention pertains to nucleic acid molecules encoding MR proteins that contain changes in amino acid residues that are not essential for MR activity. Such MR proteins differ in amino acid sequence from a sequence contained in SEQ ID NO: 2, SEQ ID NO: 6, SEQ ID NO: 17, SEQ ID NO: 19, SEQ ID NO: 21, or SEQ ID NO: 23 yet retain at least one of the MR activities described herein. In one embodiment, the isolated nucleic acid molecule comprises a nucleotide sequence encoding a protein, wherein the protein comprises an amino acid sequence at least about 50% homologous to an amino acid sequence of SEQ ID NO: 2, SEQ ID NO: 6, SEQ ID NO: 17, SEQ ID NO: 19, SEQ ID NO: 21, or SEQ ID NO: 23 and is capable of transcriptionally, translationally, or posttranslationally regulating a metabolic pathway in *C. glutamicum*, or has one or more activities set forth herein. Preferably, the protein encoded by the nucleic acid molecule is at least about 50-60% homologous to one of the sequences in SEQ ID NO: 2, SEQ ID NO: 6, SEQ ID NO: 17, SEQ ID NO: 19, SEQ ID NO: 21, or SEQ ID NO: 23, more preferably at least about 60-70% homologous to one of the sequences in SEQ ID NO: 2, SEQ ID NO: 6, SEQ ID NO: 17, SEQ ID NO: 19, SEQ ID NO: 21, or SEQ ID NO: 23, even more preferably at least about 70-80%, 80-90% homologous to one of the sequences in SEQ ID NO: 2, SEQ ID NO: 6, SEQ ID NO: 17, SEQ ID NO: 19, SEQ ID NO: 21, or SEQ ID NO: 23, and most preferably at least about 90%, 91%, 92%, 93%, 94%, 95%, 96%, 97%, 98%, or 99% homologous to one of the sequences in SEQ ID NO: 2, SEQ ID NO: 6, SEQ ID NO: 17, SEQ ID NO: 19, SEQ ID NO: 21, or SEQ ID NO: 23.

To determine the percent homology of two amino acid sequences (e.g., one of the sequences of SEQ ID NO: 2, SEQ ID NO: 6, SEQ ID NO: 17, SEQ ID NO: 19, SEQ ID NO: 21, or SEQ ID NO: 23 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of SEQ ID NO: 2, SEQ ID NO: 6, SEQ ID NO: 17, SEQ ID NO: 19, SEQ ID NO: 21, or SEQ ID NO: 23) is occupied by the same amino acid residue or nucleotide as the corresponding position in the other sequence (e.g., a mutant form of the sequence selected from SEQ ID NO: 2, SEQ ID NO: 6, SEQ ID NO: 17, SEQ ID NO: 19, SEQ ID NO: 21, or SEQ ID NO: 23), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

An isolated nucleic acid molecule encoding an MR protein homologous to a protein sequence of SEQ ID NO: 2, SEQ ID NO: 6, SEQ ID NO: 17, SEQ ID NO: 19, SEQ ID NO: 21, or SEQ ID NO: 23 can be created by introducing one or more nucleotide substitutions, additions or deletions into a nucleotide sequence of SEQ ID NO: 1, SEQ ID NO: 5, SEQ ID NO: 16, SEQ ID NO: 18, SEQ ID NO: 20, or SEQ ID NO: 22 such that one or more amino acid substitutions, additions or deletions are introduced into the encoded protein. Mutations can be introduced into one of the sequences of SEQ ID NO: 1, SEQ ID NO: 5, SEQ ID NO: 16, SEQ ID NO: 18, SEQ ID NO: 20, or SEQ ID NO: 22 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an MR protein is preferably replaced with another amino acid residue from the same side chain family. Alternatively, in another embodiment, mutations can be introduced randomly along all or part of an MR coding sequence, such as by saturation mutagenesis, and the resultant mutants can be screened for an MR activity described herein to identify mutants that retain MR activity. Following mutagenesis of one of the sequences of SEQ ID NO: 1, SEQ ID NO: 5, SEQ ID NO: 16, SEQ ID NO: 18, SEQ ID NO: 20, or SEQ ID NO: 22, the encoded protein can be expressed recombinantly and the activity of the protein can be determined using, for example, assays described herein (see Example 8 of the Exemplification).

In addition to the nucleic acid molecules encoding MR proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded DNA molecule or complementary to an mRNA sequence. Accordingly, an antisense nucleic acid can hydrogen bond to a sense nucleic acid. The antisense nucleic acid can be complementary to an entire MR coding strand, or to only a portion thereof. In one embodiment, an antisense nucleic acid molecule is antisense to a "coding region" of the coding strand of a nucleotide sequence encoding an MR protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding MR. The term "noncoding region" refers to 5' and 3' sequences which flank the coding region that are not translated into amino acids (i.e., also referred to as 5' and 3' untranslated regions).

Given the coding strand sequences encoding MR molecules disclosed herein (e.g., the sequences set forth in SEQ ID NO: 1, SEQ ID NO: 5, SEQ ID NO: 16, SEQ ID NO: 18, SEQ ID NO: 20, or SEQ ID NO: 22), antisense nucleic acids of the invention can be designed according to the rules of Watson and Crick base pairing. The antisense nucleic acid molecule can be complementary to the entire coding region of MR mRNA, but more preferably is an oligonucleotide which is antisense to only a portion of the coding or noncoding region of MR mRNA. For example, the antisense oligonucleotide can be complementary to the region surrounding the translation start site of MR mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding an MR protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonycleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave MR mRNA transcripts to thereby inhibit translation of MR mRNA. A ribozyme having specificity for an MR-encoding nucleic acid can be designed based upon the nucleotide sequence of an MR DNA disclosed herein (i.e., SEQ ID NO: 1, SEQ ID NO: 5, SEQ ID NO: 16, SEQ ID NO: 18, SEQ ID NO: 20, or SEQ ID NO: 22). For example, a derivative of a Tetrahymena L-19 IVS RNA can be constructed in which the nucleotide sequence of the active site is complementary to the nucleotide sequence to be cleaved in an MR-encoding mRNA. See, e.g., Cech et al. U.S. Pat. No. 4,987,071 and Cech et al. U.S. Pat. No. 5,116,742. Alternatively, MR mRNA can be used to select a catalytic RNA having a specific ribonuclease activity from a pool of RNA molecules. See, e.g., Bartel, D. and Szostak, J. W. (1993) *Science* 261:1411-1418.

Alternatively, MR gene expression can be inhibited by targeting nucleotide sequences complementary to the regulatory region of an MR nucleotide sequence (e.g., an MR promoter and/or enhancers) to form triple helical structures that prevent transcription of an MR gene in target cells. See generally, Helene, C. (1991) *Anticancer Drug Des.* 6(6):569-84; Helene, C. et al. (1992) *Ann. N.Y Acad. Sci.* 660:27-36; and Maher, L. J. (1992) *Bioassays* 14(12):807-15.

In still another embodiment, additional or alternative methods known to the person skilled in the art can be used to modulate, e.g., suppress or increase, expression from a gene (e.g., a gene coding for a negative regulator of methionine biosynthesis) or to modulate, e.g., increase or suppress or inhibit activity of the corresponding gene product.

One method which may be used is the expression of a dominant-negative variant of the gene product (e.g., a gene coding for a negative regulator of methionine biosynthesis) to suppress activity of, e.g., a negative regulator of methionine biosynthesis.

A negative regulator of methionine biosynthesis (e.g., RXA00655 as exemplified by SEQ ID NO: 1) is preferably a transcriptional regulator. Transcriptional regulators are known to exists as dimers which bind to opposite parts of the DNA to structures that might contain repeating sequences in so called dyad symmetry. The activity of DNA binding is determined within the amino acid sequence of the transcriptional regulator. Examples of the structural basis of the dimeric binding of such transcriptional regulators can be found in Schumacher M. A. and Brennan R. G. (2002) *Molecular Microbiology.* 45:885-93. For example, expression of different alleles of the same protein in one cell by producing hetero-dimeric proteins consisting of an unmutated and of a mutated allele of a regulatory protein confer a dominant negative phenotype for such an organism. Examples of methods for constructing a mutant dominant negative repressor protein in organisms also expressing unmutated alleles of the same gene can be found in *Journal of Molecular Biology* (2002) 322(2):311-24, and in *Journal of Biological Chemistry* (1994). 269(11):8246-54. For example, the DNA-binding domain of said negative regulator of methionine biosynthesis may be inactivated. In another embodiment, mRNA stabilisation and destabilisation can be used as a method to either increase or decrease the life time of a given mRNA molecule. Methods to influence the life time of a given mRNA can be found in Smolke C. D. and Keasling J. D. (2002) *Biotechnology & Bioengineering.* 78(4):412-24, in Smolke C. D. et al. (2001) *Metabolic Engineering* 3(4):313-21, and in Carrier T. A. and Keasling J. D. (1999) *Biotechnology Progress* 15(1):58-64. Another method which may be used to modulate expression of a gene includes expression of DNA-binding proteins increasing or blocking or reducing expression from the gene, e.g., a gene coding for a regulatory protein of methionine biosynthesis.

Blocking or reducing expression from the gene, e.g., a gene coding for a negative regulatory protein of methionine biosynthesis can be realized by utilizing specific DNA-binding proteins, e.g., of the zinc-finger protein class of transcription factors. Said factors may be directed to e.g., regulatory regions of the gene to be suppressed. Utilization of said factors allows suppression of expression without altering the corresponding gene sequence. Methods are known to the person skilled in the art to construct artificial DNA-binding factors capable of binding to a specific target sequence. Increasing gene expression, e.g., coding for a positive regulator of methionine biosynthesis, can be realized by using the above described artificial DNA-binding factors by fusing them to a transcription activation domain, thereby creating an artificial initiator of transcription. (Dreier B et al. (2001) *J Biol Chem* 276(31):29466-78; Dreier B et al. (2000) *J Mol Biol* 303(4):489-502; Beerli R R et al. (2000) *Proc Natl Acad Sci USA* 97 (4):1495-1500; Beerli R R et al. (2000) *J Biol*

*Chem* 275(42):32617-32627; Segal D J and Barbas C F 3rd. (2000) *Curr Opin Chem Biol* 4(1):34-39; Kang J S and Kim J S (2000) *J Biol Chem* 275(12):8742-8748; Beerli R R et al. (1998) *Proc Natl Acad Sci USA* 95(25):14628-14633; Kim J S et al. (1997) *Proc Natl Acad Sci USA* 94(8):3616-3620; Klug A (1999) *J Mol Biol* 293(2):215-218; Tsai S Y et al. (1998) *Adv Drug Deliv Rev* 30(1-3):23-31; Mapp A K et al. (2000) *Proc Natl Acad Sci USA* 97(8):3930-3935; Sharrocks A D et al. (1997) *Int J Biochem Cell Biol* 29(12):1371-1387; Zhang L et al. (2000) *J Biol Chem* 275(43):33850-33860). Suppression of gene expression can also be realized by using customized low-molecular weight synthetic compounds, e.g., of the polyamide type (Dervan P B and Bürli R W (1999) *Current Opinion in Chemical Biology* 3:688-693; Gottesfeld J M et al. (2000) *Gene Expr* 9(1-2):77-91). These compounds can be adopted on a rational basis to any specific DNA target sequence allowing suppression or, if the compound is used in fusion with a transcription activation domain, initiation of gene expression. Methods are known to the person skilled in the art to construct the artificial DNA-binding factors capable of binding to a specific target sequence (Bremer R E et al. (2001) *Bioorg Med Chem.* 9(8):2093-103; Ansari A. Z. et al. (2001) *Chem Biol.* 8(6):583-92; Gottesfeld J. M. et al. (2001) *J Mol Biol.* 309(3):615-29; Wurtz N. R. et al. (2001) *Org Lett* 3(8):1201-3; Wang C. C. et al. (2001) *Bioorg Med Chem* 9(3):653-7; Urbach A. R. and Dervan P. B. (2001) *Proc Natl Acad Sci USA* 98(8):4343-8; Chiang S. Y. et al. (2000) *J Biol Chem.* 275(32):24246-54). In another embodiment, expression of protein-binding factors activating or blocking or reducing expression or activity of the gene coding for a regulatory protein of methionine biosynthesis may be utilized.

Protein-binding factors suitable for binding regulators of methionine biosynthesis and thereby suppressing activity may be based on RNA such as, e.g. aptamers (Famulok M und Mayer G (1999) *Curr Top Microbiol Immunol* 243:123-36), antibodies, antibody fragments, or single-chain antibodies. Methods for construction and utilization of these protein-binding factors are known to the person skilled in the art.

B. Recombinant Expression Vectors and Host Cells

Another aspect of the invention pertains to vectors, preferably expression vectors, containing a nucleic acid encoding an MR protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990) and in Vasicova P. Patek M. Nesvera J. Sahm H. Eikmanns B. (1999) *Journal of Bacteriology* 181(19):6188-91, in Patek M. et al. (1996) *Microbiology* 142:1297-309, and in Mateos et al. (1994) *Journal of Bacteriology* 176:7362-71. Regulatory sequences include those which direct constitutive expression of a nucleotide sequence in many types of host cell and those which direct expression of the nucleotide sequence only in certain host cells. Preferred regulatory sequences are, for example, promoters such as cos-, tac-, trp-, tet-, trp-tet-, lpp-, lac-, lpp-lac-, lacI$^q$-, T7-, T5-, T3-, gal-, trc-, ara-, SP6-, arny, SPO2, $\lambda$-P$_R$- or $\lambda$ P$_L$, which are used preferably in bacteria. Additional regulatory sequences are, for example, promoters from yeasts and fungi, such as ADC1, MFα, AC, P-60, CYC1, GAPDH, TEF, rp28, ADH, promoters from plants such as CaMV/35S, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., MR proteins, mutant forms of MR proteins, fusion proteins, etc.).

The recombinant expression vectors of the invention can be designed for expression of MR proteins in prokaryotic or eukaryotic cells. For example, MR genes can be expressed in bacterial cells such as *C. glutamicum*, insect cells (using baculovirus expression vectors), yeast and other fungal cells (see Romanos, M. A. et al. (1992) "Foreign gene expression in yeast: a review", *Yeast* 8: 423-488; van den Hondel, C. A. M. J. J. et al. (1991) "Heterologous gene expression in filamentous fungi" in: More Gene Manipulations in Fungi, J. W. Bennet & L. L. Lasure, eds., p. 396-428: Academic Press: San Diego; and van den Hondel, C. A. M. J. J. & Punt, P. J. (1991) "Gene transfer systems and vector development for filamentous fungi, in: Applied Molecular Genetics of Fungi, Peberdy, J. F. et al., eds., p. 1-28, Cambridge University Press: Cambridge), algae and multicellular plant cells (see Schmidt, R. and Willmitzer, L. (1988) High efficiency *Agrobacterium tumefaciens*—mediated transformation of *Arabidopsis thaliana* leaf and cotyledon explants" *Plant Cell Rep.*: 583-586), or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the MR protein is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant MR protein unfused to GST can be recovered by cleavage of the fusion protein with thrombin.

Examples of suitable inducible non-fusion *E. coli* expression vectors include pTrc (Amann et al., (1988) *Gene* 69:301-315) pLG338, pACYC184, pBR322, pUC18, pUC19, pKC30, pRep4, pHS1, pHS2, pPLc236, pMBL24, pLG200, pUR290, pIN-III113-B1, λgt11, pBdC1, and pET 11d (Studier et al., *Gene Expression Technology: Methods in Enzymology* 185, Academic Press, San Diego, Calif. (1990) 60-89; and Pouwels et al., eds. (1985) Cloning Vectors. Elsevier: N.Y. ISBN 0 444 904018). Other examples for inducible *E. coli C. glutamicum* shuttle expression vectors can be found in Eikmanns B. J., et al. (1991) *Gene* 102:93-8. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter. For transformation of other varieties of bacteria, appropriate vectors may be selected. For example, the plasmids pIJ100, pIJ364, pIJ702 and pIJ361 are known to be useful in transforming Streptomyces, while plasmids pUB110, pC194, or pBD214 are suited for transformation of Bacillus species. Several plasmids of use in the transfer of genetic information into Corynebacterium include pHM1519, pBL1, pSA77, or pAJ667 (Pouwels et al., eds. (1985) Cloning Vectors. Elsevier: N.Y. IBSN 0 444 904018). One strategy to maximize recombinant protein expression is to express the protein in a host bacteria with an impaired capacity to proteolytically cleave the recombinant protein (Gottesman, S., *Gene Expression Technology. Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al. (1992) *Nucleic Acids Res.* 20:2111-2118). Such alteration of nucleic acid sequences of the invention can be carried out by standard DNA synthesis techniques.

In another embodiment, the MR protein expression vector is a yeast expression vector. Examples of vectors for expression in yeast *S. cerevisiae* include pYepSec1 (Baldari, et al., (1987) *Embo J.* 6:229-234), 2μ, pAG-1, Yep6, Yep13, pEMBLYe23, pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge, and Pouwels et al., eds. (1985) Cloning Vectors. Elsevier: N.Y. (IBSN 0 444 904018).

Alternatively, the MR proteins of the invention can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In another embodiment, the MR proteins of the invention may be expressed in unicellular plant cells (such as algae) or in plant cells from higher plants (e.g., the spermatophytes, such as crop plants). Examples of plant expression vectors include those detailed in: Becker, D., Kemper, E., Schell, J. and Masterson, R. (1992) "New plant binary vectors with selectable markers located proximal to the left border", *Plant Mol. Biol.* 20: 1195-1197; and Bevan, M. W. (1984) "Binary Agrobacterium vectors for plant transformation", *Nucl. Acid. Res.* 12: 8711-8721, and include pLGV23, pGHlac+, pBIN19, pAK2004, and pDH51 (Pouwels et al., eds. (1985) Cloning Vectors. Elsevier: N.Y. IBSN 0 444 904018).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning. A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *PNAS* 86:5473-5477), pancreas-specific promoters (Edlund et al.

(1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the a-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MR mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis; *Reviews—Trends in Genetics, Vol.* 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an MR protein can be expressed in bacterial cells such as *C. glutamicum*, insect cells, yeast or mammalian cells (such as Chinese hamster ovary cells (CHO) or COS cells). Other suitable host cells are known to one of ordinary skill in the art. Microorganisms related to *Corynebacterium glutamicum* which may be conveniently used as host cells for the nucleic acid and protein molecules of the invention are set forth in Table 1, below.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an MR protein or can be introduced on a separate vector. Cells stably transfected with the introduced nucleic acid can be identified by, for example, drug selection (e.g., cells that have incorporated the selectable marker gene will survive, while the other cells die).

For transformation of microorganisms, it is known that, depending upon the expression vector and transformation technique used, only a small fraction of cells may incorporate the foreign DNA either with an episomal localisation or into their genome by processes involving recombination. In order to identify and select these transformants, a gene that encodes a selectable marker (e.g., resistance to antibiotics) is generally introduced into the host cells along with the gene of interest. Preferred selectable markers include those which confer resistance to drugs, such as kanamycin, tetracyclin, bleomycin, chloramphenicol, lincomycin. Nucleic acid encoding a selectable marker can be introduced into a host cell on the same vector as that encoding an MR protein or can be introduced on a separate vector. Cells transformed with the introduced nucleic acid can be identified by, for example, drug selection (e.g., cells that have incorporated the selectable marker gene will survive, while the other cells die).

Examples for antibiotic resistance genes that can be used in *C. glutamicum* can be found in, for example, Tauch A. et al. (1992) *Applied Microbiology & Biotechnology* 36(6):759-62; Eikmanns B. J. et al. (1991) *Gene* 102(1):93-8; Yoshihama M. et al. (1985) *Journal of Bacteriology* 162(2):591-7; Tauch A. et al. (1998) *Plasmid* 40(2):126-39; Cadenas R F et al. (1991) *Gene* 98(1):117-21.

To create a homologous recombinant microorganism, a vector is prepared which contains at least a portion of an MR gene into which a deletion, addition or substitution has been introduced to thereby alter, e.g., functionally disrupt, the MR gene. Preferably, this MR gene is a *Corynebacterium glutamicum* MR gene, but it can be a homologue from a related bacterium or even from a mammalian, yeast, or insect source. In a preferred embodiment, the vector is designed such that, upon homologous recombination, the endogenous MR gene is functionally disrupted (i.e., no longer encodes a functional protein; also referred to as a "knock-out" vector). Alternatively, the vector can be designed such that, upon homologous recombination, the endogenous MR gene is mutated or otherwise altered but still encodes functional protein (e.g., the upstream regulatory region can be altered to thereby alter the expression of the endogenous MR protein). In the homologous recombination vector, the altered portion of the MR gene is flanked at its 5' and 3' ends by additional nucleic acid of the MR gene to allow for homologous recombination to occur between the exogenous MR gene carried by the vector and an endogenous MR gene in a microorganism. The additional flanking MR nucleic acid is of sufficient length for successful homologous recombination with the endogenous gene. Typically, the flanking DNA should have lengths between 100 basepairs and a few kilobases (both at the 5' and 3' ends) are included in the vector (see e.g., Thomas, K. R., and Capecchi, M. R. (1987) *Cell* 51: 503 for a description of homologous recombination vectors). In addition, methods are known in which another selection can be used to construct chromosomal recombinations in which the selection marker is retrieved by a method of positive selection (Schafer A. et al. (1994) *Gene* 145(1):69-73) The vector is introduced into a microorganism (e.g., by electroporation) and cells in which the introduced MR gene has homologously recombined with the endogenous MR gene are selected, using art-known techniques.

In another embodiment, recombinant microorganisms can be produced which contain selected systems which allow for regulated expression of the introduced gene. For example, inclusion of an MR gene on a vector placing it under control of the lac operon permits expression of the MR gene only in the presence of IPTG. Such regulatory systems are well known in the art and are described in e.g., Eikmanns B. J. et al. (1991) *Gene* 102:93-8.

In another embodiment, an endogenous MR gene in a host cell is disrupted (e.g., by homologous recombination or other genetic means known in the art) such that expression of its protein product does not occur. In another embodiment, an endogenous or introduced MR gene in a host cell has been altered by one or more point mutations, deletions, or inversions, but still encodes a functional MR protein. In still another embodiment, one or more of the regulatory regions (e.g., a promoter, repressor, or inducer) of an MR gene in a microorganism has been altered (e.g., by deletion, truncation, inversion, or point mutation) such that the expression of the MR gene is modulated. One of ordinary skill in the art will appreciate that host cells containing more than one of the described MR gene and protein modifications may be readily produced using the methods of the invention, and are meant to be included in the present invention.

A host cell of the invention, such as a prokaryotic or eukaryotic host cell in culture, can be used to produce (i.e. express) an MR protein. Accordingly, the invention further provides methods for producing MR proteins using the host cells of the invention. In one embodiment, the method comprises culturing the host cell of invention (into which a recombinant expression vector encoding an MR protein has been introduced, or into which genome has been introduced a gene encoding a wild-type or altered MR protein) in a suitable medium until MR protein is produced. In another embodiment, the method further comprises isolating MR proteins from the medium or the host cell.

C. Isolated MR Proteins

Another aspect of the invention pertains to isolated MR proteins, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of MR protein in which the protein is separated from cellular components of the cells in which it is naturally or recombinantly produced. In one embodiment, the language "substantially free of cellular material" includes preparations of MR protein having less than about 30% (by dry weight) of non-MR protein (also referred to herein as a "contaminating protein"), more preferably less than about 20% of non-MR protein, still more preferably less than about 10% of non-MR protein, and most preferably less than about 5% non-MR protein. When the MR protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of MR protein in which the protein is separated from chemical precursors or other chemicals which are involved in the synthesis of the protein. In one embodiment, the language "substantially free of chemical precursors or other chemicals" includes preparations of MR protein having less than about 30% (by dry weight) of chemical precursors or non-MR chemicals, more preferably less than about 20% chemical precursors or non-MR chemicals, still more preferably less than about 10% chemical precursors or non-MR chemicals, and most preferably less than about 5% chemical precursors or non-MR chemicals. In preferred embodiments, isolated proteins or biologically active portions thereof lack contaminating proteins from the same organism from which the MR protein is derived. Typically, such proteins are produced by recombinant expression of, for example, a *C. glutamicum* MR protein in a microorganism such as *C. glutamicum*.

An isolated MR protein or a portion thereof of the invention can transcriptionally, translationally, or posttranslationally regulate a metabolic pathway in *C. glutamicum*, or has one or more of the activities set forth herein. In preferred embodiments, the protein or portion thereof comprises an amino acid sequence which is sufficiently homologous to an amino acid sequence of SEQ ID NO: 2, SEQ ID NO: 6, SEQ ID NO: 17, SEQ ID NO: 19, SEQ ID NO: 21, or SEQ ID NO: 23 such that the protein or portion thereof maintains the ability to transcriptionally, translationally, or posttranslationally regulate a metabolic pathway in *C. glutamicum*. The portion of the protein is preferably a biologically active portion as described herein. In another preferred embodiment, an MR protein of the invention has an amino acid sequence shown in SEQ ID NO: 2, SEQ ID NO: 6, SEQ ID NO: 17, SEQ ID NO: 19, SEQ ID NO: 21, or SEQ ID NO: 23. In yet another preferred embodiment, the MR protein has an amino acid sequence which is encoded by a nucleotide sequence which hybridizes, e.g., hybridizes under stringent conditions, to a nucleotide sequence of SEQ ID NO: 1, SEQ ID NO: 5, SEQ ID NO: 16, SEQ ID NO: 18, SEQ ID NO: 20, or SEQ ID NO: 22. In still another preferred embodiment, the MR protein has an amino acid sequence which is encoded by a nucleotide sequence that is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to one of the nucleic acid sequences of SEQ ID NO: 1, SEQ ID NO: 5, SEQ ID NO: 16, SEQ ID NO: 18, SEQ ID NO: 20, or SEQ ID NO: 22, or a portion thereof. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. The preferred MR proteins of the present invention also preferably possess at least one of the MR activities described herein. For example, a preferred MR protein of the present invention includes an amino acid sequence encoded by a nucleotide sequence which hybridizes, e.g., hybridizes under stringent conditions, to a nucleotide sequence of SEQ ID NO: 1, SEQ ID NO: 5, SEQ ID NO: 16, SEQ ID NO: 18, SEQ ID NO: 20, or SEQ ID NO: 22, and which can transcriptionally, translationally, or posttranslationally regulate a metabolic pathway in *C. glutamicum*, or which has one or more of the activities set forth herein.

In other embodiments, the MR protein is substantially homologous to an amino acid sequence of SEQ ID NO: 2, SEQ ID NO: 6, SEQ ID NO: 17, SEQ ID NO: 19, SEQ ID NO: 21, or SEQ ID NO: 23 and retains the functional activity of the protein of one of the sequences of SEQ ID NO: 2, SEQ ID NO: 6, SEQ ID NO: 17, SEQ ID NO: 19, SEQ ID NO: 21, or SEQ ID NO: 23 yet differs in amino acid sequence due to natural variation or mutagenesis, as described in detail in subsection I above. Accordingly, in another embodiment, the MR protein is a protein which comprises an amino acid sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, 91%, 92%, 93%, 94%, and even more preferably at least about 95%, 96%, 97%, 98%, 99% or more homologous to an entire amino acid sequence of SEQ ID NO: 2, SEQ ID NO: 6, SEQ ID NO: 17, SEQ ID NO: 19, SEQ ID NO: 21, or SEQ ID NO: 23 and which has at least one of the MR activities described herein. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. In another embodiment, the invention pertains to a full length *C. glutamicum* protein which is substantially homologous to an entire amino acid sequence of SEQ ID NO: 2, SEQ ID NO: 6, SEQ ID NO: 17, SEQ ID NO: 19, SEQ ID NO: 21, or SEQ ID NO: 23.

Biologically active portions of an MR protein include peptides comprising amino acid sequences derived from the amino acid sequence of an MR protein, e.g., the an amino acid sequence shown in SEQ ID NO: 2, SEQ ID NO: 6, SEQ ID NO: 17, SEQ ID NO: 19, SEQ ID NO: 21, or SEQ ID NO: 23 or the amino acid sequence of a protein homologous to an MR protein, which include fewer amino acids than a full length MR protein or the full length protein which is homologous to an MR protein, and exhibit at least one activity of an MR protein. Typically, biologically active portions (peptides, e.g., peptides which are, for example, 5, 10, 15, 20, 30, 35, 36, 37, 38, 39, 40, 50, 100, 150, 200 or more amino acids in length) comprise a domain or motif with at least one activity of an MR protein. Moreover, other biologically active portions, in which other regions of the protein are deleted, can be prepared by recombinant techniques and evaluated for one or more of the activities described herein. Preferably, the biologically active portions of an MR protein include one or more selected domains/motifs or portions thereof having biological activity.

MR proteins are preferably produced by recombinant DNA techniques. For example, a nucleic acid molecule encoding the protein is cloned into an expression vector (as described above), the expression vector is introduced into a host cell (as described above) and the MR protein is expressed in the host cell. The MR protein can then be isolated from the cells by an appropriate purification scheme using standard protein purification techniques. Alternative to recombinant expression, an MR protein, polypeptide, or peptide can be synthesized chemically using standard peptide synthesis techniques. Moreover, native MR protein can be isolated from cells (e.g., endothelial cells), for example using an anti-MR antibody, which can be produced by standard techniques utilizing an MR protein or fragment thereof of this invention.

The invention also provides MR chimeric or fusion proteins. As used herein, an MR "chimeric protein" or "fusion protein" comprises an MR polypeptide operatively linked to a non-MR polypeptide. An "MR polypeptide" refers to a polypeptide having an amino acid sequence corresponding to an MR protein, whereas a "non-MR polypeptide" refers to a polypeptide having an amino acid sequence corresponding to a protein which is not substantially homologous to the MR protein, e.g., a protein which is different from the MR protein and which is derived from the same or a different organism. Within the fusion protein, the term "operatively linked" is intended to indicate that the MR polypeptide and the non-MR polypeptide are fused in-frame to each other. The non-MR polypeptide can be fused to the N-terminus or C-terminus of the MR polypeptide. For example, in one embodiment the fusion protein is a GST-MR fusion protein in which the MR sequences are fused to the C-terminus of the GST sequences. Such fusion proteins can facilitate the purification of recombinant MR proteins. In another embodiment, the fusion protein is an MR protein containing a heterologous signal sequence at its N-terminus. In certain host cells (e.g., mammalian host cells), expression and/or secretion of an MR protein can be increased through use of a heterologous signal sequence.

Preferably, an MR chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An MR-encoding nucleic acid can be cloned into such an expression vector such that the fusion moiety is linked in-frame to the MR protein. flomologues of the MR protein can be generated by mutagenesis, e.g., discrete point mutation or truncation of the MR protein. As used herein, the term "homologue" refers to a variant form of the MR protein which acts as an agonist or antagonist of the activity of the MR protein. An agonist of the MR protein can retain substantially the same, or a subset, of the biological activities of the MR protein. An antagonist of the MR protein can inhibit one or more of the activities of the naturally occurring form of the MR protein, by, for example, competitively binding to a downstream or upstream member of the MR regulatory cascade which includes the MR protein. Thus, the *C. glutamicum* MR protein and homologues thereof of the present invention may modulate the activity of one or more metabolic pathways which MR proteins regulate in this microorganism.

In an alternative embodiment, homologues of the MR protein can be identified by screening combinatorial libraries of mutants, e.g., truncation mutants, of the MR protein for MR protein agonist or antagonist activity. In one embodiment, a variegated library of MR variants is generated by combinatorial mutagenesis at the nucleic acid level and is encoded by a variegated gene library. A variegated library of MR variants can be produced by, for example, enzymatically ligating a mixture of synthetic oligonucleotides into gene sequences such that a degenerate set of potential MR sequences is expressible as individual polypeptides, or alternatively, as a set of larger fusion proteins (e.g., for phage display) containing the set of MR sequences therein. There are a variety of methods which can be used to produce libraries of potential MR homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MR sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the MR protein coding can be used to generate a variegated population of MR fragments for screening and subsequent selection of homologues of an MR protein. In one embodiment, a library of coding sequence fragments can be generated by treating a double stranded PCR fragment of an MR coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the MR protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MR homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify MR homologues (Arkin and Yourvan (1992) *PNAS* 89:7811-7815; Delgrave et al. (1993) *Protein Engineering* 6(3):327-331).

In another embodiment, cell based assays can be exploited to analyze a variegated MR library, using methods well known in the art.

D. Uses and Methods of the Invention

The nucleic acid molecules, proteins, protein homologues, fusion proteins, primers, vectors, and host cells described herein can be used in one or more of the following methods: modulation of cellular production of a desired compound, such as a fine chemical, e.g., methionine; identification of *C. glutamicum* and related organisms; mapping of genomes of organisms related to *C. glutamicum*; identification and localization of *C. glutamicum* sequences of interest; evolutionary studies; determination of MR protein regions required for function; modulation of an MR protein activity; and modulation of the activity of one or more metabolic pathways.

The MR nucleic acid molecules of the invention have a variety of uses. Manipulation of the MR nucleic acid molecules of the invention, e.g., suppressing or increasing expression or activity of the nucleic acid or protein molecules, respectively, results in the modulation of methionine biosynthesis. For example, a *Corynebacterium glutamicum* strain which overexpresses or has increased expression of RXN02910, a positive regulator of methionine biosynthesis, displays a significant increase in the production of methionine or other compounds of the methionine biosynthetic pathway. Furthermore, a *Corynebacterium glutamicum* strain which is deficient in or has suppressed expression of RXA00655, a negative regulator of methionine biosynthesis, also displays a significant increase in the production of methionine or other compounds of the methionine biosynthetic pathway.

Furthermore, manipulation of the MR nucleic acid molecules of the invention may lead to production of MR proteins having functional differences from the wild-type MR proteins. These proteins may be improved in efficiency or activity, may be present in greater numbers in the cell than is usual, or may be decreased in efficiency or activity.

The invention provides methods for screening molecules which modulate the activity of an MR protein, either by interacting with the protein itself or a substrate or binding partner of the MR protein, or by modulating the transcription or translation of an MR nucleic acid molecule of the invention. In such methods, a microorganism expressing one or more MR proteins of the invention is contacted with one or more test compounds, and the effect of each test compound on the activity or level of expression of the MR protein is assessed.

Such changes in activity may directly modulate the yield, production, and/or efficiency of production of one or more fine chemicals from *C. glutamicum*, e.g., methionine. For example, by optimizing the activity of an MR protein, e.g., a positive regulator of methionine biosynthesis, e.g., RXN02910, which activates the transcription or translation of a gene encoding a biosynthetic protein for a desired fine chemical, or by impairing or abrogating the activity of an MR protein, e.g., a negative regulator of methionine biosynthesis, e.g., RXA00655, which represses the transcription or translation of such a gene, one may also increase the activity or rate of activity of that biosynthetic pathway. Similarly, by altering the activity of an MR protein such that it constitutively post-translationally inactivates a protein involved in a degradation pathway for a desired fine chemical, or by altering the activity of an MR protein such that it constitutively represses the transcription or translation of such a gene, one may increase the yield and/or rate of production of the fine chemical from the cell, due to decreased degradation of the compound.

Further, by modulating the activity of one or more MR proteins, one may indirectly stimulate the production or improve the rate of production of one or more fine chemicals from the cell due to the interrelatedness of disparate metabolic pathways. For example, by increasing the yield, production, and/or efficiency of production by activating the expression of one or more lysine biosynthetic enzymes, one may concomitantly increase the expression of other compounds, such as other amino acids, which the cell would naturally require in greater quantities when lysine is required in greater quantities. Also, regulation of metabolism throughout the cell may be altered such that the cell is better able to grow or replicate under the environmental conditions of fermentative culture (where nutrient and oxygen supplies may be poor and possibly toxic waste products in the environment may be at high levels). For example, by mutagenizing an MR protein which represses the synthesis of molecules necessary for cell membrane production in response to high levels of waste products in the extracellular medium (in order to block cell growth and division in suboptimal growth conditions) such that it no longer is able to repress such synthesis, one may increase the growth and multiplication of the cell in cultures even when the growth conditions are suboptimal. Such enhanced growth or viability should also increase the yields and/or rate of production of a desired fine chemical from fermentative culture, due to the relatively greater number of cells producing this compound in the culture.

The aforementioned mutagenesis strategies for MR proteins to result in increased yields of a fine chemical, e.g., methionine, from *C. glutamicum* are not meant to be limiting; variations on these strategies will be readily apparent to one of ordinary skill in the art. Using such strategies, and incorporating the mechanisms disclosed herein, the nucleic acid and protein molecules of the invention may be utilized to generate *C. glutamicum* or related strains of bacteria expressing mutated MR nucleic acid and protein molecules such that the yield and/or efficiency of production of a desired compound is improved. This desired compound may be any natural product of *C. glutamicum*, which includes the final products of biosynthesis pathways and intermediates of naturally-occurring metabolic pathways, as well as molecules which do not naturally occur in the metabolism of *C. glutamicum*, but which are produced by a *C. glutamicum* strain of the invention.

The MR molecules of the invention may also be used to identify an organism as being *Corynebacterium glutamicum* or a close relative thereof. Also, they may be used to identify the presence of *C. glutamicum* or a relative thereof in a mixed population of microorganisms. The invention provides the nucleic acid sequences of a number of *C. glutamicum* genes; by probing the extracted genomic DNA of a culture of a unique or mixed population of microorganisms under stringent conditions with a probe spanning a region of a *C. glutamicum* gene which is unique to this organism, one can ascertain whether this organism is present.

Although *Corynebacterium glutamicum* itself is nonpathogenic, it is related to pathogenic species, such as *Corynebacterium diphtheriae*. *Corynebacterium diphtheriae* is the causative agent of diphtheria, a rapidly developing, acute, febrile infection which involves both local and systemic pathology. In this disease, a local lesion develops in the upper respiratory tract and involves necrotic injury to epithelial cells; the bacilli secrete toxin which is disseminated through this lesion to distal susceptible tissues of the body. Degenerative changes brought about by the inhibition of protein synthesis in these tissues, which include heart, muscle, peripheral nerves, adrenals, kidneys, liver and spleen, result in the systemic pathology of the disease. Diphtheria continues to have high incidence in many parts of the world, including Africa, Asia, Eastern Europe and the independent states of the former Soviet Union. An ongoing epidemic of diphtheria in the latter two regions has resulted in at least 5,000 deaths since 1990.

In one embodiment, the invention provides a method of identifying the presence or activity of *Cornyebacterium diphtheriae* in a subject. This method includes detection of one or more of the nucleic acid or amino acid sequences of the invention (e.g., the sequences set forth in SEQ ID NO: 1, SEQ ID NO: 5, SEQ ID NO: 16, SEQ ID NO: 18, SEQ ID NO: 20, or SEQ ID NO: 22 or SEQ ID NO: 2, SEQ ID NO: 6, SEQ ID NO: 17, SEQ ID NO: 19, SEQ ID NO: 21, or SEQ ID NO: 23) in a subject, thereby detecting the presence or activity of *Corynebacterium diphtheriae* in the subject. *C. glutamicum* and *C. diphtheriae* are related bacteria, and many of the nucleic acid and protein molecules in *C. glutamicum* are homologous to *C. diphtheriae* nucleic acid and protein molecules, and can therefore be used to detect *C. diphtheriae* in a subject.

The nucleic acid and protein molecules of the invention may also serve as markers for specific regions of the genome. This has utility not only in the mapping of the genome, but also for functional studies of *C. glutamicum* proteins. For example, to identify the region of the genome to which a particular *C. glutamicum* DNA-binding protein binds, the *C. glutamicum* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *C. glutamicum*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related bacteria, such as *Brevibacterium lactofermentum*.

The MR nucleic acid molecules of the invention are also useful for evolutionary and protein structural studies. The metabolic processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

This invention is further illustrated by the following examples which should not be construed as limiting. The contents of all references, Figure, patent applications, patents, published patent applications, Tables, and the Sequence Listing cited throughout this application are hereby incorporated by reference.

EXAMPLES

Example 1

Preparation of Total Genomic DNA of Corynebacterium Glutamicum ATCC 13032

A culture of *Corynebacterium glutamicum* (ATCC 13032) was grown overnight at 30° C. with vigorous shaking in BHI medium (Difco). The cells were harvested by centrifugation, the supernatant was discarded and the cells were resuspended in 5 ml buffer-I (5% of the original volume of the culture—all indicated volumes have been calculated for 100 ml of culture volume). Composition of buffer-I: 140.34 g/l sucrose, 2.46 g/l $MgSO_4 \times 7H_2O$, 10 ml/l $KH_2PO_4$ solution (100 g/l, adjusted to pH 6.7 with KOH), 50 ml/l M12 concentrate (10 g/l $(NH_4)_2SO_4$, 1 g/l NaCl, 2 g/l $MgSO_4 \times 7H_2O$, 0.2 g/l $CaCl_2$, 0.5 g/l yeast extract (Difco), 10 ml/l trace-elements-mix (200 mg/l $FeSO_4 \times H_2O$, 10 mg/l $ZnSO_4 \times 7 H_2O$, 3 mg/l $MnCl_2 \times 4 H_2O$, 30 mg/l $H_3BO_3$ 20 mg/l $CoCl_2 \times 6 H_2O$, 1 mg/l $NiCl_2 \times 6 H_2O$, 3 mg/l $Na_2MoO_4 \times 2 H_2O$, 500 mg/l complexing agent (EDTA or critic acid), 100 ml/l vitamins-mix (0.2 mg/l biotin, 0.2 mg/l folic acid, 20 mg/l p-amino benzoic acid, 20 mg/l riboflavin, 40 mg/l ca-panthothenate, 140 mg/l nicotinic acid, 40 mg/l pyridoxole hydrochloride, 200 mg/l myo-inositol). Lysozyme was added to the suspension to a final concentration of 2.5 mg/ml. After an approximately 4 h incubation at 37° C., the cell wall was degraded and the resulting protoplasts are harvested by centrifugation. The pellet was washed once with 5 ml buffer-I and once with 5 ml TE-buffer (10 mM Tris-HCl, 1 mM EDTA, pH 8). The pellet was resuspended in 4 ml TE-buffer and 0.5 ml SDS solution (10%) and 0.5 ml NaCl solution (5 M) are added. After adding of proteinase K to a final concentration of 200 µg/ml, the suspension is incubated for ca. 18 h at 37° C. The DNA was purified by extraction with phenol, phenol-chloroform-isoamylalcohol and chloroform-isoamylalcohol using standard procedures. Then, the DNA was precipitated by adding 1/50 volume of 3 M sodium acetate and 2 volumes of ethanol, followed by a 30 min incubation at −20° C. and a 30 min centrifugation at 12,000 rpm in a high speed centrifuge using a SS34 rotor (Sorvall). The DNA was dissolved in 1 ml TE-buffer containing 20 µg/ml RNaseA and dialysed at 4° C. against 1000 ml TE-buffer for at least 3 hours. During this time, the buffer was exchanged 3 times. To aliquots of 0.4 ml of the dialysed DNA solution, 0.4 ml of 2 M LiCl and 0.8 ml of ethanol are added. After a 30 min incubation at −20° C., the DNA was collected by centrifugation (13,000 rpm, Biofuge Fresco, Heraeus, Hanau, Germany). The DNA pellet was dissolved in TE-buffer. DNA prepared by this procedure could be used for all purposes, including southern blotting or construction of genomic libraries.

Example 2

Construction of Genomic Libraries in *Escherichia Coli* of *Corynebacterium Glutamicum* ATCC13032

Using DNA prepared as described in Example 1, cosmid and plasmid libraries were constructed according to known and well established methods (see e.g., Sambrook, J. et al. (1989) "Molecular Cloning: A Laboratory Manual", Cold Spring Harbor Laboratory Press, or Ausubel, F. M. et al. (1994) "Current Protocols in Molecular Biology", John Wiley & Sons.)

Any plasmid or cosmid could be used. Of particular use were the plasmids pBR322 (Sutcliffe, J. G. (1979) *Proc. Natl. Acad. Sci. USA,* 75:3737-3741); pACYC177 (Change & Cohen (1978) *J. Bacteriol* 134:1141-1156), plasmids of the pBS series (pBSSK+, pBSSK− and others; Stratagene, LaJolla, USA), or cosmids as SuperCos1 (Stratagene, LaJolla, USA) or Lorist6 (Gibson, T. J., Rosenthal A. and Waterson, R. H. (1987) *Gene* 53:283-286. Gene libraries specifically for use in *C. glutamicum* may be constructed using plasmid pSL109 (Lee, H.-S. and A. J. Sinskey (1994) *J. Microbiol. Biotechnol.* 4: 256-263).

Example 3

DNA Sequencing and Computational Functional Analysis

Genomic libraries as described in Example 2 were used for DNA sequencing according to standard methods, in particular by the chain termination method using ABI377 sequencing machines (see e.g., Fleischman, R. D. et al. (1995) "Whole-genome Random Sequencing and Assembly of Haemophilus Influenzae Rd., *Science,* 269:496-512). Sequencing primers with the following nucleotide sequences were used:

5'-GGAAACAGTATGACCATG-3' (SEQ ID NO: 24) or
5'-GTAAAACGACGGCCAGT-3' (SEQ ID NO: 25).

Example 4

In Vivo Mutagenesis

In vivo mutagenesis of *Corynebacterium glutamicum* can be performed by passage of plasmid (or other vector) DNA through *E. coli* or other microorganisms (e.g. *Bacillus spp.* or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and Salmonella, p. 2277-2294, ASM: Washington.) Such strains are well known to one of ordinary skill in the art. The use of such strains is illustrated, for example, in Greener, A. and Callahan, M. (1994) *Strategies* 7: 32-34.

Example 5

DNA Transfer Between *Escherichia Coli* and *Corynebacterium Glutamicum*

Several *Corynebacterium* and *Brevibacterium* species contain endogenous plasmids (as e.g., pHM1519 or pBL1) which replicate autonomously (for review see, e.g., Martin, J. F. et al. (1987) *Biotechnology,* 5:137-146). Shuttle vectors for *Escherichia coli* and *Corynebacterium glutamicum* can be readily constructed by using standard vectors for *E. coli* (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons) to which a origin or replication for and a suitable marker from *Corynebacterium glutamicum* is added. Such origins of replication are preferably taken from endogenous plasmids isolated from *Corynebacterium* and *Brevibacterium* species. Of particular use as transformation markers for these species are genes for kanamycin resistance (such as those derived from the Tn5 or Tn903 transposons) or chloramphenicol (Winnacker, E. L. (1987) "From Genes to Clones—Introduction to Gene Technology, VCH, Weinheim). There are numerous examples in the literature of the construction of a wide variety of shuttle vectors which replicate in both *E. coli* and *C. glutamicum*, and which can be used for several purposes, including gene over-expression (for reference, see e.g., Yoshihama, M. et al. (1985) *J. Bacteriol.* 162:591-597, Martin J. F. et al. (1987) Biotechnology, 5:137-146 and Eikmanns, B. J. et al. (1991) *Gene,* 102:93-98).

Using standard methods, it is possible to clone a gene of interest into one of the shuttle vectors described above and to introduce such a hybrid vectors into strains of *Corynebacterium glutamicum*. Transformation of *C. glutamicum* can be achieved by protoplast transformation (Kastsumata, R. et al. (1984) *J. Bacteriol.* 159306-311), electroporation (Liebl, E. et al. (1989) *FEMS Microbiol. Letters,* 53:399-303) and in cases where special vectors are used, also by conjugation (as described e.g. in Schäfer, A et al. (1990) *J. Bacteriol.* 172: 1663-1666). It is also possible to transfer the shuttle vectors for *C. glutamicum* to *E. coli* by preparing plasmid DNA from *C. glutamicum* (using standard methods well-known in the art) and transforming it into *E. coli*. This transformation step can be performed using standard methods, but it is advantageous to use an Mcr-deficient *E. coli* strain, such as NM522 (Gough & Murray (1983) *J. Mol. Biol.* 166:1-19).

Genes may be overexpressed in *C. glutamicum* strains using plasmids which comprise pCG1 (U.S. Pat. No. 4,617,267) or fragments thereof, and optionally the gene for kanamycin resistance from TN903 (Grindley, N. D. and Joyce, C. M. (1980) *Proc. Natl. Acad. Sci. USA* 77(12): 7176-7180). In addition, genes may be overexpressed in *C. glutamicum* strains using plasmid pSL109 (Lee, H.-S. and A. J. Sinskey (1994) *J. Microbiol. Biotechnol.* 4: 256-263).

Aside from the use of replicative plasmids, gene overexpression can also be achieved by integration into the genome. Genomic integration in *C. glutamicum* or other *Corynebacterium* or *Brevibacterium* species may be accomplished by well-known methods, such as homologous recombination with genomic region(s), restriction endonuclease mediated integration (REMI) (see, e.g., DE Patent 19823834), or through the use of transposons. It is also possible to modulate the activity of a gene of interest by modifying the regulatory regions (e.g., a promoter, a repressor, and/or an enhancer) by sequence modification, insertion, or deletion using site-directed methods (such as homologous recombination) or methods based on random events (such as transposon mutagenesis or REMI). Nucleic acid sequences which function as transcriptional terminators may also be inserted 3' to the coding region of one or more genes of the invention; such terminators are well-known in the art and are described, for example, in Winnacker, E. L. (1987) From Genes to Clones—Introduction to Gene Technology. VCH: Weinheim.

Example 6

Assessment of the Expression of the Mutant Protein

Observations of the activity of a mutated protein in a transformed host cell rely on the fact that the mutant protein is expressed in a similar fashion and in a similar quantity to that of the wild-type protein. A useful method to ascertain the level of transcription of the mutant gene (an indicator of the amount of mRNA available for translation to the gene product) is to perform a Northern blot (for reference see, for example, Ausubel et al. (1988) Current Protocols in Molecular Biology, Wiley: N.Y.), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information is evidence of the degree of transcription of the mutant gene. Total cellular RNA can be prepared from *Corynebacterium glutamicum* by several methods, all well-known in the art, such as that described in Bormann, E. R. et al. (1992) *Mol. Microbiol.* 6: 317-326.

To assess the presence or relative quantity of protein translated from this mRNA, standard techniques, such as a Western blot, may be employed (see, for example, Ausubel et al. (1988) Current Protocols in Molecular Biology, Wiley: N.Y.). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label which may be readily detected. The presence and quantity of label observed indicates the presence and quantity of the desired mutant protein present in the cell.

Example 7

Growth of *Corynebacterium Glutamicum*—Media and Culture Conditions

Corynebacteria are cultured in synthetic or natural growth media. A number of different growth media for Corynebacteria are both well-known and readily available (Lieb et al. (1989) *Appl. Microbiol. Biotechnol.*, 32:205-210; von der Osten et al. (1998) *Biotechnology Letters*, 11:11-16; Patent DE 4,120,867; Liebl (1992) "The Genus Corynebacterium, in: The Procaryotes, Volume II, Balows, A. et al., eds. Springer-Verlag). These media consist of one or more carbon sources, nitrogen sources, inorganic salts, vitamins and trace elements. Preferred carbon sources are sugars, such as mono-, di, or polysaccharides. For example, glucose, fructose, mannose, galactose, ribose, sorbose, ribulose, lactose, maltose, sucrose, raffinose, starch or cellulose serve as very good carbon sources. It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates urea, amino acids or complex nitrogen sources like corn steep liquor, soy bean flour, soy bean protein, yeast extract, meat extract and others.

Inorganic salt compounds which may be included in the media include the chloride-, phosphorous- or sulfate-salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamin, folic acid, nicotinic acid, pantothenate and pyridoxin. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (eds. P. M. Rhodes, P. F. Stanbury, IRL Press (1997) pp. 53-73, ISBN 0 19 963577 3). It is also possible to select growth media from commercial suppliers, like standard 1 (Merck) or BHI (brain heart infusion, DIFCO) or others.

All medium components are sterilized, either by heat (20 minutes at 1.5 bar and 121° C.) or by sterile filtration. The components can either be sterilized together or, if necessary, separately. All media components can be present at the beginning of growth, or they can optionally be added continuously or batchwise.

Culture conditions are defined separately for each experiment. The temperature should be in a range between 15° C. and 45° C. The temperature can be kept constant or can be altered during the experiment. The pH of the medium should be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of NaOH or NH$_4$OH during growth. If complex medium components such as yeast extract are utilized, the necessity for additional buffers may be reduced, due to the fact that many complex compounds have high buffer capacities. If a fermentor is utilized for culturing the micro-organisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml shake flasks are used, filled with 10% (by volume) of the required growth medium. The flasks should be shaken on a rotary shaker (amplitude 25 mm) using a speed-range of 100-300 rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested. The medium is inoculated to an OD$_{600}$ of O0.5-1.5 using cells grown on agar plates, such as CM plates (10 g/l glucose, 2.5 g/l NaCl, 2 g/l urea, 10 g/l polypeptone, 5 g/l yeast extract, 5 g/l meat extract, 22 g/l NaCl, 2 g/l urea, 10 g/l polypeptone, 5 g/l yeast extract, 5 g/l meat extract, 22 g/l agar, pH 6.8 with 2M NaOH) that had been incubated at 30° C. Inoculation of the media is accomplished by either introduction of a saline suspension of *C. glutamicum* cells from CM plates or addition of a liquid preculture of this bacterium.

Example 8

In Vitro Analysis of the Function of Mutant Proteins

The determination of activities and kinetic parameters of enzymes is well established in the art. Experiments to determine the activity of any given altered enzyme must be tailored to the specific activity of the wild-type enzyme, which is well within the ability of one of ordinary skill in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: N.Y.; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3$^{rd}$ ed. Academic Press: New York; Bisswanger, H., (1994) Enzymkinetik, 2$^{nd}$ ed. VCH: Weinheim (ISBN 3527300325); Bergmeyer, H. U., Bergmeyer, J., Graβl, M., eds. (1983-1986) Methods of Enzymatic Analysis, 3$^{rd}$ ed., vol. I-XII, Verlag Chemie: Weinheim; and Ullmann's Encyclopedia of Industrial Chemistry (1987) vol. A9, "Enzymes". VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895-3904 and references cited therein). Reporter gene test systems are well known and established for applications in both pro- and eukaryotic cells, using enzymes such as beta-galactosidase, green fluorescent protein, and several others.

The determination of activity of membrane-transport proteins can be performed according to techniques such as those described in Gennis, R. B. (1989) "Pores, Channels and Transporters", in Biomembranes, Molecular Structure and Function, Springer: Heidelberg, p. 85-137; 199-234; and 270-322.

Example 9

Analysis of Impact of Mutant Protein on the Production of the Desired Product

The effect of the genetic modification in *C. glutamicum* on production of a desired compound (such as an amino acid) can be assessed by growing the modified microorganism under suitable conditions (such as those described above) and analyzing the medium and/or the cellular component for increased production of the desired product (i.e., an amino acid). Such analysis techniques are well known to one of ordinary skill in the art, and include spectroscopy, thin layer chromatography, staining methods of various kinds, enzymatic and microbiological methods, and analytical chromatography such as high performance liquid chromatography (see, for example, Ullman, Encyclopedia of Industrial Chemistry, vol. A2, p. 89-90 and p. 443-613, VCH: Weinheim (1985); Fallon, A. et al., (1987) "Applications of HPLC in Biochemistry" in: Laboratory Techniques in Biochemistry and Molecular Biology, vol. 17; Rehm et al. (1993) Biotechnology, vol. 3, Chapter III: "Product recovery and purification", page 469-714, VCH: Weinheim; Belter, P. A. et al. (1988) Bioseparations: downstream processing for biotechnology, John Wiley and Sons; Kennedy, J. F. and Cabral, J. M. S. (1992) Recovery processes for biological materials, John Wiley and Sons; Shaeiwitz, J. A. and Henry, J. D. (1988) Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications.)

In addition to the measurement of the final product of fermentation, it is also possible to analyze other components of the metabolic pathways utilized for the production of the desired compound, such as intermediates and side-products, to determine the overall yield, production, and/or efficiency of production of the compound. Analysis methods include measurements of nutrient levels in the medium (e.g., sugars, hydrocarbons, nitrogen sources, phosphate, and other ions), measurements of biomass composition and growth, analysis of the production of common metabolites of biosynthetic pathways, and measurement of gasses produced during fermentation. Standard methods for these measurements are outlined in Applied Microbial Physiology, A Practical Approach, P. M. Rhodes and P. F. Stanbury, eds., IRL Press, p. 103-129; 131-163; and 165-192 (ISBN: 0199635773) and references cited therein.

Example 10

Purification of the Desired Product from C. Glutamicum Culture

Recovery of the desired product from the *C. glutamicum* cells or supernatant of the above-described culture can be performed by various methods well known in the art. If the desired product is not secreted from the cells, the cells can be harvested from the culture by low-speed centrifugation, the cells can be lysed by standard techniques, such as mechanical force or sonication. The cellular debris is removed by centrifugation, and the supernatant fraction containing the soluble proteins is retained for further purification of the desired compound. If the product is secreted from the *C. glutamicum* cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One of ordinary skill in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986).

The identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al. (1994) *Appl. Environ. Microbiol.* 60: 133-140; Malakhova et al. (1996) *Biotekhnologiya* 11: 27-32; and Schmidt et al. (1998) *Bioprocess Engineer.* 19: 67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

Example 11

Analysis of the Gene Sequences of the Invention

The comparison of sequences and determination of percent homology between two sequences are art-known techniques, and can be accomplished using a mathematical algorithm, such as the algorithm of Karlin and Altschul (1990) *Proc. Natl. Acad. Sci.* USA 87:2264-68, modified as in Karlin and Altschul (1993) *Proc. Natl. Acad. Sci.* USA 90:5873-77. Such an algorithm is incorporated into the NBLAST and XBLAST programs (version 2.0) of Altschul, et al. (1990) *J. Mol Biol.* 215:403-10. BLAST nucleotide searches can be performed with the NBLAST program, score=100, wordlength=12 to obtain nucleotide sequences homologous to MR nucleic acid molecules of the invention. BLAST protein searches can be performed with the XBLAST program, score=50, wordlength=3 to obtain amino acid sequences homologous to MR protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, one of ordinary skill in the art will know how to optimize the parameters of the program (e.g., XBLAST and NBLAST) for the specific sequence being analyzed.

Another example of a mathematical algorithm utilized for the comparison of sequences is the algorithm of Meyers and Miller ((1988) *Comput. Appl. Biosci.* 4: 11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art, and include ADVANCE and ADAM. described in Torelli and Robotti (1994) *Comput. Appl. Biosci.* 10:3-5; and FASTA, described in Pearson and Lipman (1988) *P.N.A.S.* 85:2444-8.

The percent homology between two amino acid sequences can also be accomplished using the GAP program in the GCG software package (available at www.gcg.com), using either a Blosum 62 matrix or a PAM250 matrix, and a gap weight of 12, 10, 8, 6, or 4 and a length weight of 2, 3, or 4. The percent homology between two nucleic acid sequences can be accomplished using the GAP program in the GCG software package, using standard parameters, such as a gap weight of 50 and a length weight of 3.

Example 12

Construction and Operation of DNA Microarrays

The sequences of the invention may additionally be used in the construction and application of DNA microarrays (the design, methodology, and uses of DNA arrays are well known in the art, and are described, for example, in Schena, M. et al. (1995) *Science* 270: 467-470; Wodicka, L. et al. (1997) *Nature Biotechnology* 15: 1359-1367; DeSaizieu, A. et al. (1998) *Nature Biotechnology* 16: 45-48; and DeRisi, J. L. et al. (1997) *Science* 278: 680-686).

DNA microarrays are solid or flexible supports consisting of nitrocellulose, nylon, glass, silicone, or other materials. Nucleic acid molecules may be attached to the surface in an ordered manner. After appropriate labeling, other nucleic acids or nucleic acid mixtures can be hybridized to the immobilized nucleic acid molecules, and the label may be used to monitor and measure the individual signal intensities of the hybridized molecules at defined regions. This methodology allows the simultaneous quantification of the relative or absolute amount of all or selected nucleic acids in the applied nucleic acid sample or mixture. DNA microarrays, therefore, permit an analysis of the expression of multiple (as many as 6800 or more) nucleic acids in parallel (see, e.g., Schena, M. (1996) *BioEssays* 18(5): 427-431).

The sequences of the invention may be used to design oligonucleotide primers which are able to amplify defined regions of one or more *C. glutamicum* genes by a nucleic acid amplification reaction such as the polymerase chain reaction. The choice and design of the 5' or 3' oligonucleotide primers or of appropriate linkers allows the covalent attachment of the resulting PCR products to the surface of a support medium described above (and also described, for example, Schena, M. et al. (1995) *Science* 270: 467-470).

Nucleic acid microarrays may also be constructed by in situ oligonucleotide synthesis as described by Wodicka, L. et al. (1997) *Nature Biotechnology* 15: 1359-1367. By photolithographic methods, precisely defined regions of the matrix are exposed to light. Protective groups which are photolabile are thereby activated and undergo nucleotide addition, whereas regions that are masked from light do not undergo any modification. Subsequent cycles of protection and light activation permit the synthesis of different oligonucleotides at defined positions. Small, defined regions of the genes of the invention may be synthesized on microarrays by solid phase oligonucleotide synthesis.

The nucleic acid molecules of the invention present in a sample or mixture of nucleotides may be hybridized to the microarrays. These nucleic acid molecules can be labeled according to standard methods. In brief, nucleic acid molecules (e.g., mRNA molecules or DNA molecules) are labeled by the incorporation of isotopically or fluorescently labeled nucleotides, e.g., during reverse transcription or DNA synthesis. Hybridization of labeled nucleic acids to microarrays is described (e.g., in Schena, M. et al. (1995) supra; Wodicka, L. et al. (1997), supra; and DeSaizieu A. et al. (1998), supra). The detection and quantification of the hybridized molecule are tailored to the specific incorporated label. Radioactive labels can be detected, for example, as described in Schena, M. et al. (1995) supra) and fluorescent labels may be detected, for example, by the method of Shalon et al. (1996) *Genome Research* 6: 639-645).

The application of the sequences of the invention to DNA microarray technology, as described above, permits comparative analyses of different strains of *C. glutamicum* or other Corynebacteria. For example, studies of inter-strain variations based on individual transcript profiles and the identification of genes that are important for specific and/or desired strain properties such as pathogenicity, productivity and stress tolerance are facilitated by nucleic acid array methodologies. Also, comparisons of the profile of expression of genes of the invention during the course of a fermentation reaction are possible using nucleic acid array technology.

Example 13

Analysis of the Dynamics of Cellular Protein Population (Proteomics)

The genes, compositions, and methods of the invention may be applied to study the interactions and dynamics of populations of proteins, termed 'proteomics'. Protein populations of interest include, but are not limited to, the total protein population of *C. glutamicum* (e.g., in comparison with the protein populations of other organisms), those proteins which are active under specific environmental or metabolic conditions (e.g., during fermentation, at high or low temperature, or at high or low pH), or those proteins which are active during specific phases of growth and development.

Protein populations can be analyzed by various well-known techniques, such as gel electrophoresis. Cellular proteins may be obtained, for example, by lysis or extraction, and may be separated from one another using a variety of electrophoretic techniques. Sodium dodecyl sulfate polyacrylamide gel electrophoresis (SDS-PAGE) separates proteins largely on the basis of their molecular weight. Isoelectric focusing polyacrylamide gel electrophoresis (IEF-PAGE) separates proteins by their isoelectric point (which reflects not only the amino acid sequence but also posttranslational modifications of the protein). Another, more preferred method of protein analysis is the consecutive combination of both IEF-PAGE and SDS-PAGE, known as 2-D-gel electrophoresis (described, for example, in Hermann et al. (1998) *Electrophoresis* 19: 3217-3221; Fountoulakis et al. (1998) *Electrophoresis* 19: 1193-1202; Langen et al. (1997) *Electrophoresis* 18: 1184-1192; Antelmann et al. (1997) *Electrophoresis* 18: 1451-1463). Other separation techniques may also be utilized for protein separation, such as capillary gel electrophoresis; such techniques are well known in the art.

Proteins separated by these methodologies can be visualized by standard techniques, such as by staining or labeling. Suitable stains are known in the art, and include Coomassie Brilliant Blue, silver stain, or fluorescent dyes such as Sypro Ruby (Molecular Probes). The inclusion of radioactively labeled amino acids or other protein precursors (e.g., $^{35}$S-methionine, $^{35}$S-cysteine, $^{14}$C-labelled amino acids, $^{15}$N-amino acids, $^{15}$NO$_3$ or $^{15}$NH$_4^+$ or $^{13}$C-labelled amino acids) in the medium of *C. glutamicum* permits the labeling of proteins from these cells prior to their separation. Similarly, fluorescent labels may be employed. These labeled proteins can be extracted, isolated and separated according to the previously described techniques.

Proteins visualized by these techniques can be further analyzed by measuring the amount of dye or label used. The amount of a given protein can be determined quantitatively using, for example, optical methods and can be compared to the amount of other proteins in the same gel or in other gels. Comparisons of proteins on gels can be made, for example, by optical comparison, by spectroscopy, by image scanning and analysis of gels, or through the use of photographic films and screens. Such techniques are well-known in the art.

To determine the identity of any given protein, direct sequencing or other standard techniques may be employed. For example, N- and/or C-terminal amino acid sequencing (such as Edman degradation) may be used, as may mass spectrometry (in particular MALDI or ESI techniques (see, e.g., Langen et al. (1997) *Electrophoresis* 18: 1184-1192)). The protein sequences provided herein can be used for the identification of *C. glutamicum* proteins by these techniques.

The information obtained by these methods can be used to compare patterns of protein presence, activity, or modification between different samples from various biological conditions (e.g., different organisms, time points of fermentation, media conditions, or different biotopes, among others). Data obtained from such experiments alone, or in combination with other techniques, can be used for various applications, such as to compare the behavior of various organisms in a given (e.g., metabolic) situation, to increase the productivity of strains which produce fine chemicals or to increase the efficiency of the production of fine chemicals.

Example 14

Preparation of a *Corynebacterium Glutamicum* Strain Deficient in the Negative Regulator of Methionine Biosynthesis (RXA00655)

Preparation of a *Corynebacterium glutamicum* strain deficient in the negative regulator of methionine biosynthesis (RXA00655) is carried out by using a self-cloning technique based on homologous recombination. The principle of said technique is visualized in FIG. 1.

The plasmid named pS_delta655 (SEQ ID NO: 3) for preparation of a *C. glutamicum* strain deficient in the negative regulator of methionine biosynthesis (RXA00655) is constructed by ligating PCR amplified fragments of the 5'- and 3' regions of RXA00655 (SEQ ID NO: 1) into the vector pCLiK5MCS_integrativ_sacB (SEQ ID NO: 4) using standard methods (Sambrook et al. (1989), Molecular Cloning. A Laboratory Manual, Cold Spring Harbor; Innis et al. (1990) PCR Protocols. A Guide to Methods and Applications, Academic Press). The PCR amplified 5'-fragment is flanked at its 5'-end by a primer-introduced XhoI site and at its 3'-end by an endogenous NheI site. The PCR amplified 3'-fragment is flanked at its 5'-end by an NheI site followed by an TAA-stopp codon, which are introduced by the primer, and at its 3'-end by a primer-introduced MluI site.

pS_delta655 (SEQ ID NO: 3) is electroporated into the *C. glutamicum* strain ATCC13032 as described (Liebl et al. (1989) *FEMS Microbiol Let* 53:299-303). Transformands with via intermolecular homologous recombination integrated plasmid are selected on CM agar plates supplemented with 50 mg/l kanamycin.

CM-agar:

10.0 g/L D-glucose
2.5 g/L NaCl
2.0 g/L urea
10.0 g/L bacto pepton (Difco)
5.0 g/L yeast extract (Difco)
5.0 g/L beef extract (Difco)
22.0 g/L agar (Difco)
autoclaved (20 min. 121° C.)

Kanamycin-resistant clones are incubated unselectively (without Kanamycin) overnight in CM medium to achieve excision of the plasmid together with the chromosomal copy of RXA00655. The cultures are plated on CM agar containing 10% sucrose. Only those clones in which the integrated pS_delta655 plasmid is excised can grow on CM agar containing sucrose, because the sacB gene in pS_delta655 converts sucrose into levan sucrase, which is toxic for *C. glutamicum*. In the excision either the deletion construct of RXA00655 or the chromosomal copy of RXA00655 is eliminated together with the plasmid.

To identify a clone which has eliminated the chromosomal copy of RXA00655, chromosomal DNA from all potential clones are prepared (Tauch et al. (1995) Plasmid 33:168-179 or Eikmanns et al. (1994) Microbiology 140:1817-1828) and controlled with a Southern Blot analysis according to Sambrook et al. (1989), Molecular Cloning. A Laboratory Manual, Cold Spring Harbor. The knock-out strain is called ATCC13032_delta_rxa00655.

Example 15

Preparation of Methionine with ATCC13032_DELTA_RXA00655

The strains ATCC13032 and ATCC13032_delta_rxa00655 are incubated on a CM-agar plate for 2 d at 30° C. The cells are scraped from the plate and suspended in saline. For the main culture 10 ml medium II and 0.5 g autoclaved CaCO$_3$ (Riedel de Haen) in a 100 ml conical flask are inoculated with the cell suspension to a final OD600 nm of 1.5. Culturing is carried out at 30° C. for 72 h.

Medium II:

| | |
|---|---|
| 40 g/l | sucrose |
| 60 g/l | molasse (calculated on 100% sugar content) |
| 25 g/l | (NH4)2SO4 |
| 0.4 g/l | MgSO4*7H2O |
| 0.6 g/l | KH2PO4 |
| 0.3 mg/l | thiamin*HCl |
| 1 mg/l | biotin (from a 1 mg/ml sterile filtered stock solution adjusted to pH 8.0 with NH4OH) |
| 2 mg/l | FeSO4 |
| 2 mg/l | MnSO4 |
| | The pH is brought to pH 7.8 with NH$_4$OH. Thereafter, the medium is autoclaved (121° C., 20 min). Additional vitamin B12 from a stock solution (200 µg/ml, sterile filtered) is added to a final concentration of 200 µg/l. |

The amount of formed methionine was determined with an Agilent 1100 series LC system HPLC according to a method from Agilent. The with ortho-pthalaldehyde pre-column derivated amino acids are separated on a Hypersil AA-column (Agilent). The strain ATCC13032_delta_rxa00655 produces significantly more methionine than ATCC13032.

Example 16

Preparation of a *Corynebacterium Glutamicum* Strain Overexpressing the Positive Regulator of Methionine Biosynthesis (RXN02910)

The plasmid named pGrxn2910 (SEQ ID NO:13) for overexpressing the positive regulator of methionine biosynthesis (RXN02910; SEQ ID NO:5 or 6) is constructed by ligating a PCR amplified fragment of RXN02910 (SEQ ID NO:9), which encodes the RXN02910 polypeptide (SEQ ID NO:10), into the vector pG (SEQ ID NO:12) using standard methods (Sambrook et al. (1989), Molecular Cloning. A Laboratory Manual, Cold Spring Harbor; Innis et al. (1990) PCR Protocols. A Guide to Methods and Applications, Academic Press). The following pair of oligonucleotide primers was used for the amplification:

```
sense primer:                  (SEQ ID NO: 7)
5'-GAGAGACTCGAGTGGTTTAGGGGATGAGAAACCG-3' antisense primer:              (SEQ ID NO: 8)
5'-CTCTCACTAGTCTACCGCGCCAACAACAGCG-3'
```

The PCR amplified fragment is flanked at its 5'-end by a primer-introduced XhoI site and at its 3'-end by a primer-introduced BcuI site. The amplified fragments contains the open reading frame (ORF) of RXN02910 with additional 5' regions of the corresponding gene including the promotor.

The resulting plasmid pGrxn02910 (SEQ ID NO: 13) is electroporated into the *C. glutamicum* strain ATCC13032 as described (Liebl, et al. (1989) FEMS Microbiology Letters 53:299-303). Transformands are selected on CM agar plates supplemented with 50 mg/l kanamycin (see above). The resulting strain is named ATCC 13032/pGrxn02910.

Example 17

Preparation of Methionine with ATCC13032/PGRXN02910

The strains ATCC13032 and ATCC13032/pGrxn02910 are incubated on a CM-agar plate for 2 days at 30° C. The cells are scraped from the plate and suspended in saline. For the main culture 10 ml medium II (see above) and 0.5 g autoclaved CaCO$_3$ (Riedel de Haen) in a 100 ml conical flask are inoculated with the cell suspension to a final OD600 nm of 1.5.

Culturing is carried out at 30° C. for 72 h. In the case of ATCC13032/pGrxn02910 all plates and cultures contain additional 50 μg/l kanamycin. The amount of formed methionine was determined with an Agilent 1100 series LC system HPLC according to a method from Agilent. The with ortho-phtalaldehyde pre-column derivated amino acids are separated on a Hypersil AA-column (Agilent). The strain ATCC13032/pGrxn02910 produces significantly more methionine than ATCC13032.

Example 18

Preparation of a *Corynebacterium Glutamicum* Strain Deficient in the Positive Regulator of Methionine Biosynthesis (RXN02910)

Preparation of a *Corynebacterium glutamicum* strain deficient in the positive regulator of methionine biosynthesis (RXN02910) is carried out by insertion of a kanamycin selectable vector.

The plasmid named pIntegrativ_delta2910 (SEQ ID NO: 15) for preparation of a *C. glutamicum* strain deficient in the regulator of methionine biosynthesis (rxn02910) is constructed by ligating a PCR amplified fragment of rxn02910 into the vector pIntegrativ (SEQ ID NO: 14) using standard methods (Sambrook et al. (1989), Molecular Cloning. A Laboratory Manual, Cold Spring Harbor; Innis et al. (1990) PCR Protocols. A Guide to Methods and Applications, Academic Press). The PCR amplified fragment (SEQ ID NO: 11) is flanked at its 5'-end by a primer-introduced XhoI site and at its 3'-end by a primer-introduced EcoRV site.

pIntegrativ_delta2910 (SEQ ID NO: 15) is electroporated into the *C. glutamicum* strain ATCC13032 as described (Liebl et al. (1989). FEMS Microbiol Let 53:299-303). Transformands with via intermolecular homologous recombination integrated plasmid are selected on CM agar plates supplemented with 50 mg/l kanamycin. To identify a clone which has an integrated plasmid and thus disrupted the chromosomal copy of RXN02910, chromosomal DNA from potential clones are prepared (Tauch et al. (1995) Plasmid 33:168-179 or Eikmanns et al. (1994) Microbiology 140:1817-1828) and controlled with a Southern Blot analysis according to Sambrook et al. (1989), Molecular Cloning. A Laboratory Manual, Cold Spring Harbor.

The knock-out strain is called ATCC13032_delta_rxn02910. The amount of formed methionine was determined with an Agilent 1100 series LC system HPLC according to a method from Agilent. The with ortho-phtalaldehyde pre-column derivated amino acids are separated on a Hypersil AA-column (Agilent).

The strain ATCC13032_delta_rxn02910 produces significant less methionine than ATCC13032, thereby demonstrating that rxn02910 is indeed a positive regulator of methionine biosynthesis.

TABLE 1

Corynebacterium and Brevibacterium Strains Which May be Used in the Practice of the Invention

| Genus | species | ATCC | FERM | NRRL | CECT | NCIMB | CBS | NCTC | DSMZ |
|---|---|---|---|---|---|---|---|---|---|
| Brevibacterium | ammoniagenes | 21054 | | | | | | | |
| Brevibacterium | ammoniagenes | 19350 | | | | | | | |
| Brevibacterium | ammoniagenes | 19351 | | | | | | | |
| Brevibacterium | ammoniagenes | 19352 | | | | | | | |
| Brevibacterium | ammoniagenes | 19353 | | | | | | | |
| Brevibacterium | ammoniagenes | 19354 | | | | | | | |
| Brevibacterium | ammoniagenes | 19355 | | | | | | | |
| Brevibacterium | ammoniagenes | 19356 | | | | | | | |
| Brevibacterium | ammoniagenes | 21055 | | | | | | | |
| Brevibacterium | ammoniagenes | 21077 | | | | | | | |
| Brevibacterium | ammoniagenes | 21553 | | | | | | | |
| Brevibacterium | ammoniagenes | 21580 | | | | | | | |
| Brevibacterium | ammoniagenes | 39101 | | | | | | | |
| Brevibacterium | butanicum | 21196 | | | | | | | |
| Brevibacterium | divaricatum | 21792 | P928 | | | | | | |
| Brevibacterium | flavum | 21474 | | | | | | | |
| Brevibacterium | flavum | 21129 | | | | | | | |
| Brevibacterium | flavum | 21518 | | | | | | | |
| Brevibacterium | flavum | | | B11474 | | | | | |
| Brevibacterium | flavum | | | B11472 | | | | | |
| Brevibacterium | flavum | 21127 | | | | | | | |
| Brevibacterium | flavum | 21128 | | | | | | | |
| Brevibacterium | flavum | 21427 | | | | | | | |
| Brevibacterium | flavum | 21475 | | | | | | | |
| Brevibacterium | flavum | 21517 | | | | | | | |
| Brevibacterium | flavum | 21528 | | | | | | | |
| Brevibacterium | flavum | 21529 | | | | | | | |
| Brevibacterium | flavum | | | B11477 | | | | | |
| Brevibacterium | flavum | | | B11478 | | | | | |
| Brevibacterium | flavum | 21127 | | | | | | | |
| Brevibacterium | flavum | | | B11474 | | | | | |
| Brevibacterium | healii | 15527 | | | | | | | |
| Brevibacterium | ketoglutamicum | 21004 | | | | | | | |
| Brevibacterium | ketoglutamicum | 21089 | | | | | | | |
| Brevibacterium | ketosoreductum | 21914 | | | | | | | |
| Brevibacterium | lactofermentum | | | | 70 | | | | |
| Brevibacterium | lactofermentum | | | | 74 | | | | |
| Brevibacterium | lactofermentum | | | | 77 | | | | |
| Brevibacterium | lactofermentum | 21798 | | | | | | | |
| Brevibacterium | lactofermentum | 21799 | | | | | | | |

TABLE 1-continued

Corynebacterium and Brevibacterium Strains Which May be Used in the Practice of the Invention

| Genus | species | ATCC | FERM | NRRL | CECT | NCIMB | CBS | NCTC | DSMZ |
|---|---|---|---|---|---|---|---|---|---|
| Brevibacterium | lactofermentum | 21800 | | | | | | | |
| Brevibacterium | lactofermentum | 21801 | | | | | | | |
| Brevibacterium | lactofermentum | | | B11470 | | | | | |
| Brevibacterium | lactofermentum | | | B11471 | | | | | |
| Brevibacterium | lactofermentum | 21086 | | | | | | | |
| Brevibacterium | lactofermentum | 21420 | | | | | | | |
| Brevibacterium | lactofermentum | 21086 | | | | | | | |
| Brevibacterium | lactofermentum | 31269 | | | | | | | |
| Brevibacterium | linens | 9174 | | | | | | | |
| Brevibacterium | linens | 19391 | | | | | | | |
| Brevibacterium | linens | 8377 | | | | | | | |
| Brevibacterium | paraffinolyticum | | | | | 11160 | | | |
| Brevibacterium | spec. | | | | | | 717.73 | | |
| Brevibacterium | spec. | | | | | | 717.73 | | |
| Brevibacterium | spec. | 14604 | | | | | | | |
| Brevibacterium | spec. | 21860 | | | | | | | |
| Brevibacterium | spec. | 21864 | | | | | | | |
| Brevibacterium | spec. | 21865 | | | | | | | |
| Brevibacterium | spec. | 21866 | | | | | | | |
| Brevibacterium | spec. | 19240 | | | | | | | |
| Corynebacterium | acetoacidophilum | 21476 | | | | | | | |
| Corynebacterium | acetoacidophilum | 13870 | | | | | | | |
| Corynebacterium | acetoglutamicum | | | B11473 | | | | | |
| Corynebacterium | acetoglutamicum | | | B11475 | | | | | |
| Corynebacterium | acetoglutamicum | 15806 | | | | | | | |
| Corynebacterium | acetoglutamicum | 21491 | | | | | | | |
| Corynebacterium | acetoglutamicum | 31270 | | | | | | | |
| Corynebacterium | acetophilum | | | B3671 | | | | | |
| Corynebacterium | ammoniagenes | 6872 | | | | | | | 2399 |
| Corynebacterium | ammoniagenes | 15511 | | | | | | | |
| Corynebacterium | fujiokense | 21496 | | | | | | | |
| Corynebacterium | glutamicum | 14067 | | | | | | | |
| Corynebacterium | glutamicum | 39137 | | | | | | | |
| Corynebacterium | glutamicum | 21254 | | | | | | | |
| Corynebacterium | glutamicum | 21255 | | | | | | | |
| Corynebacterium | glutamicum | 31830 | | | | | | | |
| Corynebacterium | glutamicum | 13032 | | | | | | | |
| Corynebacterium | glutamicum | 14305 | | | | | | | |
| Corynebacterium | glutamicum | 15455 | | | | | | | |
| Corynebacterium | glutamicum | 13058 | | | | | | | |
| Corynebacterium | glutamicum | 13059 | | | | | | | |
| Corynebacterium | glutamicum | 13060 | | | | | | | |
| Corynebacterium | glutamicum | 21492 | | | | | | | |
| Corynebacterium | glutamicum | 21513 | | | | | | | |
| Corynebacterium | glutamicum | 21526 | | | | | | | |
| Corynebacterium | glutamicum | 21543 | | | | | | | |
| Corynebacterium | glutamicum | 13287 | | | | | | | |
| Corynebacterium | glutamicum | 21851 | | | | | | | |
| Corynebacterium | glutamicum | 21253 | | | | | | | |
| Corynebacterium | glutamicum | 21514 | | | | | | | |
| Corynebacterium | glutamicum | 21516 | | | | | | | |
| Corynebacterium | glutamicum | 21299 | | | | | | | |
| Corynebacterium | glutamicum | 21300 | | | | | | | |
| Corynebacterium | glutamicum | 39684 | | | | | | | |
| Corynebacterium | glutamicum | 21488 | | | | | | | |
| Corynebacterium | glutamicum | 21649 | | | | | | | |
| Corynebacterium | glutamicum | 21650 | | | | | | | |
| Corynebacterium | glutamicum | 19223 | | | | | | | |
| Corynebacterium | glutamicum | 13869 | | | | | | | |
| Corynebacterium | glutamicum | 21157 | | | | | | | |
| Corynebacterium | glutamicum | 21158 | | | | | | | |
| Corynebacterium | glutamicum | 21159 | | | | | | | |
| Corynebacterium | glutamicum | 21355 | | | | | | | |
| Corynebacterium | glutamicum | 31808 | | | | | | | |
| Corynebacterium | glutamicum | 21674 | | | | | | | |
| Corynebacterium | glutamicum | 21562 | | | | | | | |
| Corynebacterium | glutamicum | 21563 | | | | | | | |
| Corynebacterium | glutamicum | 21564 | | | | | | | |
| Corynebacterium | glutamicum | 21565 | | | | | | | |
| Corynebacterium | glutamicum | 21566 | | | | | | | |
| Corynebacterium | glutamicum | 21567 | | | | | | | |
| Corynebacterium | glutamicum | 21568 | | | | | | | |
| Corynebacterium | glutamicum | 21569 | | | | | | | |
| Corynebacterium | glutamicum | 21570 | | | | | | | |

TABLE 1-continued

Corynebacterium and Brevibacterium Strains Which May be Used in the Practice of the Invention

| Genus | species | ATCC | FERM | NRRL | CECT | NCIMB | CBS | NCTC | DSMZ |
|---|---|---|---|---|---|---|---|---|---|
| Corynebacterium | glutamicum | 21571 | | | | | | | |
| Corynebacterium | glutamicum | 21572 | | | | | | | |
| Corynebacterium | glutamicum | 21573 | | | | | | | |
| Corynebacterium | glutamicum | 21579 | | | | | | | |
| Corynebacterium | glutamicum | 19049 | | | | | | | |
| Corynebacterium | glutamicum | 19050 | | | | | | | |
| Corynebacterium | glutamicum | 19051 | | | | | | | |
| Corynebacterium | glutamicum | 19052 | | | | | | | |
| Corynebacterium | glutamicum | 19053 | | | | | | | |
| Corynebacterium | glutamicum | 19054 | | | | | | | |
| Corynebacterium | glutamicum | 19055 | | | | | | | |
| Corynebacterium | glutamicum | 19056 | | | | | | | |
| Corynebacterium | glutamicum | 19057 | | | | | | | |
| Corynebacterium | glutamicum | 19058 | | | | | | | |
| Corynebacterium | glutamicum | 19059 | | | | | | | |
| Corynebacterium | glutamicum | 19060 | | | | | | | |
| Corynebacterium | glutamicum | 19185 | | | | | | | |
| Corynebacterium | glutamicum | 13286 | | | | | | | |
| Corynebacterium | glutamicum | 21515 | | | | | | | |
| Corynebacterium | glutamicum | 21527 | | | | | | | |
| Corynebacterium | glutamicum | 21544 | | | | | | | |
| Corynebacterium | glutamicum | 21492 | | | | | | | |
| Corynebacterium | glutamicum | | | B8183 | | | | | |
| Corynebacterium | glutamicum | | | B8182 | | | | | |
| Corynebacterium | glutamicum | | | B12416 | | | | | |
| Corynebacterium | glutamicum | | | B12417 | | | | | |
| Corynebacterium | glutamicum | | | B12418 | | | | | |
| Corynebacterium | glutamicum | | | B11476 | | | | | |
| Corynebacterium | glutamicum | 21608 | | | | | | | |
| Corynebacterium | lilium | | P973 | | | | | | |
| Corynebacterium | nitrilophilus | 21419 | | | | 11594 | | | |
| Corynebacterium | spec. | | P4445 | | | | | | |
| Corynebacterium | spec. | | P4446 | | | | | | |
| Corynebacterium | spec. | 31088 | | | | | | | |
| Corynebacterium | spec. | 31089 | | | | | | | |
| Corynebacterium | spec. | 31090 | | | | | | | |
| Corynebacterium | spec. | 31090 | | | | | | | |
| Corynebacterium | spec. | 31090 | | | | | | | |
| Corynebacterium | spec. | 15954 | | | | | | | 20145 |
| Corynebacterium | spec. | 21857 | | | | | | | |
| Corynebacterium | spec. | 21862 | | | | | | | |
| Corynebacterium | spec. | 21863 | | | | | | | |

ATCC: American Type Culture Collection, Rockville, MD, USA
FERM: Fermentation Research Institute, Chiba, Japan
NRRL: ARS Culture Collection, Northern Regional Research Laboratory, Peoria, IL, USA
CECT: Coleccion Espanola de Cultivos Tipo, Valencia, Spain
NCIMB: National Collection of Industrial and Marine Bacteria Ltd., Aberdeen, UK
CBS: Centraalbureau voor Schimmelcultures, Baarn, NL
NCTC: National Collection of Type Cultures, London, UK
DSMZ: Deutsche Sammlung von Mikroorganismen und Zellkulturen, Braunschweig, Germany
For reference see Sugawara, H. et al. (1993) World directory of collections of cultures of microorganisms: Bacteria, fungi and yeasts (4$^{th}$ edn), World federation for culture collections world data center on microorganisms, Saimata, Japen.

EQUIVALENTS

Those of ordinary skill in the art will recognize, or will be able to ascertain using no more than routine experimentation, many equivalents to the specific embodiments of the invention described herein. Such equivalents are intended to be encompassed by the following claims.

What is claimed:

1. An isolated nucleic acid molecule which encodes a polypeptide comprising the amino acid sequence set forth in SEQ ID NO:6.

2. An isolated nucleic acid molecule comprising the nucleic acid molecule of claim 1, and a nucleotide sequence encoding a heterologous polypeptide.

3. A vector comprising the isolated nucleic acid molecule of claim 1.

4. The vector of claim 3, which is an expression vector.

5. A host cell comprising the expression vector of claim 4.

6. A method of producing a polypeptide comprising the amino acid sequence of SEQ ID NO:6 or SEQ ID NO:17, comprising culturing the host cell of claim 5 in an appropriate culture medium to thereby produce the polypeptide.

7. A method for producing methionine, comprising culturing a microorganism belonging to the genus *Corynebacterium* or *Brevibacterium* transformed with the vector of claim 3 such that methionine is produced.

8. The method of claim 7, wherein said method further comprises the step of recovering methionine from said culture.

9. The method of claim 7, wherein said microorganism belongs to the genus *Corynebacterium*.

10. The method of claim 7, wherein said microorganism is selected from the group consisting of: *Corynebacterium glutamicum, Corynebacterium efficiens, Corynebacterium herculis, Corynebacterium lilium, Corynebacterium acetoacidophilum, Corynebacterium acetoglutamicum, Corynebacterium acetophilum, Corynebacterium ammoniagenes, Corynebacterium fujiokense, Corynebacterium nitrilophilus, Brevibacterium ammoniagenes, Brevibacterium butanicum, Brevibacterium divaricatum, Brevibacterium flavum, Brevibacterium healii, Brevibacterium ketoglutamicum, Brevibacterium ketosoreductum, Brevibacterium lactofermentum, Brevibacterium linens*, and *Brevibacterium paraffinolyticum*.

11. The method of claim 7, wherein expression of the nucleic acid molecule from said vector results in increased production of said methionine.

12. An isolated nucleic acid molecule comprising the full complement of the nucleic acid molecule of claim 1.

13. A vector comprising the isolated nucleic acid molecule of claim 12.

14. A host cell comprising the vector of claim 13.

15. An isolated nucleic acid molecule comprising the nucleotide sequence set forth in SEQ ID NO:5.

16. An isolated nucleic acid molecule comprising the nucleic acid molecule of claim 15, and a nucleotide sequence encoding a heterologous polypeptide.

17. A vector comprising the isolated nucleic acid molecule of claim 15.

18. The vector of claim 17, which is an expression vector.

19. A host cell comprising the expression vector of claim 18.

20. A method of producing a polypeptide comprising the amino acid sequence of SEQ ID NO:6 or SEQ ID NO:17, comprising culturing the host cell of claim 19 in an appropriate culture medium to thereby produce the polypeptide.

21. A method for producing methionine, comprising culturing a microorganism belonging to the genus *Corynebacterium* or *Brevibacterium* transformed with the vector of claim 18 such that methionine is produced.

22. The method of claim 21, wherein said method further comprises the step of recovering methionine from said culture.

23. The method of claim 21, wherein said microorganism belongs to the genus *Corynebacterium*.

24. The method of claim 21, wherein said microorganism is selected from the group consisting of: *Corynebacterium glutamicum, Corynebacterium efficiens, Corynebacterium herculis, Corynebacterium lilium, Corynebacterium acetoacidophilum, Corynebacterium acetoglutamicum, Corynebacterium acetophilum, Corynebacterium ammoniagenes, Corynebacterium fujiokense, Corynebacterium*

*nitrilophilus, Brevibacterium ammoniagenes, Brevibacterium butanicum, Brevibacterium divaricatum, Brevibacterium flavum, Brevibacterium healii, Brevibacterium ketoglutamicum, Brevibacterium ketosoreductum, Brevibacterium lactofermentum, Brevibacterium linens,* and *Brevibacterium paraffinolyticum.*

25. The method of claim 21, wherein expression of the nucleic acid molecule from said vector results in increased production of said methionine.

26. An isolated nucleic acid molecule comprising the full complement of the nucleic acid molecule of claim 15.

27. A vector comprising the isolated nucleic acid molecule of claim 26.

28. A host cell comprising the vector of claim 27.

29. An isolated nucleic acid molecule which encodes a polypeptide comprising the amino acid sequence set forth in SEQ ID NO:17.

30. An isolated nucleic acid molecule comprising the nucleic acid molecule of claim 29, and a nucleotide sequence encoding a heterologous polypeptide.

31. A vector comprising the isolated nucleic acid molecule of claim 29.

32. The vector of claim 31, which is an expression vector.

33. A host cell comprising the expression vector of claim 32.

34. A method of producing a polypeptide comprising the amino acid sequence of SEQ ID NO:17, comprising culturing the host cell of claim 33 in an appropriate culture medium to thereby produce the polypeptide.

35. A method for producing methionine, comprising culturing a microorganism belonging to the genus *Corynebacterium* or *Brevibacterium* transformed with the vector of claim 31 such that methionine is produced.

36. The method of claim 35, wherein said method further comprises the step of recovering methionine from said culture.

37. The method of claim 35, wherein said microorganism belongs to the genus *Corynebacterium.*

38. The method of claim 35, wherein said microorganism is selected from the group consisting of: *Corynebacterium glutamicum, Corynebacterium efficiens, Corynebacterium herculis, Corynebacterium lilium, Corynebacterium acetoacidophilum, Corynebacterium acetoglutamicum, Corynebacterium acetophilum, Corynebacterium ammoniagenes, Corynebacterium fujiokense, Corynebacterium nitrilophilus, Brevibacterium ammoniagenes, Brevibacterium butanicum, Brevibacterium divaricatum, Brevibacterium flavum, Brevibacterium healii, Brevibacterium ketoglutamicum, Brevibacterium ketosoreductum, Brevibacterium lactofermentum, Brevibacterium linens,* and *Brevibacterium paraffinolyticum.*

39. The method of claim 35, wherein expression of the nucleic acid molecule from said vector results in increased production of said methionine.

40. An isolated nucleic acid molecule comprising the full complement of the nucleic acid molecule of claim 29.

41. A vector comprising the isolated nucleic acid molecule of claim 40.

42. A host cell comprising the vector of claim 41.

43. An isolated nucleic acid molecule comprising the nucleotide sequence set forth in SEQ ID NO:16.

44. An isolated nucleic acid molecule comprising the nucleic acid molecule of claim 43, and a nucleotide sequence encoding a heterologous polypeptide.

45. A vector comprising the isolated nucleic acid molecule of claim 43.

46. The vector of claim 45, which is an expression vector.

47. A host cell comprising the expression vector of claim 46.

48. A method of producing a polypeptide comprising the amino acid sequence of SEQ ID NO:17, comprising culturing the host cell of claim 47 in an appropriate culture medium to thereby produce the polypeptide.

49. A method for producing methionine, comprising culturing a microorganism belonging to the genus *Corynebacterium* or *Brevibacterium* transformed with the vector of claim 46 such that methionine is produced.

50. The method of claim 49, wherein said method further comprises the step of recovering methionine from said culture.

51. The method of claim 49, wherein said microorganism belongs to the genus *Corynebacterium.*

52. The method of claim 49, wherein said microorganism is selected from the group consisting of: *Corynebacterium glutamicum, Corynebacterium efficiens, Corynebacterium herculis, Corynebacterium lilium, Corynebacterium acetoacidophilum, Corynebacterium acetoglutamicum, Corynebacterium acetophilum, Corynebacterium ammoniagenes, Corynebacterium fujiokense, Corynebacterium nitrilophilus, Brevibacterium ammoniagenes, Brevibacterium butanicum, Brevibacterium divaricatum, Brevibacterium flavum, Brevibacterium healii, Brevibacterium ketoglutamicum, Brevibacterium ketosoreductum, Brevibacterium lactofermentum, Brevibacterium linens,* and *Brevibacterium paraffinolyticum.*

53. The method of claim 49, wherein expression of the nucleic acid molecule from said vector results in increased production of said methionine.

54. An isolated nucleic acid molecule comprising the full complement of the nucleic acid molecule of claim 43.

55. A vector comprising the isolated nucleic acid molecule of claim 54.

56. A host cell comprising the vector of claim 55.

* * * * *

UNITED STATES PATENT AND TRADEMARK OFFICE
CERTIFICATE OF CORRECTION

PATENT NO. : 7,892,798 B2  Page 1 of 1
APPLICATION NO. : 10/307138
DATED : February 22, 2011
INVENTOR(S) : Markus Pompejus et al.

It is certified that error appears in the above-identified patent and that said Letters Patent is hereby corrected as shown below:

On the title page please correct the title to read:

-- NUCLEIC ACID MOLECULES ENCODING METABOLIC REGULATORY PROTEINS FROM CORYNEBACTERIUM GLUTAMICUM, USEFUL FOR INCREASING THE PRODUCTION OF METHIONINE BY A MICROORGANISM --

At Page 1, Column 1 please correct the title to read:

-- NUCLEIC ACID MOLECULES ENCODING METABOLIC REGULATORY PROTEINS FROM CORYNEBACTERIUM GLUTAMICUM, USEFUL FOR INCREASING THE PRODUCTION OF METHIONINE BY A MICROORGANISM --

Signed and Sealed this
Nineteenth Day of April, 2011

David J. Kappos
*Director of the United States Patent and Trademark Office*

SEQUENCE LISTING

```
<160> NUMBER OF SEQ ID NOS: 25

<210> SEQ ID NO 1
<211> LENGTH: 762
<212> TYPE: DNA
<213> ORGANISM: Corynebacterium glutamicum
<220> FEATURE:
<221> NAME/KEY: CDS
```

```
<222> LOCATION: (101)..(742)
<223> OTHER INFORMATION: coding for negative regulator of methionine
      biosynthesis (RXA00655)

<400> SEQUENCE: 1
ttgcctgtgg attaaaacta tacgaaccgg tttgtctata ttggtgttag acagttcgtc      60
gtatcttgaa acagaccaac ccgaaaggac gtggccgaac gtg gct gct agc gct     115
                                             Val Ala Ala Ser Ala
                                               1               5 tca ggc aag agt aaa aca agt gcc ggg gca aac cgt cgt cgc aat cga     163
Ser Gly Lys Ser Lys Thr Ser Ala Gly Ala Asn Arg Arg Arg Asn Arg
         10                  15                  20 cca agc ccc cga cag cgt ctc ctc gat agc gca acc aac ctt ttc acc     211
Pro Ser Pro Arg Gln Arg Leu Leu Asp Ser Ala Thr Asn Leu Phe Thr
             25                  30                  35 aca gaa ggt att cgc gtc atc ggt att gat cgt atc ctc cgt gaa gct     259
Thr Glu Gly Ile Arg Val Ile Gly Ile Asp Arg Ile Leu Arg Glu Ala
     40                  45                  50 gac gtg gcg aag gcg agc ctc tat tcc ctt ttc gga tcg aag gac gcc     307
Asp Val Ala Lys Ala Ser Leu Tyr Ser Leu Phe Gly Ser Lys Asp Ala
 55                  60                  65 ttg gtt att gca tac ctg gag aac ctc gat cag ctg tgg cgt gaa gcg     355
Leu Val Ile Ala Tyr Leu Glu Asn Leu Asp Gln Leu Trp Arg Glu Ala
 70                  75                  80                  85 tgg cgt gag cgc acc gtc ggt atg aag gat ccg gaa gat aaa atc atc     403
Trp Arg Glu Arg Thr Val Gly Met Lys Asp Pro Glu Asp Lys Ile Ile
                 90                  95                 100 gcg ttc ttt gat cag tgc att gag gaa gaa cca gaa aaa gat ttc cgc     451
Ala Phe Phe Asp Gln Cys Ile Glu Glu Glu Pro Glu Lys Asp Phe Arg
                105                 110                 115 ggc tcg cac ttt cag aat gcg gct agt gag tac cct cgc ccc gaa act     499
Gly Ser His Phe Gln Asn Ala Ala Ser Glu Tyr Pro Arg Pro Glu Thr
            120                 125                 130 gat agc gaa aag ggc att gtt gca gca gtg tta gag cac cgc gag tgg     547
Asp Ser Glu Lys Gly Ile Val Ala Ala Val Leu Glu His Arg Glu Trp
        135                 140                 145 tgt cat aag act ctg act gat ttg ctc act gag aag aac ggc tac cca     595
Cys His Lys Thr Leu Thr Asp Leu Leu Thr Glu Lys Asn Gly Tyr Pro
150                 155                 160                 165 ggc acc acc cag gcg aat cag ctg ttg gtg ttc ctt gat ggt gga ctt     643
Gly Thr Thr Gln Ala Asn Gln Leu Leu Val Phe Leu Asp Gly Gly Leu
                170                 175                 180 gct gga tct cga ttg gtc cac aac atc agt cct ctt gag acg gct cgc     691
Ala Gly Ser Arg Leu Val His Asn Ile Ser Pro Leu Glu Thr Ala Arg
            185                 190                 195 gat ttg gct cgg cag ttg ttg tcg gct cca cct gcg gac tac tca att     739
Asp Leu Ala Arg Gln Leu Leu Ser Ala Pro Pro Ala Asp Tyr Ser Ile
        200                 205                 210 tag tttcttcatt ttccgaaggg                                            762

<210> SEQ ID NO 2
<211> LENGTH: 213
<212> TYPE: PRT
<213> ORGANISM: Corynebacterium glutamicum

<400> SEQUENCE: 2

Val Ala Ala Ser Ala Ser Gly Lys Ser Lys Thr Ser Ala Gly Ala Asn
  1               5                  10                  15

Arg Arg Arg Asn Arg Pro Ser Pro Arg Gln Arg Leu Leu Asp Ser Ala
             20                  25                  30
```

-continued

```
Thr Asn Leu Phe Thr Thr Glu Gly Ile Arg Val Ile Gly Ile Asp Arg
             35                  40                  45

Ile Leu Arg Glu Ala Asp Val Ala Lys Ala Ser Leu Tyr Ser Leu Phe
     50                  55                  60

Gly Ser Lys Asp Ala Leu Val Ile Ala Tyr Leu Glu Asn Leu Asp Gln
 65                  70                  75                  80

Leu Trp Arg Glu Ala Trp Arg Glu Arg Thr Val Gly Met Lys Asp Pro
                 85                  90                  95

Glu Asp Lys Ile Ile Ala Phe Phe Asp Gln Cys Ile Glu Glu Glu Pro
            100                 105                 110

Glu Lys Asp Phe Arg Gly Ser His Phe Gln Asn Ala Ala Ser Glu Tyr
        115                 120                 125

Pro Arg Pro Glu Thr Asp Ser Glu Lys Gly Ile Val Ala Ala Val Leu
    130                 135                 140

Glu His Arg Glu Trp Cys His Lys Thr Leu Thr Asp Leu Leu Thr Glu
145                 150                 155                 160

Lys Asn Gly Tyr Pro Gly Thr Thr Gln Ala Asn Gln Leu Leu Val Phe
                165                 170                 175

Leu Asp Gly Gly Leu Ala Gly Ser Arg Leu Val His Asn Ile Ser Pro
            180                 185                 190

Leu Glu Thr Ala Arg Asp Leu Ala Arg Gln Leu Leu Ser Ala Pro Pro
        195                 200                 205

Ala Asp Tyr Ser Ile
    210
```

<210> SEQ ID NO 3
<211> LENGTH: 4900
<212> TYPE: DNA
<213> ORGANISM: Artificial Sequence
<220> FEATURE:
<223> OTHER INFORMATION: Description of Artificial Sequence: knock-out
      vector construct pS_delta655
<220> FEATURE:
<221> NAME/KEY: misc_feature
<222> LOCATION: (14)..(295)
<223> OTHER INFORMATION: 5'-fragment of RXA00655 sequence
<220> FEATURE:
<221> NAME/KEY: misc_feature
<222> LOCATION: (305)..(614)
<223> OTHER INFORMATION: 3'-fragment of RXA0655 sequence
<220> FEATURE:
<221> NAME/KEY: misc_feature
<222> LOCATION: (3003)..(4424)
<223> OTHER INFORMATION: coding for levan sucrase (sacB) from Bacillus
      subtilis
<220> FEATURE:
<221> NAME/KEY: promoter
<222> LOCATION: (4425)..(4887)
<223> OTHER INFORMATION: promoter region for sacB
<220> FEATURE:
<221> NAME/KEY: misc_feature
<222> LOCATION: (1042)..(1833)
<223> OTHER INFORMATION: coding for kanamycin resistance
<220> FEATURE:
<221> NAME/KEY: misc_feature
<222> LOCATION: (1042)..(1833)
<223> OTHER INFORMATION: kanamycin resistance from Tn5
<220> FEATURE:
<221> NAME/KEY: misc_feature
<222> LOCATION: (2100)..(2960)
<223> OTHER INFORMATION: Ori from pMB for replication in E.coli

<400> SEQUENCE: 3
tttaaatctc gagtgccggt ggcggcttga tcttcagctt catcacatgt ctgattggtg      60

```
ctgtcatttt gctgacgatc gtgcagttct tcactcggaa gaagtaatct gctttaaatc    120
cgtagggcct gttgatattt cgatatcaac aggccttttg gtcattttgg ggtggaaaaa    180
gcgctagact tgcctgtgga ttaaaactat acgaaccggt ttgtctatat tggtgttaga    240
cagttcgtcg tatcttgaaa cagaccaacc cgaaaggacg tggccgaacg tggctgctag    300
ctaatccttg atggtggact tgctggatct cgattggtcc acaacatcag tcctcttgag    360
acggctcgcg atttggctcg gcagttgttg tcggctccac ctgcgactca tcaatttag    420
tttcttcatt ttccgaaggg gtatcttcgt tggggaggc gtcgataagc cccttctttt    480
tagctttaac ctcagcgcga cgctgcttta agcgctgcat ggcggcgcgg ttcatttcac    540
gttgcgtttc gcgcctcttg ttcgcgattt ctttgcgggc ctgttttgct tcgttgattt    600
cggcagtacg ggtacgcgt catatgacta gttcggacct agggatatcg tcgacatcga    660
tgctcttctg cgttaattaa caattgggat cctctagacc cgggatttaa atcgctagcg    720
ggctgctaaa ggaagcggaa cacgtagaaa gccagtccgc agaaacggtg ctgaccccgg    780
atgaatgtca gctactgggc tatctggaca agggaaaacg caagcgcaaa gagaaagcag    840
gtagcttgca gtgggcttac atggcgatag ctagactggg cggttttatg gacagcaagc    900
gaaccggaat tgccagctgg ggcgccctct ggtaaggttg ggaagccctg caaagtaaac    960
tggatggctt tcttgccgcc aaggatctga tggcgcaggg gatcaagatc tgatcaagag   1020
acaggatgag gatcgtttcg catgattgaa caagatggat tgcacgcagg ttctccggcc   1080
gcttgggtgg agaggctatt cggctatgac tgggcacaac agacaatcgg ctgctctgat   1140
gccgccgtgt tccggctgtc agcgcagggg cgcccggttc tttttgtcaa gaccgacctg   1200
tccggtgccc tgaatgaact gcaggacgag gcagcgcggc tatcgtggct ggccacgacg   1260
ggcgttcctt gcgcagctgt gctcgacgtt gtcactgaag cgggaaggga ctggctgcta   1320
ttgggcgaag tgccggggca ggatctcctg tcatctcacc ttgctcctgc cgagaaagta   1380
tccatcatgg ctgatgcaat gcggcggctg catacgcttg atccggctac ctgcccattc   1440
gaccaccaag cgaaacatcg catcgagcga gcacgtactc ggatggaagc cggtcttgtc   1500
gatcaggatg atctggacga agagcatcag gggctcgcgc cagccgaact gttcgccagg   1560
ctcaaggcgc gcatgcccga cggcgaggat ctcgtcgtga cccatggcga tgcctgcttg   1620
ccgaatatca tggtggaaaa tggccgcttt tctggattca tcgactgtgg ccggctgggt   1680
gtggcggacc gctatcagga catagcgttg gctacccgtg atattgctga agagcttggc   1740
ggcgaatggg ctgaccgctt cctcgtgctt tacggtatcg ccgctcccga ttcgcagcgc   1800
atcgccttct atcgccttct tgacgagttc ttctgagcgg gactctgggg ttcgaaatga   1860
ccgaccaagc gacgcccaac ctgccatcac gagatttcga ttccaccgcc gccttctatg   1920
aaaggttggg cttcggaatc gttttccggg acgccggctg gatgatcctc cagcgcgggg   1980
atctcatgct ggagttcttc gcccacgcta gcggcgcgcc ggccgcccg tgtgaaata    2040
ccgcacagat gcgtaaggag aaaataccgc atcaggcgct cttccgcttc ctcgctcact   2100
gactcgctgc gctcggtcgt tcggctgcgg cgagcggtat cagctcactc aaaggcggta   2160
atacggttat ccacagaatc aggggataac gcaggaaaga acatgtgagc aaaaggccag   2220
caaaaggcca ggaaccgtaa aaaggccgcg ttgctggcgt ttttccatag gctccgcccc   2280
cctgacgagc atcacaaaaa tcgacgctca agtcagaggt ggcgaaaccc gacaggacta   2340
taaagatacc aggcgtttcc ccctggaagc tccctcgtgc gctctcctgt tccgaccctg   2400
ccgcttaccg gatacctgtc cgcctttctc ccttcgggaa gcgtggcgct ttctcatagc   2460
```

```
tcacgctgta ggtatctcag ttcggtgtag gtcgttcgct ccaagctggg ctgtgtgcac    2520
gaaccccccg ttcagcccga ccgctgcgcc ttatccggta actatcgtct tgagtccaac    2580
ccggtaagac acgacttatc gccactggca gcagccactg gtaacaggat tagcagagcg    2640
aggtatgtag gcggtgctac agagttcttg aagtggtggc ctaactacgg ctacactaga    2700
aggacagtat ttggtatctg cgctctgctg aagccagtta ccttcggaaa aagagttggt    2760
agctcttgat ccggcaaaca aaccaccgct ggtagcggtg gttttttttgt ttgcaagcag    2820 cagattacgc gcagaaaaaa aggatctcaa gaagatcctt tgatcttttc tacggggtct    2880
gacgctcagt ggaacgaaaa ctcacgttaa gggattttgg tcatgagatt atcaaaaagg    2940
atcttcacct agatcctttt aaaggccggc cgcggccgcc atcggcattt tcttttgcgt    3000
ttttatttgt taactgttaa ttgtccttgt tcaaggatgc tgtctttgac aacagatgtt    3060
ttcttgcctt tgatgttcag caggaagctc ggcgcaaacg ttgattgttt gtctgcgtag    3120
aatcctctgt ttgtcatata gcttgtaatc acgacattgt ttcctttcgc ttgaggtaca    3180
gcgaagtgtg agtaagtaaa ggttacatcg ttaggatcaa gatccatttt taacacaagg    3240
ccagttttgt tcagcggctt gtatgggcca gttaaagaat tagaaacata accaagcatg    3300
taaatatcgt tagacgtaat gccgtcaatc gtcattttg atccgcggga gtcagtgaac    3360
aggtaccatt tgccgttcat tttaaagacg ttcgcgcgtt caatttcatc tgttactgtg    3420
ttagatgcaa tcagcggttt catcactttt ttcagtgtgt aatcatcgtt tagctcaatc    3480
ataccgagag cgccgtttgc taactcagcc gtgcgttttt tatcgctttg cagaagtttt    3540
tgactttctt gacggaagaa tgatgtgctt ttgccatagt atgctttgtt aaataaagat    3600
tcttcgcctt ggtagccatc ttcagttcca gtgtttgctt caaatactaa gtatttgtgg    3660
cctttatctt ctacgtagtg aggatctctc agcgtatggt tgtcgcctga gctgtagttg    3720
ccttcatcga tgaactgctg tacattttga tacgtttttc cgtcaccgtc aaagattgat    3780
ttataatcct ctacaccgtt gatgttcaaa gagctgtctg atgctgatac gttaacttgt    3840
gcagttgtca gtgtttgttt gccgtaatgt ttaccggaga aatcagtgta gaataaacgg    3900 attttttccgt cagatgtaaa tgtggctgaa cctgaccatt cttgtgtttg gtcttttagg    3960
atagaatcat ttgcatcgaa tttgtcgctg tcttttaaga cgcggccagc gttttttccag    4020 ctgtcaatag aagtttcgcc gacttttttga tagaacatgt aaatcgatgt gtcatccgca    4080
tttttaggat ctccggctaa tgcaaagacg atgtggtagc cgtgatagtt tgcgacagtg    4140
ccgtcagcgt tttgtaatgg ccagctgtcc caaacgtcca ggccttttgc agaagagata    4200
tttttaattg tggacgaatc aaattcagaa acttgatatt tttcattttt ttgctgttca    4260
gggatttgca gcatatcatg gcgtgtaata tgggaaatgc cgtatgtttc cttatatggc    4320
ttttggttcg tttctttcgc aaacgcttga gttgcgcctc ctgccagcag tgcggtagta    4380
aaggttaata ctgttgcttg ttttgcaaac ttttttgatgt tcatcgttca tgtctccttt    4440
tttatgtact gtgttagcgg tctgcttctt ccagccctcc tgtttgaaga tggcaagtta    4500
gttacgcaca ataaaaaaag acctaaaata tgtaaggggt gacgccaaag tatacacttt    4560 gcccttaca catttaggt cttgcctgct ttatcagtaa caaacccgcg cgatttactt    4620
ttcgacctca ttctattaga ctctcgtttg gattgcaact ggtctatttt cctctttttgt    4680 ttgatagaaa atcataaaag gatttgcaga ctacgggcct aaagaactaa aaatctatc    4740 tgtttctttt cattctctgt attttttata gtttctgttg catgggcata aagttgcctt    4800
```

-continued

```
tttaatcaca attcagaaaa tatcataata tctcatttca ctaaataata gtgaacggca     4860
ggtatatgtg atgggttaaa aaggatcggc ggccgctcga                          4900
```

<210> SEQ ID NO 4
<211> LENGTH: 4323
<212> TYPE: DNA
<213> ORGANISM: Artificial Sequence
<220> FEATURE:
<223> OTHER INFORMATION: Description of Artificial Sequence: vector
      pCLiK5MCSntegrativ§acB
<220> FEATURE:
<221> NAME/KEY: misc_feature
<222> LOCATION: (2418)..(3839)
<223> OTHER INFORMATION: coding for levan sucrase (sacB) from Bacillus
      subtilis
<220> FEATURE:
<221> NAME/KEY: promoter
<222> LOCATION: (3840)..(4302)
<223> OTHER INFORMATION: promoter for sacB
<220> FEATURE:
<221> NAME/KEY: misc_feature
<222> LOCATION: (457)..(1248)
<223> OTHER INFORMATION: kanamycin resistance from Tn5
<220> FEATURE:
<221> NAME/KEY: misc_feature
<222> LOCATION: (1515)..(2375)
<223> OTHER INFORMATION: Ori from pMB for replication in E.coli

<400> SEQUENCE: 4

```
tcgagaggcc tgacgtcggg cccggtacca cgcgtcatat gactagttcg gacctaggga      60
tatcgtcgac atcgatgctc ttctgcgtta attaacaatt gggatcctct agacccggga     120
tttaaatcgc tagcgggctg ctaaaggaag cggaacacgt agaaagccag tccgcagaaa     180
cggtgctgac cccggatgaa tgtcagctac tgggctatct ggacaaggga aaacgcaagc     240
gcaaagagaa agcaggtagc ttgcagtggg cttacatggc gatagctaga ctgggcggtt     300
ttatggacag caagcgaacc ggaattgcca gctggggcgc cctctggtaa ggttgggaag     360
ccctgcaaag taaactggat ggctttcttg ccgccaagga tctgatggcg cagggatca     420 agatctgatc aagagacagg atgaggatcg tttcgcatga ttgaacaaga tggattgcac     480
gcaggttctc cggccgcttg ggtggagagg ctattcggct atgactgggc acaacagaca     540
atcggctgct ctgatgccgc cgtgttccgg ctgtcagcgc aggggcgccc ggttcttttt     600
gtcaagaccg acctgtccgg tgccctgaat gaactgcagg acgaggcagc gcggctatcg     660
tggctggcca cgacgggcgt tccttgcgca gctgtgctcg acgttgtcac tgaagcggga     720
agggactggc tgctattggg cgaagtgccg ggcaggatc tcctgtcatc tcaccttgct     780
cctgccgaga agtatccat catggctgat gcaatgcggc ggctgcatac gcttgatccg     840
gctacctgcc cattcgacca ccaagcgaaa catcgcatcg agcgagcacg tactcggatg     900
gaagccggtc ttgtcgatca ggatgatctg gacgaagagc atcaggggct cgcgccagcc     960
gaactgttcg ccaggctcaa ggcgcgcatg cccgacggcg aggatctcgt cgtgacccat    1020
ggcgatgcct gcttgccgaa tatcatggtg gaaaatggcc gcttttctgg attcatcgac    1080
tgtggccggc tgggtgtggc ggaccgctat caggacatag cgttggctac ccgtgatatt    1140
gctgaagagc ttggcggcga atgggctgac cgcttcctcg tgctttacgg tatcgccgct    1200
cccgattcgc agcgcatcgc cttctatcgc cttcttgacg agttcttctg agcgggactc    1260
tggggttcga aatgaccgac caagcgacgc ccaacctgcc atcacgagat ttcgattcca    1320
ccgccgcctt ctatgaaagg ttgggcttcg aatcgttttc cgggacgcc ggctggatga    1380 tcctccagcg cggggatctc atgctggagt tcttcgccca cgctagcggc gcgccggccg    1440
```

```
gcccggtgtg aaataccgca cagatgcgta aggagaaaat accgcatcag gcgctcttcc    1500
gcttcctcgc tcactgactc gctgcgctcg tcgttcggc tgcggcgagc ggtatcagct     1560
cactcaaagg cggtaatacg gttatccaca gaatcagggg ataacgcagg aaagaacatg    1620
tgagcaaaag gccagcaaaa ggccaggaac cgtaaaaagg ccgcgttgct ggcgtttttc    1680
cataggctcc gcccccctga cgagcatcac aaaaatcgac gctcaagtca gaggtggcga    1740
aacccgacag gactataaag ataccaggcg tttccccctg gaagctccct cgtgcgctct    1800
cctgttccga ccctgccgct taccggatac ctgtccgcct ttctcccttc gggaagcgtg    1860
gcgctttctc atagctcacg ctgtaggtat ctcagttcgg tgtaggtcgt tcgctccaag    1920
ctgggctgtg tgcacgaacc ccccgttcag cccgaccgct gcgccttatc cggtaactat    1980
cgtcttgagt ccaacccggt aagacacgac ttatcgccac tggcagcagc cactggtaac    2040
aggattagca gagcgaggta tgtaggcggt gctacagagt tcttgaagtg gtggcctaac    2100
tacggctaca ctagaaggac agtatttggt atctgcgctc tgctgaagcc agttaccttc    2160
ggaaaaagag ttggtagctc ttgatccggc aaacaaacca ccgctggtag cggtggtttt    2220
tttgtttgca agcagcagat tacgcgcaga aaaaaggat ctcaagaaga tcctttgatc    2280
ttttctacgg ggtctgacgc tcagtggaac gaaaactcac gttaagggat tttggtcatg    2340
agattatcaa aaaggatctt cacctagatc cttttaaagg ccggccgcgg ccgccatcgg    2400
cattttcttt tgcgttttta tttgttaact gttaattgtc cttgttcaag gatgctgtct    2460
ttgacaacag atgttttctt gcctttgatg ttcagcagga agctcggcgc aaacgttgat    2520
tgtttgtctg cgtagaatcc tctgtttgtc atatagcttg taatcacgac attgtttcct    2580
ttcgcttgag gtacagcgaa gtgtgagtaa gtaaaggtta catcgttagg atcaagatcc    2640
atttttaaca caaggccagt tttgttcagc ggcttgtatg ggccagttaa agaattagaa    2700
acataaccaa gcatgtaaat atcgttagac gtaatgccgt caatcgtcat ttttgatccg    2760
cgggagtcag tgaacaggta ccatttgccg ttcattttaa agacgttcgc gcgttcaatt    2820
tcatctgtta ctgtgttaga tgcaatcagc ggtttcatca cttttttcag tgtgtaatca    2880
tcgtttagct caatcatacc gagagcgccg tttgctaact cagccgtgcg ttttttatcg    2940
ctttgcagaa gttttgact ttcttgacgg aagaatgatg tgcttttgcc atagtatgct    3000
ttgttaaata aagattcttc gccttggtag ccatcttcag ttccagtgtt tgcttcaaat    3060
actaagtatt tgtggccttt atcttctacg tagtgaggat ctctcagcgt atggttgtcg    3120
cctgagctgt agttgccttc atcgatgaac tgctgtacat tttgatacgt ttttccgtca    3180
ccgtcaaaga ttgatttata atcctctaca ccgttgatgt tcaaagagct gtctgatgct    3240
gatacgttaa cttgtgcagt tgtcagtgtt tgtttgccgt aatgtttacc ggagaaatca    3300
gtgtagaata aacggatttt ccgtcagat gtaaatgtgg ctgaacctga ccattcttgt    3360
gtttggtctt ttaggataga atcatttgca tcgaatttgt cgctgtcttt aaagacgcgg    3420
ccagcgtttt tccagctgtc aatagaagtt tcgccgactt tttgatagaa catgtaaatc    3480
gatgtgtcat ccgcattttt aggatctccg gctaatgcaa agacgatgtg gtagccgtga    3540
tagtttgcga cagtgccgtc agcgttttgt aatggccagc tgtcccaaac gtccaggcct    3600
tttgcagaag agatattttt aattgtggac gaatcaaatt cagaaacttg atattttca    3660
ttttttgct gttcagggat ttgcagcata tcatggcgtg taatatggga aatgccgtat    3720
gtttccttat atggcttttg gttcgtttct ttcgcaaacg cttgagttgc gcctcctgcc    3780
```

```
agcagtgcgg tagtaaaggt taatactgtt gcttgttttg caaacttttt gatgttcatc    3840
gttcatgtct ccttttttat gtactgtgtt agcggtctgc ttcttccagc cctcctgttt    3900
gaagatggca agttagttac gcacaataaa aaaagaccta aaatatgtaa ggggtgacgc    3960
caaagtatac actttgccct ttacacattt taggtcttgc ctgctttatc agtaacaaac    4020
ccgcgcgatt tacttttcga cctcattcta ttagactctc gtttggattg caactggtct    4080
attttcctct tttgtttgat agaaaatcat aaaaggattt gcagactacg ggcctaaaga    4140
actaaaaaat ctatctgttt cttttcattc tctgtatttt ttatagtttc tgttgcatgg    4200
gcataaagtt gcctttttaa tcacaattca gaaaatatca taatatctca tttcactaaa    4260
taatagtgaa cggcaggtat atgtgatggg ttaaaaagga tcggcggccg ctcgatttaa    4320
atc                                                                  4323

<210> SEQ ID NO 5
<211> LENGTH: 828
<212> TYPE: DNA
<213> ORGANISM: Corynebacterium glutamicum
<220> FEATURE:
<221> NAME/KEY: CDS
<222> LOCATION: (101)..(805)
<223> OTHER INFORMATION: coding for positive regulator of methionine
      biosynthesis (RXN02910)

<400> SEQUENCE: 5
aacctaggcc gatacccatg tggaaatctc gacgtcttaa atggacgatt ggagctaaaa      60
ccacgaacag ctgggatttt ccacgatagg attgggtctc gtg gag att cgt tgg     115
                                             Val Glu Ile Arg Trp
                                               1               5 ttg gaa ggc ttt atc gcg gtc gcg gaa gaa ttg cac ttt agt aat gct     163
Leu Glu Gly Phe Ile Ala Val Ala Glu Glu Leu His Phe Ser Asn Ala
             10                  15                  20 gcg att cgt ttg ggg atg ccg caa tcg ccg ttg agt cag ttg atc cgg     211
Ala Ile Arg Leu Gly Met Pro Gln Ser Pro Leu Ser Gln Leu Ile Arg
         25                  30                  35 cgg ttg gag tcg gag ttg ggg cag aag ctt ttt gat cgc agt acc cgg     259
Arg Leu Glu Ser Glu Leu Gly Gln Lys Leu Phe Asp Arg Ser Thr Arg
     40                  45                  50 tcg gtg gag tta act gcc gcg ggt cgg gcg ttt ttg cca cat gcc agg     307
Ser Val Glu Leu Thr Ala Ala Gly Arg Ala Phe Leu Pro His Ala Arg
 55                  60                  65 ggg att gtg gcg agc gct gcg gtg gcg agg gaa gct gtg aat gct gcc     355
Gly Ile Val Ala Ser Ala Ala Val Ala Arg Glu Ala Val Asn Ala Ala
 70                  75                  80                  85 gag ggg gag atc gtt ggt gtt gtt cgc att ggt ttt tct ggt gtg ctg     403
Glu Gly Glu Ile Val Gly Val Val Arg Ile Gly Phe Ser Gly Val Leu
                 90                  95                 100 aac tat tcc acg ctg ccg ctt ttg acc agt gag gtg cat aaa cgg ctt     451
Asn Tyr Ser Thr Leu Pro Leu Leu Thr Ser Glu Val His Lys Arg Leu
            105                 110                 115 cct aat gtg gag ttg gag ctc gtt ggt cag aag ttg acg agg gaa gcg     499
Pro Asn Val Glu Leu Glu Leu Val Gly Gln Lys Leu Thr Arg Glu Ala
        120                 125                 130 gta agt ttg ctg cgc ttg ggg gcg ttg gat att acg ttg atg ggt ttg     547
Val Ser Leu Leu Arg Leu Gly Ala Leu Asp Ile Thr Leu Met Gly Leu
    135                 140                 145 ccc att gag gat cca gag att gag act cgg ctg att agt ttg gaa gag     595
Pro Ile Glu Asp Pro Glu Ile Glu Thr Arg Leu Ile Ser Leu Glu Glu
150                 155                 160                 165
```

-continued

```
ttt tgc gtg gtg ttg ccg aag gat cat cgt ctt gcg ggg gaa gga gtg      643
Phe Cys Val Val Leu Pro Lys Asp His Arg Leu Ala Gly Glu Gly Val
            170                 175                 180 gtg gat ttg gtg gat ctg gct aaa gat ggg ttt gtg acg acg ccg gag      691
Val Asp Leu Val Asp Leu Ala Lys Asp Gly Phe Val Thr Thr Pro Glu
                185                 190                 195 ttt gcg ggg tct gtg ttt agg aat tcc acc ttt cag ttg tgt gct gag      739
Phe Ala Gly Ser Val Phe Arg Asn Ser Thr Phe Gln Leu Cys Ala Glu
        200                 205                 210 gct ggt ttt gtg ccg agg atc agc cag caa gtt aat gat cct tac atg      787
Ala Gly Phe Val Pro Arg Ile Ser Gln Gln Val Asn Asp Pro Tyr Met
    215                 220                 225 gcg ctg ttg ttg gcg cgg tagtcaatca tggggagta tcc                     828
Ala Leu Leu Leu Ala Arg
230             235

<210> SEQ ID NO 6
<211> LENGTH: 235
<212> TYPE: PRT
<213> ORGANISM: Corynebacterium glutamicum

<400> SEQUENCE: 6

Val Glu Ile Arg Trp Leu Glu Gly Phe Ile Ala Val Ala Glu Glu Leu
 1               5                  10                  15

His Phe Ser Asn Ala Ala Ile Arg Leu Gly Met Pro Gln Ser Pro Leu
             20                  25                  30

Ser Gln Leu Ile Arg Arg Leu Glu Ser Glu Leu Gly Gln Lys Leu Phe
         35                  40                  45

Asp Arg Ser Thr Arg Ser Val Glu Leu Thr Ala Ala Gly Arg Ala Phe
     50                  55                  60

Leu Pro His Ala Arg Gly Ile Val Ala Ser Ala Val Ala Arg Glu
 65                  70                  75                  80

Ala Val Asn Ala Ala Glu Gly Glu Ile Val Gly Val Arg Ile Gly
                 85                  90                  95

Phe Ser Gly Val Leu Asn Tyr Ser Thr Leu Pro Leu Leu Thr Ser Glu
            100                 105                 110

Val His Lys Arg Leu Pro Asn Val Glu Leu Glu Leu Val Gly Gln Lys
        115                 120                 125

Leu Thr Arg Glu Ala Val Ser Leu Leu Arg Leu Gly Ala Leu Asp Ile
    130                 135                 140

Thr Leu Met Gly Leu Pro Ile Glu Asp Pro Glu Ile Glu Thr Arg Leu
145                 150                 155                 160

Ile Ser Leu Glu Glu Phe Cys Val Val Leu Pro Lys Asp His Arg Leu
                165                 170                 175

Ala Gly Glu Gly Val Val Asp Leu Val Asp Leu Ala Lys Asp Gly Phe
            180                 185                 190

Val Thr Thr Pro Glu Phe Ala Gly Ser Val Phe Arg Asn Ser Thr Phe
        195                 200                 205

Gln Leu Cys Ala Glu Ala Gly Phe Val Pro Arg Ile Ser Gln Gln Val
    210                 215                 220

Asn Asp Pro Tyr Met Ala Leu Leu Leu Ala Arg
225                 230                 235

<210> SEQ ID NO 7
<211> LENGTH: 34
<212> TYPE: DNA
<213> ORGANISM: Artificial Sequence
<220> FEATURE:
```

```
<223> OTHER INFORMATION: Description of Artificial Sequence:
      oligonucleotide primer
<220> FEATURE:
<221> NAME/KEY: misc_feature
<222> LOCATION: (1)..(34)
<223> OTHER INFORMATION: sense primer

<400> SEQUENCE: 7
gagagactcg agtggtttag gggatgagaa accg                              34

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      oligonucleotide primer
<220> FEATURE:
<221> NAME/KEY: misc_feature
<222> LOCATION: (1)..(31)
<223> OTHER INFORMATION: antisense primer

<400> SEQUENCE: 8
ctctcactag tctaccgcgc aacaacagc g                                 31

<210> SEQ ID NO 9
<211> LENGTH: 990
<212> TYPE: DNA
<213> ORGANISM: Corynebacterium glutamicum
<220> FEATURE:
<221> NAME/KEY: misc_feature
<222> LOCATION: (1)..(12)
<223> OTHER INFORMATION: synthetic linker attached by PCR
<220> FEATURE:
<221> NAME/KEY: misc_feature
<222> LOCATION: (980)..(990)
<223> OTHER INFORMATION: synthetic linker attached by PCR
<220> FEATURE:
<221> NAME/KEY: promoter
<222> LOCATION: (13)..(271)
<223> OTHER INFORMATION: promoter and 5'-untranslated region of rxa02910
      gene
<220> FEATURE:
<221> NAME/KEY: CDS
<222> LOCATION: (272)..(976)
<223> OTHER INFORMATION: coding for positive regulator of methionine
      biosynthesis (rxa02910)

<400> SEQUENCE: 9
gagagactcg agtggtttag gggatgagaa accggacaca cgtgccaaaa cttcggcttt   60
ttcgccaatc ttgtcacgcc tgtctggttt gcctcggatg aggtgattc atggccaaga   120 cttctaaaag ttcgacctcg caggatcgct tctaagggcc tttagcggac caacctaggc   180
cgatacccat gtggaaatct cgacgtctta aatggacgat tggagctaaa accacgaaca   240
gctgggattt ccacgatag gattgggtct c gtg gag att cgt tgg ttg gaa       292
                                 Val Glu Ile Arg Trp Leu Glu
                                  1               5 ggc ttt atc gcg gtc gcg gaa gaa ttg cac ttt agt aat gct gcg att     340
Gly Phe Ile Ala Val Ala Glu Glu Leu His Phe Ser Asn Ala Ala Ile
         10                  15                  20 cgt ttg ggg atg ccg caa tcg ccg ttg agt cag ttg atc cgg cgg ttg     388
Arg Leu Gly Met Pro Gln Ser Pro Leu Ser Gln Leu Ile Arg Arg Leu
     25                  30                  35 gag tcg gag ttg ggg cag aag ctt ttt gat cgc agt acc cgg tcg gtg     436
Glu Ser Glu Leu Gly Gln Lys Leu Phe Asp Arg Ser Thr Arg Ser Val
 40                  45                  50                  55 gag tta act gcc gcg ggt cgg gcg ttt ttg cca cat gcc agg ggg att     484
```

```
                                                            -continued

Glu Leu Thr Ala Ala Gly Arg Ala Phe Leu Pro His Ala Arg Gly Ile
                60                  65                  70 gtg gcg agc gct gcg gtg gcg agg gaa gct gtg aat gct gcc gag ggg      532
Val Ala Ser Ala Ala Val Ala Arg Glu Ala Val Asn Ala Ala Glu Gly
            75                  80                  85 gag atc gtt ggt gtt gtt cgc att ggt ttt tct ggt gtg ctg aac tat      580
Glu Ile Val Gly Val Val Arg Ile Gly Phe Ser Gly Val Leu Asn Tyr
        90                  95                  100 tcc acg ctg ccg ctt ttg acc agt gag gtg cat aaa cgg ctt cct aat      628
Ser Thr Leu Pro Leu Leu Thr Ser Glu Val His Lys Arg Leu Pro Asn
    105                 110                 115 gtg gag ttg gag ctc gtt ggt cag aag ttg acg agg gaa gcg gta agt      676
Val Glu Leu Glu Leu Val Gly Gln Lys Leu Thr Arg Glu Ala Val Ser
120                 125                 130                 135 ttg ctg cgc ttg ggg gcg ttg gat att acg ttg atg ggt ttg ccc att      724
Leu Leu Arg Leu Gly Ala Leu Asp Ile Thr Leu Met Gly Leu Pro Ile
                140                 145                 150 gag gat cca gag att gag act cgg ctg att agt ttg gaa gag ttt tgc      772
Glu Asp Pro Glu Ile Glu Thr Arg Leu Ile Ser Leu Glu Glu Phe Cys
            155                 160                 165 gtg gtg ttg ccg aag gat cat cgt ctt gcg ggg gaa gga gtg gtg gat      820
Val Val Leu Pro Lys Asp His Arg Leu Ala Gly Glu Gly Val Val Asp
        170                 175                 180 ttg gtg gat ctg gct aaa gat ggg ttt gtg acg acg ccg gag ttt gcg      868
Leu Val Asp Leu Ala Lys Asp Gly Phe Val Thr Thr Pro Glu Phe Ala
    185                 190                 195 ggg tct gtg ttt agg aat tcc acc ttt cag ttg tgt gct gag gct ggt      916
Gly Ser Val Phe Arg Asn Ser Thr Phe Gln Leu Cys Ala Glu Ala Gly
200                 205                 210                 215 ttt gtg ccg agg atc agc cag caa gtt aat gat cct tac atg gcg ctg      964
Phe Val Pro Arg Ile Ser Gln Gln Val Asn Asp Pro Tyr Met Ala Leu
                220                 225                 230 ttg ttg gcg cgg tagactagtg agag                                      990
Leu Leu Ala Arg
            235

<210> SEQ ID NO 10
<211> LENGTH: 235
<212> TYPE: PRT
<213> ORGANISM: Corynebacterium glutamicum

<400> SEQUENCE: 10

Val Glu Ile Arg Trp Leu Glu Gly Phe Ile Ala Val Ala Glu Glu Leu
1               5                   10                  15

His Phe Ser Asn Ala Ala Ile Arg Leu Gly Met Pro Gln Ser Pro Leu
            20                  25                  30

Ser Gln Leu Ile Arg Arg Leu Glu Ser Glu Leu Gly Gln Lys Leu Phe
        35                  40                  45

Asp Arg Ser Thr Arg Ser Val Glu Leu Thr Ala Ala Gly Arg Ala Phe
    50                  55                  60

Leu Pro His Ala Arg Gly Ile Val Ala Ser Ala Val Ala Arg Glu
65                  70                  75                  80

Ala Val Asn Ala Ala Glu Gly Glu Ile Val Gly Val Val Arg Ile Gly
                85                  90                  95

Phe Ser Gly Val Leu Asn Tyr Ser Thr Leu Pro Leu Leu Thr Ser Glu
            100                 105                 110

Val His Lys Arg Leu Pro Asn Val Glu Leu Glu Leu Val Gly Gln Lys
        115                 120                 125
```

```
Leu Thr Arg Glu Ala Val Ser Leu Leu Arg Leu Gly Ala Leu Asp Ile
    130                 135                 140

Thr Leu Met Gly Leu Pro Ile Glu Asp Pro Glu Ile Glu Thr Arg Leu
145                 150                 155                 160

Ile Ser Leu Glu Glu Phe Cys Val Val Leu Pro Lys Asp His Arg Leu
                165                 170                 175

Ala Gly Glu Gly Val Val Asp Leu Val Asp Leu Ala Lys Asp Gly Phe
            180                 185                 190

Val Thr Thr Pro Glu Phe Ala Gly Ser Val Phe Arg Asn Ser Thr Phe
        195                 200                 205

Gln Leu Cys Ala Glu Ala Gly Phe Val Pro Arg Ile Ser Gln Gln Val
    210                 215                 220

Asn Asp Pro Tyr Met Ala Leu Leu Leu Ala Arg
225                 230                 235

<210> SEQ ID NO 11
<211> LENGTH: 439
<212> TYPE: DNA
<213> ORGANISM: Artificial Sequence
<220> FEATURE:
<223> OTHER INFORMATION: Description of Artificial Sequence: PCR
      fragment for rxn02910 knock-out

<400> SEQUENCE: 11
tatactcgag ttgatcgcag tacccggtcg gtggagttaa ctgccgcggg tcgggcgttt      60
ttgccacatg ccaggggggat tgtggcgagc gctgcggtgg cgagggaagc tgtgaatgct     120
gccgaggggg agatcgttgg tgttgttcgc attggttttt ctggtgtgct gaactattcc     180
acgctgccgc ttttgaccag tgaggtgcat aaacggcttc ctaatgtgga gttggagctc     240
gttggtcaga agttgacgag ggaagcggta agtttgctgc gcttggggcc gttggatatt     300
acgttgatgg gtttgcccat tgaggatcca gagattgaga ctcggctgat tagtttggaa     360
gagttttgcg tggtgttgcc gaaggatcat cgtcttgcgg gggaaggagt ggtggatttg     420
gtggatctgg atatcagag                                                  439

<210> SEQ ID NO 12
<211> LENGTH: 5156
<212> TYPE: DNA
<213> ORGANISM: Artificial Sequence
<220> FEATURE:
<223> OTHER INFORMATION: Description of Artificial Sequence: vector for
      Corynebacterium glutamicum pG
<220> FEATURE:
<221> NAME/KEY: terminator
<222> LOCATION: (125)..(184)
<223> OTHER INFORMATION: GroEL terminator
<220> FEATURE:
<221> NAME/KEY: misc_feature
<222> LOCATION: (534)..(1325)
<223> OTHER INFORMATION: kanamycin resistance gene from Tn5
<220> FEATURE:
<221> NAME/KEY: misc_feature
<222> LOCATION: (3606)..(4727)
<223> OTHER INFORMATION: Rep gene for replication in C.glutamicum
<220> FEATURE:
<221> NAME/KEY: misc_feature
<222> LOCATION: (2598)..(3272)
<223> OTHER INFORMATION: ORF1 for replication in C.glutamicum
<220> FEATURE:
<221> NAME/KEY: misc_feature
<222> LOCATION: (1592)..(2452)
<223> OTHER INFORMATION: Ori from pMB for replication in E.coli

<400> SEQUENCE: 12
```

```
tcgatttaaa tctcgagagg cctgacgtcg ggcccggtac cacgcgtcat atgactagtt    60
cggacctagg gatatcgtcg acatcgatgc tcttctgcgt taattaacaa ttgggatcct   120
ctagagttct gtgaaaaaca ccgtggggca gtttctgctt cgcggtgttt tttatttgtg   180
gggcactaga cccgggattt aaatcgctag cgggctgcta aggaagcgg aacacgtaga    240 aagccagtcc gcagaaacgg tgctgacccc ggatgaatgt cagctactgg gctatctgga   300
caagggaaaa cgcaagcgca aagagaaagc aggtagcttg cagtgggctt acatggcgat   360
agctagactg ggcggtttta tggacagcaa gcgaaccgga attgccagct ggggcgccct   420
ctggtaaggt tgggaagccc tgcaaagtaa actggatggc tttcttgccg ccaaggatct   480
gatggcgcag gggatcaaga tctgatcaag agacaggatg aggatcgttt cgcatgattg   540
aacaagatgg attgcacgca ggttctccgg ccgcttgggt ggagaggcta ttcggctatg   600
actgggcaca acagacaatc ggctgctctg atgccgccgt gttccggctg tcagcgcagg   660
ggcgcccggt tctttttgtc aagaccgacc tgtccggtgc cctgaatgaa ctgcaggacg   720
aggcagcgcg gctatcgtgg ctggccacga cgggcgttcc ttgcgcagct gtgctcgacg   780
ttgtcactga agcgggaagg gactggctgc tattgggcga agtgccgggg caggatctcc   840
tgtcatctca ccttgctcct gccgagaaag tatccatcat ggctgatgca atgcggcggc   900
tgcatacgct tgatccggct acctgcccat tcgaccacca agcgaaacat cgcatcgagc   960
gagcacgtac tcggatggaa gccggtcttg tcgatcagga tgatctggac gaagagcatc  1020 agggctcgc gccagccgaa ctgttcgcca ggctcaaggc gcgcatgccc gacggcgagg  1080
atctcgtcgt gacccatggc gatgcctgct tgccgaatat catggtggaa aatggccgct  1140
tttctggatt catcgactgt ggccggctgg gtgtggcgga ccgctatcag gacatagcgt  1200
tggctacccg tgatattgct gaagagcttg gcggcgaatg ggctgaccgc ttcctcgtgc  1260
tttacggtat cgccgctccc gattcgcagc gcatcgcctt ctatcgcctt cttgacgagt  1320
tcttctgagc gggactctgg ggttcgaaat gaccgaccaa gcgacgccca acctgccatc  1380
acgagatttc gattccaccg ccgccttcta tgaaaggttg gccttcggaa tcgttttccg  1440
ggacgccggc tggatgatcc tccagcgcgg ggatctcatg ctggagttct cgcccacgc   1500 tagcggcgcg ccggccggcc cggtgtgaaa taccgcacag atgcgtaagg agaaaatacc  1560
gcatcaggcg ctcttccgct tcctcgctca ctgactcgct gcgctcggtc gttcggctgc  1620
ggcgagcggt atcagctcac tcaaaggcgg taatacggtt atccacagaa tcaggggata  1680
acgcaggaaa gaacatgtga gcaaaaggcc agcaaaaggc caggaaccgt aaaaaggccg  1740
cgttgctggc gttttccat aggctccgcc cccctgacga gcatcacaaa aatcgacgct  1800
caagtcagag gtggcgaaac ccgacaggac tataaagata ccaggcgttt ccccctggaa  1860
gctccctcgt gcgctctcct gttccgaccc tgccgcttac cggatacctg tccgcctttc  1920
tcccttcggg aagcgtggcg ctttctcata gctcacgctg taggtatctc agttcggtgt  1980
aggtcgttcg ctccaagctg ggctgtgtgc acgaaccccc cgttcagccc gaccgctgcg  2040
ccttatccgg taactatcgt cttgagtcca acccggtaag acacgactta tcgccactgg  2100
cagcagccac tggtaacagg attagcagag cgaggtatgt aggcggtgct acagagttct  2160
tgaagtggtg gcctaactac ggctacacta gaaggacagt atttggtatc tgcgctctgc  2220
tgaagccagt taccttcgga aaaagagttg gtagctcttg atccggcaaa caaaccaccg  2280
ctggtagcgg tggttttttt gtttgcaagc agcagattac gcgcagaaaa aaaggatctc  2340
aagaagatcc tttgatcttt tctacggggt ctgacgctca gtggaacgaa aactcacgtt  2400
```

```
aagggatttt ggtcatgaga ttatcaaaaa ggatcttcac ctagatcctt ttaaaggccg    2460
gccgcggccg cgcaaagtcc cgcttcgtga aaattttcgt gccgcgtgat tttccgccaa    2520
aaactttaac gaacgttcgt tataatggtg tcatgacctt cacgacgaag tactaaaatt    2580
ggcccgaatc atcagctatg gatctctctg atgtcgcgct ggagtccgac gcgctcgatg    2640
ctgccgtcga tttaaaaacg gtgatcggat ttttccgagc tctcgatacg acggacgcgc    2700
cagcatcacg agactgggcc agtgccgcga gcgacctaga aactctcgtg gcggatcttg    2760
aggagctggc tgacgagctg cgtgctcggc cagcgccagg aggacgcaca gtagtggagg    2820
atgcaatcag ttgcgcctac tgcggtggcc tgattcctcc ccggcctgac ccgcgaggac    2880
ggcgcgcaaa atattgctca gatgcgtgtc gtgccgcagc cagccgcgag cgcgccaaca    2940
aacgccacgc cgaggagctg gaggcggcta ggtcgcaaat ggcgctggaa gtgcgtcccc    3000
cgagcgaaat tttggccatg gtcgtcacag agctggaagc ggcagcgaga attatcgcga    3060
tcgtggcggt gcccgcaggc atgacaaaca tcgtaaatgc cgcgtttcgt gtgccgtggc    3120
cgcccaggac gtgtcagcgc cgccaccacc tgcaccgaat cggcagcagc gtcgcgcgtc    3180
gaaaaagcgc acaggcggca agaagcgata agctgcacga atacctgaaa aatgttgaac    3240
gccccgtgag cggtaactca cagggcgtcg gctaaccccc agtccaaacc tgggagaaag    3300
cgctcaaaaa tgactctagc ggattcacga gacattgaca caccggcctg gaaattttcc    3360
gctgatctgt tcgacaccca tcccgagctc gcgctgcgat cacgtggctg gacgagcgaa    3420
gaccgccgcg aattcctcgc tcacctgggc agagaaaatt tccagggcag caagacccgc    3480
gacttcgcca gcgcttggat caaagacccg gacacggaga acacagccg aagttatacc    3540 gagttggttc aaaatcgctt gcccggtgcc agtatgttgc tctgacgcac gcgcagcacg    3600
cagccgtgct tgtcctggac attgatgtgc cgagccacca ggccggcggg aaaatcgagc    3660
acgtaaaccc cgaggtctac gcgattttgg agcgctgggc acgcctggaa aaagcgccag    3720
cttggatcgg cgtgaatcca ctgagcggga aatgccagct catctggctc attgatccgg    3780
tgtatgccgc agcaggcatg agcagcccga atatgcgcct gctggctgca acgaccgagg    3840
aaatgacccg cgttttcggc gctgaccagg cttttttcaca taggctgagc cgtggccact    3900
gcactctccg acgatcccag ccgtaccgct ggcatgccca gcacaatcgc gtggatcgcc    3960
tagctgatct tatggaggtt gctcgcatga tctcaggcac agaaaaacct aaaaaacgct    4020
atgagcagga gttttctagc ggacgggcac gtatcgaagc ggcaagaaaa gccactgcgg    4080
aagcaaaagc acttgccacg cttgaagcaa gcctgccgag cgccgctgaa gcgtctggag    4140
agctgatcga cggcgtccgt gtcctctgga ctgctccagg gcgtgccgcc cgtgatgaga    4200
cggcttttcg ccacgctttg actgtgggat accagttaaa agcggctggt gagcgcctaa    4260
aagacaccaa gggtcatcga gcctacgagc gtgcctacac cgtcgctcag gcggtcggag    4320
gaggccgtga gcctgatctg ccgccggact gtgaccgcca gacggattgg ccgcgacgtg    4380
tgcgcggcta cgtcgctaaa ggccagccag tcgtccctgc tcgtcagaca gagacgcaga    4440
gccagccgag gcgaaaagct ctggccacta tgggaagacg tggcggtaaa aaggccgcag    4500
aacgctggaa agacccaaac agtgagtacg cccgagcaca gcgagaaaaa ctagctaagt    4560
ccagtcaacg acaagctagg aaagctaaag gaaatcgctt gaccattgca ggttggttta    4620
tgactgttga gggagagact ggctcgtggc cgacaatcaa tgaagctatg tctgaattta    4680
gcgtgtcacg tcagaccgtg aatagagcac ttaaggtctg cgggcattga acttccacga    4740
```

| | |
|---|---|
| ggacgccgaa agcttcccag taaatgtgcc atctcgtagg cagaaaacgg ttccccgta | 4800 |
| gggtctctct cttggcctcc tttctaggtc gggctgattg ctcttgaagc tctctagggg | 4860 |
| ggctcacacc ataggcagat aacgttcccc accggctcgc ctcgtaagcg cacaaggact | 4920 |
| gctcccaaag atcttcaaag ccactgccgc gactgccttc gcgaagcctt gccccgcgga | 4980 |
| aatttcctcc accgagttcg tgcacacccc tatgccaagc ttctttcacc ctaaattcga | 5040 |
| gagattggat tcttaccgtg gaaattcttc gcaaaaatcg tccccctgatc gcccttgcga | 5100 |
| cgttggcgtc ggtgccgctg gttgcgcttg gcttgaccga cttgatcagc ggccgc | 5156 |

```
<210> SEQ ID NO 13
<211> LENGTH: 6087
<212> TYPE: DNA
<213> ORGANISM: Artificial Sequence
<220> FEATURE:
<223> OTHER INFORMATION: Description of Artificial Sequence: vector
      pGrxb2010 for overexpression ofpositive regulator
      of methionine biosynthesis (rxn2910)
<220> FEATURE:
<221> NAME/KEY: misc_feature
<222> LOCATION: (1465)..(2256)
<223> OTHER INFORMATION: kanamycin resistance from Tn5
<220> FEATURE:
<221> NAME/KEY: misc_difference
<222> LOCATION: (3529)..(4203)
<223> OTHER INFORMATION: Orf1 for replication in C.glutamicum
<220> FEATURE:
<221> NAME/KEY: misc_feature
<222> LOCATION: (4537)..(5658)
<223> OTHER INFORMATION: Rep gene for replication in C.glutamicum
<220> FEATURE:
<221> NAME/KEY: misc_feature
<222> LOCATION: (2523)..(3383)
<223> OTHER INFORMATION: Ori from pMB for replication in E.coli
<220> FEATURE:
<221> NAME/KEY: terminator
<222> LOCATION: (1056)..(1115)
<223> OTHER INFORMATION: GroEl terminator from C.glutamicum
<220> FEATURE:
<221> NAME/KEY: misc_feature
<222> LOCATION: (268)..(984)
<223> OTHER INFORMATION: coding for rxn02910
<220> FEATURE:
<221> NAME/KEY: promoter
<222> LOCATION: (19)..(267)
<223> OTHER INFORMATION: promoter of rxn02910 gene

<400> SEQUENCE: 13
```

| | |
|---|---|
| tcgatttaaa tctcgagtgg tttaggggat gagaaaccgg acacacgtgc caaaacttcg | 60 |
| gcttttttcgc caatcttgtc acgcctgtct ggtttgcctc ggatgaggtg atttcatggc | 120 |
| caagacttct aaaagttcga cctcgcagga tcgcttctaa gggcctttag cggaccaacc | 180 |
| taggccgata cccatgtgga aatctcgacg tcttaaatgg acgattggag ctaaaaccac | 240 |
| gaacagctgg gattttccac gataggattg ggtctcgtgg agattcgttg gttggaaggc | 300 |
| tttatcgcgg tcgcggaaga attgcacttt agtaatgctg cgattcgttt ggggatgccg | 360 |
| caatcgccgt tgagtcagtt gatccggcgg ttggagtcgg agttggggca gaagcttttt | 420 |
| gatcgcagta cccggtcggt ggagttaact gccgcgggtc gggcgttttt gccacatgcc | 480 |
| agggggattg tggcgagcgc tgcggtggcg agggaagctg tgaatgctgc cgagggggag | 540 |
| atcgttggtg ttgttcgcat tggttttttct ggtgtgctga actattccac gctgccgctt | 600 |
| ttgaccagtg aggtgcataa acggcttcct aatgtggagt tggagctcgt tggtcagaag | 660 |
| ttgacgaggg aagcggtaag tttgctgcgc tggggggcgt tggatattac gttgatgggt | 720 |
| ttgcccattg aggatccaga gattgagact cggctgatta gtttggaaga gttttgcgtg | 780 |

```
gtgttgccga aggatcatcg tcttgcgggg gaaggagtgg tggatttggt ggatctggct     840
aaagatgggt ttgtgacgac gccggagttt gcggggtctg tgtttaggaa ttccacctt     900
cagttgtgtg ctgaggctgg ttttgtgccg aggatcagcc agcaagttaa tgatccttac    960
atggcgctgt tgttggcgcg gtagactagt tcggacctag ggatatcgtc gacatcgatg   1020
ctcttctgcg ttaattaaca attgggatcc tctagagttc tgtgaaaaac accgtggggc   1080
agtttctgct tcgcggtgtt ttttatttgt ggggcactag acccgggatt taaatcgcta   1140
gcgggctgct aaaggaagcg gaacacgtag aaagccagtc cgcagaaacg gtgctgaccc   1200
cggatgaatg tcagctactg ggctatctgg acaagggaaa acgcaagcgc aaagagaaag   1260
caggtagctt gcagtgggct tacatggcga tagctagact gggcggtttt atggacagca   1320
agcgaaccgg aattgccagc tggggcgccc tctggtaagg ttgggaagcc ctgcaaagta   1380
aactggatgg ctttcttgcc gccaaggatc tgatggcgca ggggatcaag atctgatcaa   1440
gagacaggat gaggatcgtt tcgcatgatt gaacaagatg gattgcacgc aggttctccg   1500
gccgcttggg tggagaggct attcggctat gactgggcac aacagacaat cggctgctct   1560
gatgccgccg tgttccggct gtcagcgcag gggcgcccgg ttcttttgt caagaccgac    1620
ctgtccggtg ccctgaatga actgcaggac gaggcagcgc ggctatcgtg gctggccacg   1680
acgggcgttc cttgcgcagc tgtgctcgac gttgtcactg aagcgggaag ggactggctg   1740
ctattgggcg aagtgccggg gcaggatctc ctgtcatctc accttgctcc tgccgagaaa   1800
gtatccatca tggctgatgc aatgcggcgg ctgcatacgc ttgatccggc tacctgccca   1860
ttcgaccacc aagcgaaaca tcgcatcgag cgagcacgta ctcggatgga agccggtctt   1920
gtcgatcagg atgatctgga cgaagagcat caggggctcg cgccagccga actgttcgcc   1980
aggctcaagg cgcgcatgcc cgacggcgag gatctcgtcg tgacccatgg cgatgcctgc   2040
ttgccgaata tcatggtgga aaatggccgc ttttctggat tcatcgactg tggccggctg   2100
ggtgtggcgg accgctatca ggacatagcg ttggctaccc gtgatattgc tgaagagctt   2160
ggcggcgaat gggctgaccg cttcctcgtg ctttacggta tcgccgctcc cgattcgcag   2220
cgcatcgcct tctatcgcct tcttgacgag ttcttctgag cgggactctg gggttcgaaa   2280
tgaccgacca agcgacgccc aacctgccat cacgagattt cgattccacc gccgccttct   2340
atgaaaggtt gggcttcgga atcgttttcc gggacgccgg ctggatgatc ctccagcgcg   2400
gggatctcat gctggagttc ttcgcccacg ctagcggcgc gccggccggc ccggtgtgaa   2460
ataccgcaca gatgcgtaag gagaaaatac cgcatcaggc gctcttccgc ttcctcgctc   2520
actgactcgc tgcgctcggt cgttcggctg cggcgagcgg tatcagctca ctcaaaggcg   2580
gtaatacggt tatccacaga atcaggggat aacgcaggaa agaacatgtg agcaaaaggc   2640
cagcaaaagg ccaggaaccg taaaaaggcc gcgttgctgg cgtttttcca taggctccgc   2700
cccccctgacg agcatcacaa aaatcgacgc tcaagtcaga ggtggcgaaa cccgacagga   2760
ctataaagat accaggcgtt tcccctggaa gctccctcg tgcgctctcc tgttccgacc    2820
ctgccgctta ccggatacct gtccgccttt ctcccttcgg gaagcgtggc gctttctcat   2880
agctcacgct gtaggtatct cagttcggtg taggtcgttc gctccaagct gggctgtgtg   2940
cacgaacccc ccgttcagcc cgaccgctgc gccttatccg gtaactatcg tcttgagtcc   3000
aacccggtaa gacacgactt atcgccactg gcagcagcca ctggtaacag gattagcaga   3060
gcgaggtatg taggcggtgc tacagagttc ttgaagtggt ggcctaacta cggctacact   3120
```

```
agaaggacag tatttggtat ctgcgctctg ctgaagccag ttaccttcgg aaaaagagtt   3180
ggtagctctt gatccggcaa acaaaccacc gctggtagcg gtggttttttt tgtttgcaag   3240 cagcagatta cgcgcagaaa aaaaggatct caagaagatc ctttgatctt ttctacgggg   3300
tctgacgctc agtggaacga aaactcacgt taagggattt tggtcatgag attatcaaaa   3360
aggatcttca cctagatcct tttaaaggcc ggccgcggcc gcgcaaagtc ccgcttcgtg   3420
aaaattttcg tgccgcgtga ttttccgcca aaaactttaa cgaacgttcg ttataatggt   3480
gtcatgacct tcacgacgaa gtactaaaat tgggcccgaat catcagctat ggatctctct   3540
gatgtcgcgc tggagtccga cgcgctcgat gctgccgtcg atttaaaaac ggtgatcgga   3600
tttttccgag ctctcgatac gacggacgcg ccagcatcac gagactgggc cagtgccgcg   3660
agcgacctag aaactctcgt ggcggatctt gaggagctgg ctgacgagct gcgtgctcgg   3720
ccagcgccag gaggacgcac agtagtggag gatgcaatca gttgcgccta ctgcggtggc   3780
ctgattcctc cccggcctga cccgcgagga cggcgcgcaa aatattgctc agatgcgtgt   3840
cgtgccgcag ccagccgcga gcgcgccaac aaacgccacg ccgaggagct ggaggcggct   3900
aggtcgcaaa tggcgctgga agtgcgtccc ccgagcgaaa ttttggccat ggtcgtcaca   3960
gagctggaag cggcagcgag aattatcgcg atcgtggcgg tgcccgcagg catgacaaac   4020
atcgtaaatg ccgcgtttcg tgtgccgtgg ccgcccagga cgtgtcagcg ccgccaccac   4080
ctgcaccgaa tcggcagcag cgtcgcgcgt cgaaaaagcg cacaggcggc aagaagcgat   4140
aagctgcacg aatacctgaa aaatgttgaa cgccccgtga gcggtaactc acagggcgtc   4200
ggctaacccc cagtccaaac ctgggagaaa gcgctcaaaa atgactctag cggattcacg   4260
agacattgac acaccggcct ggaaattttc cgctgatctg ttcgacaccc atcccgagct   4320
cgcgctgcga tcacgtggct ggacgagcga agaccgccgc gaattcctcg ctcacctggg   4380
cagagaaaat ttccagggca gcaagacccg cgacttcgcc agcgcttgga tcaaagaccc   4440
ggacacggag aaacacagcc gaagttatac cgagttggtt caaaatcgct tgcccggtgc   4500
cagtatgttg ctctgacgca cgcgcagcac gcagccgtgc ttgtcctgga cattgatgtg   4560
ccgagccacc aggccggcgg gaaaatcgag cacgtaaacc ccgaggtcta cgcgattttg   4620
gagcgctggg cacgcctgga aaaagcgcca gcttggatcg gcgtgaatcc actgagcggg   4680
aaatgccagc tcatctggct cattgatccg gtgtatgccg cagcaggcat gagcagcccg   4740
aatatgcgcc tgctggctgc aacgaccgag gaaatgaccc gcgttttcgg cgctgaccag   4800 gcttttttcac ataggctgag ccgtggccac tgcactctcc gacgatccca gccgtaccgc   4860
tggcatgccc agcacaatcg cgtggatcgc ctagctgatc ttatggaggt tgctcgcatg   4920
atctcaggca cagaaaaacc taaaaaacgc tatgagcagg agttttctag cggacgggca   4980
cgtatcgaag cggcaagaaa agccactgcg gaagcaaaag cacttgccac gcttgaagca   5040
agcctgccga gcgccgctga agcgtctgga gagctgatcg acggcgtccg tgtcctctgg   5100
actgctccag ggcgtgccgc ccgtgatgag acggcttttc gccacgcttt gactgtggga   5160
taccagttaa aagcggctgg tgagcgccta aagacacca agggtcatcg agcctacgag   5220
cgtgcctaca ccgtcgctca ggcggtcgga ggaggccgtg agcctgatct gccgccggac   5280
tgtgaccgcc agacggattg gccgcgacgt gtgcgcggct acgtcgctaa aggccagcca   5340
gtcgtccctg ctcgtcagac agagacgcag agccagccga ggcgaaaagc tctggccact   5400
atgggaagac gtggcggtaa aaaggccgca gaacgctgga agacccaaa cagtgagtac   5460 gcccgagcac agcgagaaaa actagctaag tccagtcaac gacaagctag gaaagctaaa   5520
```

```
ggaaatcgct tgaccattgc aggttggttt atgactgttg agggagagac tggctcgtgg    5580
ccgacaatca atgaagctat gtctgaattt agcgtgtcac gtcagaccgt gaatagagca    5640
cttaaggtct gcgggcattg aacttccacg aggacgccga aagcttccca gtaaatgtgc    5700
catctcgtag gcagaaaacg gttcccccgt agggtctctc tcttggcctc ctttctaggt    5760
cgggctgatt gctcttgaag ctctctaggg gggctcacac cataggcaga taacgttccc    5820
caccggctcg cctcgtaagc gcacaaggac tgctcccaaa gatcttcaaa gccactgccg    5880
cgactgcctt cgcgaagcct tgccccgcgg aaatttcctc caccgagttc gtgcacaccc    5940
ctatgccaag cttctttcac cctaaattcg agagattgga ttcttaccgt ggaaattctt    6000
cgcaaaaatc gtcccctgat cgccttgcg acgttggcgt cggtgccgct ggttgcgctt     6060
ggcttgaccg acttgatcag cggccgc                                       6087
```

<210> SEQ ID NO 14
<211> LENGTH: 2406
<212> TYPE: DNA
<213> ORGANISM: Artificial Sequence
<220> FEATURE:
<223> OTHER INFORMATION: Description of Artificial Sequence: vector pINTEGRATIV
<220> FEATURE:
<221> NAME/KEY: misc_feature
<222> LOCATION: (457)..(1248)
<223> OTHER INFORMATION: kanamycin resistance gene from Tn5
<220> FEATURE:
<221> NAME/KEY: misc_feature
<222> LOCATION: (1515)..(2375)
<223> OTHER INFORMATION: Ori from pMB for replication in E.coli

<400> SEQUENCE: 14

```
tcgagaggcc tgacgtcggg cccggtacca cgcgtcatat gactagttcg gacctaggga      60
tatcgtcgac atcgatgctc ttctgcgtta attaacaatt gggatcctct agacccggga     120
tttaaatcgc tagcgggctg ctaaaggaag cggaacacgt agaaagccag tccgcagaaa     180
cggtgctgac cccggatgaa tgtcagctac tgggctatct ggacaaggga aaacgcaagc     240
gcaaagagaa agcaggtagc ttgcagtggg cttacatggc gatagctaga ctgggcggtt     300
ttatggacag caagcgaacc ggaattgcca gctggggcgc cctctggtaa ggttgggaag     360
ccctgcaaag taaactggat ggcttcttg ccgccaagga tctgatggcg caggggatca      420
agatctgatc aagagacagg atgaggatcg tttcgcatga ttgaacaaga tggattgcac     480
gcaggttctc cggccgcttg ggtggagagg ctattcggct atgactgggc acaacagaca     540
atcggctgct ctgatgccgc cgtgttccgg ctgtcagcgc aggggcgccc ggttcttttt     600
gtcaagaccg acctgtccgg tgccctgaat gaactgcagg acgaggcagc gcggctatcg     660
tggctggcca cgacgggcgt tccttgcgca gctgtgctcg acgttgtcac tgaagcggga     720
agggactggc tgctattggg cgaagtgccg gggcaggatc tcctgtcatc tcaccttgct     780
cctgccgaga aagtatccat catggctgat gcaatgcggc ggctgcatac gcttgatccg     840
gctacctgcc cattcgacca ccaagcgaaa catcgcatcg agcgagcacg tactcggatg     900
gaagccggtc ttgtcgatca ggatgatctg gacgaagagc atcaggggct cgcgccagcc     960
gaactgttcg ccaggctcaa ggcgcgcatg cccgacggcg aggatctcgt cgtgacccat    1020
ggcgatgcct gcttgccgaa tatcatggtg gaaaatggcc gcttttctgg attcatcgac    1080
tgtggccggc tgggtgtggc ggaccgctat caggacatag cgttggctac ccgtgatatt    1140
gctgaagagc ttggcggcga atgggctgac cgcttcctcg tgctttacgg tatcgccgct    1200
```

```
cccgattcgc agcgcatcgc cttctatcgc cttcttgacg agttcttctg agcgggactc   1260
tggggttcga atgaccgac caagcgacgc ccaacctgcc atcacgagat ttcgattcca   1320
ccgccgcctt ctatgaaagg ttgggcttcg gaatcgtttt ccgggacgcc ggctggatga   1380
tcctccagcg cggggatctc atgctggagt tcttcgccca cgctagcggc gcgccggccg   1440
gcccggtgtg aaataccgca cagatgcgta aggagaaaat accgcatcag gcgctcttcc   1500
gcttcctcgc tcactgactc gctgcgctcg tcgttcggc tgcggcgagc ggtatcagct   1560
cactcaaagg cggtaatacg gttatccaca gaatcagggg ataacgcagg aaagaacatg   1620
tgagcaaaag gccagcaaaa ggccaggaac cgtaaaaagg ccgcgttgct ggcgtttttc   1680
cataggctcc gccccctga cgagcatcac aaaaatcgac gctcaagtca gaggtggcga   1740
aacccgacag gactataaag ataccaggcg tttccccctg gaagctccct cgtgcgctct   1800
cctgttccga ccctgccgct taccggatac ctgtccgcct ttctcccttc gggaagcgtg   1860
gcgctttctc atagctcacg ctgtaggtat ctcagttcgg tgtaggtcgt tcgctccaag   1920
ctgggctgtg tgcacgaacc ccccgttcag cccgaccgct gcgccttatc cggtaactat   1980
cgtcttgagt ccaacccggt aagacacgac ttatcgccac tggcagcagc cactggtaac   2040
aggattagca gagcgaggta tgtaggcggt gctacagagt tcttgaagtg gtggcctaac   2100
tacggctaca ctagaaggac agtatttggt atctgcgctc tgctgaagcc agttaccttc   2160
ggaaaaagag ttggtagctc ttgatccggc aaacaaacca ccgctggtag cggtggtttt   2220
tttgtttgca agcagcagat tacgcgcaga aaaaaggat ctcaagaaga tcctttgatc   2280
ttttctacgg ggtctgacgc tcagtggaac gaaaactcac gttaagggat tttggtcatg   2340
agattatcaa aaaggatctt cacctagatc cttttaaagg ccggccgcgg ccgctcgatt   2400
taaatc                                                             2406
```

<210> SEQ ID NO 15  
<211> LENGTH: 2772  
<212> TYPE: DNA  
<213> ORGANISM: Artificial Sequence  
<220> FEATURE:  
<223> OTHER INFORMATION: Description of Artificial Sequence: vector
    pINTEGRATIV_deltaRXA02910 for knock-out of
    positive regulator of methionine biosynthesis
    rxa02910  
<220> FEATURE:  
<221> NAME/KEY: misc_feature  
<222> LOCATION: (457)..(1248)  
<223> OTHER INFORMATION: kanamcyin resistance gene form Tn5  
<220> FEATURE:  
<221> NAME/KEY: misc_feature  
<222> LOCATION: (1515)..(2375)  
<223> OTHER INFORMATION: Ori from pMB for replication in E.coli  
<220> FEATURE:  
<221> NAME/KEY: misc_feature  
<222> LOCATION: (1)..(61)  
<223> OTHER INFORMATION: fragment of rxa02910 (cont. from bp 2772 in
    circular plasmid)  
<220> FEATURE:  
<221> NAME/KEY: misc_feature  
<222> LOCATION: (2407)..(2772)  
<223> OTHER INFORMATION: fragment of rxa02910 (1st part to be con. from
    bp 1 to 61 in circular plasmid)

<400> SEQUENCE: 15

```
ggtgttgccg aaggatcatc gtcttgcggg ggaaggagtg gtggatttgg tggatctgga     60
tatcgtcgac atcgatgctc ttctgcgtta attaacaatt gggatcctct agacccggga    120
tttaaatcgc tagcgggctg ctaaaggaag cggaacacgt agaaagccag tccgcagaaa    180
```

-continued

```
cggtgctgac cccggatgaa tgtcagctac tgggctatct ggacaaggga aaacgcaagc    240
gcaaagagaa agcaggtagc ttgcagtggg cttacatggc gatagctaga ctgggcggtt    300
ttatggacag caagcgaacc ggaattgcca gctggggcgc cctctggtaa ggttgggaag    360
ccctgcaaag taaactggat ggcttcttg ccgccaagga tctgatggcg cagggatca     420 agatctgatc aagagacagg atgaggatcg tttcgcatga ttgaacaaga tggattgcac    480
gcaggttctc cggccgcttg ggtggagagg ctattcggct atgactgggc acaacagaca    540
atcggctgct ctgatgccgc cgtgttccgg ctgtcagcgc aggggcgccc ggttcttttt    600
gtcaagaccg acctgtccgg tgccctgaat gaactgcagg acgaggcagc gcggctatcg    660
tggctggcca cgacgggcgt tccttgcgca gctgtgctcg acgttgtcac tgaagcggga    720
agggactggc tgctattggg cgaagtgccg gggcaggatc tcctgtcatc tcaccttgct    780
cctgccgaga agtatccat catggctgat gcaatgcggc ggctgcatac gcttgatccg    840
gctacctgcc cattcgacca ccaagcgaaa catcgcatcg agcgagcacg tactcggatg    900
gaagccggtc ttgtcgatca ggatgatctg gacgaagagc atcaggggct cgcgccagcc    960
gaactgttcg ccaggctcaa ggcgcgcatg cccgacggcg aggatctcgt cgtgacccat   1020
ggcgatgcct gcttgccgaa tatcatggtg gaaaatggcc gcttttctgg attcatcgac   1080
tgtggccggc tgggtgtggc ggaccgctat caggacatag cgttggctac ccgtgatatt   1140
gctgaagagc ttggcggcga atgggctgac cgcttcctcg tgctttacgg tatcgccgct   1200
cccgattcgc agcgcatcgc cttctatcgc cttcttgacg agttcttctg agcgggactc   1260
tggggttcga atgaccgac caagcgacgc ccaacctgcc atcacgagat ttcgattcca   1320
ccgccgcctt ctatgaaagg ttgggcttcg gaatcgtttt ccgggacgcc ggctggatga   1380
tcctccagcg cggggatctc atgctggagt tcttcgccca cgctagcggc gcgccggccg   1440
gcccggtgtg aaataccgca cagatgcgta aggagaaaat accgcatcag cgctcttcc    1500 gcttcctcgc tcactgactc gctgcgctcg gtcgttcggc tgcggcgagc ggtatcagct   1560
cactcaaagg cggtaatacg gttatccaca gaatcagggg ataacgcagg aaagaacatg   1620
tgagcaaaag gccagcaaaa ggccaggaac cgtaaaaagg ccgcgttgct ggcgtttttc   1680
cataggctcc gccccctga cgagcatcac aaaatcgac gctcaagtca gaggtggcga   1740
aacccgacag gactataaag ataccaggcg tttccccctg gaagctccct cgtgcgctct   1800
cctgttccga ccctgccgct taccggatac ctgtccgcct ttctcccttc gggaagcgtg   1860
gcgctttctc atagctcacg ctgtaggtat ctcagttcgg tgtaggtcgt tcgctccaag   1920
ctgggctgtg tgcacgaacc ccccgttcag cccgaccgct gcgccttatc cggtaactat   1980
cgtcttgagt ccaacccggt aagacacgac ttatcgccac tggcagcagc cactggtaac   2040
aggattagca gagcgaggta tgtaggcggt gctacagagt tcttgaagtg gtggcctaac   2100
tacggctaca ctagaaggac agtatttggt atctgcgctc tgctgaagcc agttaccttc   2160
ggaaaaagag ttggtagctc ttgatccggc aaacaaacca ccgctggtag cggtggtttt   2220
tttgtttgca agcagcagat tacgcgcaga aaaaaggat ctcaagaaga tcctttgatc    2280
ttttctacgg ggtctgacgc tcagtggaac gaaaactcac gttaagggat tttggtcatg   2340
agattatcaa aaaggatctt cacctagatc cttttaaagg ccgccgcgg ccgctcgatt    2400 taaatctcga gttgatcgca gtacccggtc ggtggagtta actgccgcgg gtcgggcgtt   2460
tttgccacat gccaggggga ttgtggcgag cgctgcggtg gcgagggaag ctgtgaatgc   2520
```

-continued

```
tgccgagggg gagatcgttg gtgttgttcg cattggtttt tctggtgtgc tgaactattc    2580
cacgctgccg cttttgacca gtgaggtgca taaacggctt cctaatgtgg agttggagct    2640
cgttggtcag aagttgacga gggaagcggt aagtttgctg cgcttggggg cgttggatat    2700
tacgttgatg ggtttgccca ttgaggatcc agagattgag actcggctga ttagtttgga    2760
agagttttgc gt                                                        2772
```

<210> SEQ ID NO 16
<211> LENGTH: 717
<212> TYPE: DNA
<213> ORGANISM: Corynebacterium glutamicum
<220> FEATURE:
<221> NAME/KEY: CDS
<222> LOCATION: (10)..(714)
<220> FEATURE:
<221> NAME/KEY: mutation
<222> LOCATION: (556)
<223> OTHER INFORMATION: G->A mutation resulting in D/N poymorphism

<400> SEQUENCE: 16

```
ttgggtctc gtg gag att cgt tgg ttg gaa ggc ttt atc gcg gtc gcg gaa     51
          Val Glu Ile Arg Trp Leu Glu Gly Phe Ile Ala Val Ala Glu
           1               5                  10 gaa ttg cac ttt agt aat gct gcg att cgt ttg ggg atg ccg caa tcg        99
Glu Leu His Phe Ser Asn Ala Ala Ile Arg Leu Gly Met Pro Gln Ser
 15                  20                  25                  30 ccg ttg agt cag ttg atc cgg cgg ttg gag tcg gag ttg ggg cag aag       147
Pro Leu Ser Gln Leu Ile Arg Arg Leu Glu Ser Glu Leu Gly Gln Lys
                 35                  40                  45 ctt ttt gat cgc agt acc cgg tcg gtg gag tta act gcc gcg ggt cgg       195
Leu Phe Asp Arg Ser Thr Arg Ser Val Glu Leu Thr Ala Ala Gly Arg
             50                  55                  60 gcg ttt ttg cca cat gcc agg ggg att gtg gcg agc gct gcg gtg gcg       243
Ala Phe Leu Pro His Ala Arg Gly Ile Val Ala Ser Ala Ala Val Ala
         65                  70                  75 agg gaa gct gtg aat gct gcc gag ggg gag atc gtt ggt gtt gtt cgc       291
Arg Glu Ala Val Asn Ala Ala Glu Gly Glu Ile Val Gly Val Val Arg
 80                  85                  90 att ggt ttt tct ggt gtg ctg aac tat tcc acg ctg ccg ctt ttg acc       339
Ile Gly Phe Ser Gly Val Leu Asn Tyr Ser Thr Leu Pro Leu Leu Thr
 95                 100                 105                 110 agt gag gtg cat aaa cgg ctt cct aat gtg gag ttg gag ctc gtt ggt       387
Ser Glu Val His Lys Arg Leu Pro Asn Val Glu Leu Glu Leu Val Gly
                115                 120                 125 cag aag ttg acg agg gaa gcg gta agt ttg ctg cgc ttg ggg gcg ttg       435
Gln Lys Leu Thr Arg Glu Ala Val Ser Leu Leu Arg Leu Gly Ala Leu
            130                 135                 140 gat att acg ttg atg ggt ttg ccc att gag gat cca gag att gag act       483
Asp Ile Thr Leu Met Gly Leu Pro Ile Glu Asp Pro Glu Ile Glu Thr
        145                 150                 155 cgg ctg att agt ttg gaa gag ttt tgc gtg gtg ttg ccg aag gat cat       531
Arg Leu Ile Ser Leu Glu Glu Phe Cys Val Val Leu Pro Lys Asp His
    160                 165                 170 cgt ctt gcg ggg gaa gga gtg gtg aat ttg gtg gat ctg gct aaa gat       579
Arg Leu Ala Gly Glu Gly Val Val Asn Leu Val Asp Leu Ala Lys Asp
175                 180                 185                 190 ggg ttt gtg acg acg ccg gag ttt gcg ggg tct gtg ttt agg aat tcc       627
Gly Phe Val Thr Thr Pro Glu Phe Ala Gly Ser Val Phe Arg Asn Ser
                195                 200                 205 acc ttt cag ttg tgt gct gag gct ggt ttt gtg ccg agg atc agc cag       675
Thr Phe Gln Leu Cys Ala Glu Ala Gly Phe Val Pro Arg Ile Ser Gln
```

```
                                    210                 215                 220
          caa gtt aat gat cct tac atg gcg ctg ttg ttg gcg cgg tag              717
          Gln Val Asn Asp Pro Tyr Met Ala Leu Leu Leu Ala Arg
                  225                 230                 235
```

<210> SEQ ID NO 17
<211> LENGTH: 235
<212> TYPE: PRT
<213> ORGANISM: Corynebacterium glutamicum

<400> SEQUENCE: 17

```
Val Glu Ile Arg Trp Leu Glu Gly Phe Ile Ala Val Ala Glu Leu
 1               5                  10                  15

His Phe Ser Asn Ala Ala Ile Arg Leu Gly Met Pro Gln Ser Pro Leu
                20                  25                  30

Ser Gln Leu Ile Arg Arg Leu Glu Ser Glu Leu Gly Gln Lys Leu Phe
            35                  40                  45

Asp Arg Ser Thr Arg Ser Val Glu Leu Thr Ala Ala Gly Arg Ala Phe
        50                  55                  60

Leu Pro His Ala Arg Gly Ile Val Ala Ser Ala Val Ala Arg Glu
65                  70                  75                  80

Ala Val Asn Ala Ala Glu Gly Glu Ile Val Gly Val Arg Ile Gly
                85                  90                  95

Phe Ser Gly Val Leu Asn Tyr Ser Thr Leu Pro Leu Leu Thr Ser Glu
                100                 105                 110

Val His Lys Arg Leu Pro Asn Val Glu Leu Glu Leu Val Gly Gln Lys
            115                 120                 125

Leu Thr Arg Glu Ala Val Ser Leu Leu Arg Leu Gly Ala Leu Asp Ile
        130                 135                 140

Thr Leu Met Gly Leu Pro Ile Glu Asp Pro Glu Ile Glu Thr Arg Leu
145                 150                 155                 160

Ile Ser Leu Glu Glu Phe Cys Val Val Leu Pro Lys Asp His Arg Leu
                165                 170                 175

Ala Gly Glu Gly Val Val Asn Leu Val Asp Leu Ala Lys Asp Gly Phe
                180                 185                 190

Val Thr Thr Pro Glu Phe Ala Gly Ser Val Phe Arg Asn Ser Thr Phe
            195                 200                 205

Gln Leu Cys Ala Glu Ala Gly Phe Val Pro Arg Ile Ser Gln Gln Val
        210                 215                 220

Asn Asp Pro Tyr Met Ala Leu Leu Leu Ala Arg
225                 230                 235
```

<210> SEQ ID NO 18
<211> LENGTH: 627
<212> TYPE: DNA
<213> ORGANISM: Corynebacterium diphtheriae
<220> FEATURE:
<221> NAME/KEY: CDS
<222> LOCATION: (1)..(624)
<223> OTHER INFORMATION: RXA00655 protein homologue

<400> SEQUENCE: 18

```
ttg gcc gag gcg aaa agc acg aag acg acg agt cgt cga cgt aac cgt     48
Leu Ala Glu Ala Lys Ser Thr Lys Thr Thr Ser Arg Arg Arg Asn Arg
 1               5                  10                  15 ccg agc cct cgt cag cgc cta ttg gat ggc gca acg cag ctt ttt acc     96
Pro Ser Pro Arg Gln Arg Leu Leu Asp Gly Ala Thr Gln Leu Phe Thr
                20                  25                  30
```

```
acc gag gga att cgg gtg atc ggc att gat cgc att ttg cgt gag gct    144
Thr Glu Gly Ile Arg Val Ile Gly Ile Asp Arg Ile Leu Arg Glu Ala
        35                  40                  45 gat gta gcc aag gcg agt ttg tac tcc ctg ttc gga tcc aag gat gcg    192
Asp Val Ala Lys Ala Ser Leu Tyr Ser Leu Phe Gly Ser Lys Asp Ala
 50                  55                  60 ctg gtt att gcc tat ttg cag aac ttg gat gaa aag tgg cgt gag cag    240
Leu Val Ile Ala Tyr Leu Gln Asn Leu Asp Glu Lys Trp Arg Glu Gln
 65                  70                  75                  80 tat tac gag cgc act gct gag atg ggt tcg cca agc gag aaa att ctc    288
Tyr Tyr Glu Arg Thr Ala Glu Met Gly Ser Pro Ser Glu Lys Ile Leu
                85                  90                  95 gcg ttt ttt gat cag tgt att gat gag gag ccg ctg aag gat tat cgc    336
Ala Phe Phe Asp Gln Cys Ile Asp Glu Glu Pro Leu Lys Asp Tyr Arg
            100                 105                 110 ggt tcg cac ttc cag aat gct gct aac gag tac ccg cgc cca gag acg    384
Gly Ser His Phe Gln Asn Ala Ala Asn Glu Tyr Pro Arg Pro Glu Thr
        115                 120                 125 gat agt gag cgc gag atc gtg tcg gtt gtg atg gaa cat cgc cgg tgg    432
Asp Ser Glu Arg Glu Ile Val Ser Val Val Met Glu His Arg Arg Trp
130                 135                 140 tgt ttg gag acg tta act cag ttg ttg acg gag aag aac ggg tat ccc    480
Cys Leu Glu Thr Leu Thr Gln Leu Leu Thr Glu Lys Asn Gly Tyr Pro
145                 150                 155                 160 ggc act gtt cag gct aat cag ttg atg gtt ttt ctg gat ggt ggt ctt    528
Gly Thr Val Gln Ala Asn Gln Leu Met Val Phe Leu Asp Gly Gly Leu
                165                 170                 175 gcg ggt tgt cgt ctg aat cgc tcg gtg gag tcg ttg aag act gct cgg    576
Ala Gly Cys Arg Leu Asn Arg Ser Val Glu Ser Leu Lys Thr Ala Arg
            180                 185                 190 gat ctt gcg gtt cag ttg ctg tct gct cct cct gct gat tat tcg att    624
Asp Leu Ala Val Gln Leu Leu Ser Ala Pro Pro Ala Asp Tyr Ser Ile
        195                 200                 205 tag                                                                 627

<210> SEQ ID NO 19
<211> LENGTH: 208
<212> TYPE: PRT
<213> ORGANISM: Corynebacterium diphtheriae

<400> SEQUENCE: 19

Leu Ala Glu Ala Lys Ser Thr Lys Thr Thr Ser Arg Arg Arg Asn Ar

```
              130                 135                 140
Cys Leu Glu Thr Leu Thr Gln Leu Leu Thr Glu Lys Asn Gly Tyr Pro
145                 150                 155                 160

Gly Thr Val Gln Ala Asn Gln Leu Met Val Phe Leu Asp Gly Gly Leu
                165                 170                 175

Ala Gly Cys Arg Leu Asn Arg Ser Val Glu Ser Leu Lys Thr Ala Arg
            180                 185                 190

Asp Leu Ala Val Gln Leu Leu Ser Ala Pro Pro Ala Asp Tyr Ser Ile
        195                 200                 205

<210> SEQ ID NO 20
<211> LENGTH: 639
<212> TYPE: DNA
<213> ORGANISM: Corynebacterium efficiens YS-314
<220> FEATURE:
<221> NAME/KEY: CDS
<222> LOCATION: (1)..(636)
<223> OTHER INFORMATION: coding for RXA00655 protein homologue

<400> SEQUENCE: 20 gtg gct gtc agc gct tca gga aag agt agg acc agt aca ggg ggc agg      48
Val Ala Val Ser Ala Ser Gly Lys Ser Arg Thr Ser Thr Gly Gly Arg
 1               5                  10                  15 cga cgt gat cgc ccg agc ccc cgg cag cgt ctg ctc gac agc gca acg      96
Arg Arg Asp Arg Pro Ser Pro Arg Gln Arg Leu Leu Asp Ser Ala Thr
                20                  25                  30 aat ctg ttc acc acc gag ggc atc cgg gtc atc ggc atc gac cgt atc     144
Asn Leu Phe Thr Thr Glu Gly Ile Arg Val Ile Gly Ile Asp Arg Ile
            35                  40                  45 ctt cgt gag gcg gat gtg gcc aag gcc agc ctg tac tcc ctc ttc ggt     192
Leu Arg Glu Ala Asp Val Ala Lys Ala Ser Leu Tyr Ser Leu Phe Gly
        50                  55                  60 tcc aag gat gct ctg gtg atc gcc tac ctg gaa aat ctg gat cag cag     240
Ser Lys Asp Ala Leu Val Ile Ala Tyr Leu Glu Asn Leu Asp Gln Gln
65                  70                  75                  80 tgg cgt gat gcg tgg cat gag cgg acg gac cag ctc aag gac ccg gag     288
Trp Arg Asp Ala Trp His Glu Arg Thr Asp Gln Leu Lys Asp Pro Glu
                85                  90                  95 gat aag atc atc gcc ttc ttc gac cag tgc atc gag gag gag ccg aag     336
Asp Lys Ile Ile Ala Phe Phe Asp Gln Cys Ile Glu Glu Glu Pro Lys
            100                 105                 110 aag ggc ttc cgg ggg tcc cac ttc cag aat gcg gcg aat gag tat cca     384
Lys Gly Phe Arg Gly Ser His Phe Gln Asn Ala Ala Asn Glu Tyr Pro
        115                 120                 125 cgt ccg gag acg gaa tcc gag aag ggt att gtc gcc gcg gtc atg gag     432
Arg Pro Glu Thr Glu Ser Glu Lys Gly Ile Val Ala Ala Val Met Glu
    130                 135                 140 cac cgt cgt tgg tgt cat cag acg ctg acc gat ctg ctc acg gag aag     480
His Arg Arg Trp Cys His Gln Thr Leu Thr Asp Leu Leu Thr Glu Lys
145                 150                 155                 160 aat ggt tat ccc ggc acc acc cag gcg aat cag ctg ctg gtg ttc ctt     528
Asn Gly Tyr Pro Gly Thr Thr Gln Ala Asn Gln Leu Leu Val Phe Leu
                165                 170                 175 gat ggt ggt ctg gcg ggg tcg agg ctg gtt cag aat atc ggc ccc ttg     576
Asp Gly Gly Leu Ala Gly Ser Arg Leu Val Gln Asn Ile Gly Pro Leu
            180                 185                 190 gaa acg gcc cgt gac ctg gcc cgg cag ttg ctg tcc gca cca ccg gcg     624
Glu Thr Ala Arg Asp Leu Ala Arg Gln Leu Leu Ser Ala Pro Pro Ala
        195                 200                 205 gat tac tcg atc tag                                                  639
```

Asp Tyr Ser Ile
    210

<210> SEQ ID NO 21
<211> LENGTH: 212
<212> TYPE: PRT
<213> ORGANISM: Corynebacterium efficiens YS-314

<400> SEQUENCE: 21

Val Ala Val Ser Ala Ser Gly Lys Ser Arg Thr Ser Thr Gly Gly Arg
 1               5                   10                  15

Arg Arg Asp Arg Pro Ser Pro Arg Gln Arg Leu Leu Asp Ser Ala Thr
            20                  25                  30

Asn Leu Phe Thr Thr Glu Gly Ile Arg Val Ile Gly Ile Asp Arg Ile
        35                  40                  45

Leu Arg Glu Ala Asp Val Ala Lys Ala Ser Leu Tyr Ser Leu Phe Gly
    50                  55                  60

Ser Lys Asp Ala Leu Val Ile Ala Tyr Leu Glu Asn Leu Asp Gln Gln
65                  70                  75                  80

Trp Arg Asp Ala Trp His Glu Arg Thr Asp Gln Leu Lys Asp Pro Glu
                85                  90                  95

Asp Lys Ile Ile Ala Phe Phe Asp Gln Cys Ile Glu Glu Pro Lys
            100                 105                 110

Lys Gly Phe Arg Gly Ser His Phe Gln Asn Ala Ala Asn Glu Tyr Pro
        115                 120                 125

Arg Pro Glu Thr Glu Ser Glu Lys Gly Ile Val Ala Ala Val Met Glu
    130                 135                 140

His Arg Arg Trp Cys His Gln Thr Leu Thr Asp Leu Leu Thr Glu Lys
145                 150                 155                 160

Asn Gly Tyr Pro Gly Thr Thr Gln Ala Asn Gln Leu Leu Val Phe Leu
                165                 170                 175

Asp Gly Gly Leu Ala Gly Ser Arg Leu Val Gln Asn Ile Gly Pro Leu
            180                 185                 190

Glu Thr Ala Arg Asp Leu Ala Arg Gln Leu Leu Ser Ala Pro Pro Ala
        195                 200                 205

Asp Tyr Ser Ile
    210

<210> SEQ ID NO 22
<211> LENGTH: 588
<212> TYPE: DNA
<213> ORGANISM: Streptomyces coelicolor
<220> FEATURE:
<221> NAME/KEY: CDS
<222> LOCATION: (1)..(585)
<223> OTHER INFORMATION: coding for RXA00655 protein homologue

<400> SEQUENCE: 22 atg aca tcg acc gcc gcc aga ccg ggc aga gtg gcg aag ctg ccg ccc      48
Met Thr Ser Thr Ala Ala Arg Pro Gly Arg Val Ala Lys Leu Pro Pro
 1               5                   10                  15 cgc gag cgc atc ctc gac gcg gcc gag gag ctc ttc cag ggc gag ggc      96
Arg Glu Arg Ile Leu Asp Ala Ala Glu Glu Leu Phe Gln Gly Glu Gly
            20                  25                  30 atc cga cgc gtg ggg gtc cag gcg atc gcc gag cgg gcc gag acc acc     144
Ile Arg Arg Val Gly Val Gln Ala Ile Ala Glu Arg Ala Glu Thr Thr
        35                  40                  45 aag atg gcg atc tac cgg cac ttc gag acc aag gac gca ctc gtc gcc     192
Lys Met Ala Ile Tyr Arg His Phe Glu Thr Lys Asp Ala Leu Val Ala

```
              50                  55                  60
gaa tgg ctg cgg atc ctg gcc gcc gag tac cag gcg gcc ttc gac cgc     240
Glu Trp Leu Arg Ile Leu Ala Ala Glu Tyr Gln Ala Ala Phe Asp Arg
 65                  70                  75                  80 gtc gag gcc gaa cat ccc ggc cgg ccc cgg gag cag atc ctg ggc ctc     288
Val Glu Ala Glu His Pro Gly Arg Pro Arg Glu Gln Ile Leu Gly Leu
                 85                  90                  95 gcc cgc ttc atc gcc gac ggg ctg ccg ggg ctc tcg cac cgg ggc tgc     336
Ala Arg Phe Ile Ala Asp Gly Leu Pro Gly Leu Ser His Arg Gly Cys
            100                 105                 110 ccc ttc atc aac tcc ctc gcc gag ctg ccc gac cgc tcc cac ccc gcg     384
Pro Phe Ile Asn Ser Leu Ala Glu Leu Pro Asp Arg Ser His Pro Ala
        115                 120                 125 cga cgg gtg atc gag gag cac aag gcc cgc cag acc cgc agg ctg gtc     432
Arg Arg Val Ile Glu Glu His Lys Ala Arg Gln Thr Arg Arg Leu Val
    130                 135                 140 ggc atg tgt gcc gag gcg ggg atg ccc gac ccc gaa cag gtc gcg gcc     480
Gly Met Cys Ala Glu Ala Gly Met Pro Asp Pro Glu Gln Val Ala Ala
145                 150                 155                 160 cag atc acc ttc gtc ctc gaa ggg gcg cag gtc agc acg cag aac gca     528
Gln Ile Thr Phe Val Leu Glu Gly Ala Gln Val Ser Thr Gln Asn Ala
                165                 170                 175 agc atc gac cgg gcg ggg gag cgg ttg atg cgc atc gtc gag gcg atc     576
Ser Ile Asp Arg Ala Gly Glu Arg Leu Met Arg Ile Val Glu Ala Ile
            180                 185                 190 gtc gac cag tag                                                     588
Val Asp Gln
        195

<210> SEQ ID NO 23
<211> LENGTH: 195
<212> TYPE: PRT
<213> ORGANISM: Streptomyces coelicolor

<400> SEQUENCE: 23

Met Thr Ser Thr Ala Ala Arg Pro Gly Arg Val Ala Lys Leu Pro Pro
  1               5                  10                  15

Arg Glu Arg Ile Leu Asp Ala Ala Glu Glu Leu Phe Gln Gly Glu Gly
                 20                  25                  30

Ile Arg Arg Val Gly Val Gln Ala Ile Ala Glu Arg Ala Glu Thr Thr
             35                  40                  45

Lys Met Ala Ile Tyr Arg His Phe Glu Thr Lys Asp Ala Leu Val Ala
         50                  55                  60

Glu Trp Leu Arg Ile Leu Ala Ala Glu Tyr Gln Ala Ala Phe Asp Arg
 65                  70                  75                  80

Val Glu Ala Glu His Pro Gly Arg Pro Arg Glu Gln Ile Leu Gly Leu
                 85                  90                  95

Ala Arg Phe Ile Ala Asp Gly Leu Pro Gly Leu Ser His Arg Gly Cys
            100                 105                 110

Pro Phe Ile Asn Ser Leu Ala Glu Leu Pro Asp Arg Ser His Pro Ala
        115                 120                 125

Arg Arg Val Ile Glu Glu His Lys Ala Arg Gln Thr Arg Arg Leu Val
    130                 135                 140

Gly Met Cys Ala Glu Ala Gly Met Pro Asp Pro Glu Gln Val Ala Ala
145                 150                 155                 160

Gln Ile Thr Phe Val Leu Glu Gly Ala Gln Val Ser Thr Gln Asn Ala
                165                 170                 175
```

```
Ser Ile Asp Arg Ala Gly Glu Arg Leu Met Arg Ile Val Glu Ala Ile
        180                 185                 190

Val Asp Gln
        195

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 24
ggaaacagta tgaccatg                                                   18

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 25
gtaaaacgac ggccagt                                                    17
```